(12) United States Patent
Choi et al.

(10) Patent No.: US 9,505,784 B2
(45) Date of Patent: *Nov. 29, 2016

(54) FUSED 2-AMINOTHIAZOLE COMPOUNDS

(71) Applicant: Dana-Farber Cancer Institute, Inc., Boston, MA (US)

(72) Inventors: Hwan Geun Choi, Chestnut Hill, MA (US); Taebo Sim, Seoul (KR); Nathanael Gray, Boston, MA (US); Wenjun Zhou, Brighton, MA (US); Jae Won Chang, San Diego, CA (US); Jianming Zhang, Cambridge, MA (US); Ellen Weisberg, Nashua, NH (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/321,242

(22) Filed: Jul. 1, 2014

(65) Prior Publication Data

US 2015/0094315 A1    Apr. 2, 2015

Related U.S. Application Data

(63) Continuation of application No. 13/376,539, filed as application No. PCT/US2010/038518 on Jun. 14, 2010, now Pat. No. 8,765,747.

(60) Provisional application No. 61/186,584, filed on Jun. 12, 2009.

(51) Int. Cl.
| | |
|---|---|
| C07D 513/04 | (2006.01) |
| A61K 31/425 | (2006.01) |
| A01N 43/78 | (2006.01) |
| A61K 31/437 | (2006.01) |
| A61K 31/496 | (2006.01) |
| A61K 31/4985 | (2006.01) |
| A61K 31/506 | (2006.01) |
| A61K 31/5377 | (2006.01) |

(52) U.S. Cl.
CPC .......... *C07D 513/04* (2013.01); *A61K 31/437* (2013.01); *A61K 31/496* (2013.01); *A61K 31/4985* (2013.01); *A61K 31/506* (2013.01); *A61K 31/5377* (2013.01)

(58) Field of Classification Search
CPC ................................................... C07D 513/04
See application file for complete search history.

(56) References Cited

U.S. PATENT DOCUMENTS

| | | | |
|---|---|---|---|
| 4,231,938 A | 11/1980 | Monaghan et al. | |
| 4,782,084 A | 11/1988 | Vyas et al. | |
| 4,885,314 A | 12/1989 | Vyas et al. | |
| 5,420,245 A | 5/1995 | Brown et al. | |
| 5,510,510 A | 4/1996 | Patel et al. | |
| 5,523,430 A | 6/1996 | Patel et al. | |
| 5,532,359 A | 7/1996 | Marsters, Jr. et al. | |
| 5,571,792 A | 11/1996 | Bolton et al. | |
| 5,589,485 A | 12/1996 | Hochlowski et al. | |
| 5,602,098 A | 2/1997 | Sebti et al. | |
| 5,661,152 A | 8/1997 | Bishop et al. | |
| 6,939,874 B2 | 9/2005 | Harmange et al. | |
| 7,115,617 B2 | 10/2006 | Buchanan et al. | |
| 7,928,140 B2 * | 4/2011 | Booker et al. | 514/514 |
| 8,765,747 B2 | 7/2014 | Choi et al. | |
| 9,180,127 B2 | 11/2015 | Gray et al. | |
| 2004/0106634 A1 | 6/2004 | Satoh et al. | |
| 2006/0189627 A1 | 8/2006 | Laird et al. | |
| 2007/0093537 A1 | 4/2007 | Hynes et al. | |
| 2007/0185171 A1 | 8/2007 | Germain et al. | |
| 2007/0225286 A1 | 9/2007 | Ren et al. | |
| 2007/0281907 A1 | 12/2007 | Watkins | |
| 2008/0039629 A1 | 2/2008 | Ramesh et al. | |
| 2008/0103167 A1 | 5/2008 | Bebernitz et al. | |
| 2008/0214501 A1 | 9/2008 | Pan et al. | |
| 2009/0054392 A1 | 2/2009 | Pelletier et al. | |
| 2009/0054405 A1 | 2/2009 | Booker et al. | |
| 2009/0105250 A1 | 4/2009 | Sim et al. | |
| 2011/0098280 A1 | 4/2011 | Garcia-Echeverria et al. | |
| 2011/0178070 A1 * | 7/2011 | Gong et al. | 514/221 |
| 2011/0212053 A1 | 9/2011 | Qian et al. | |
| 2012/0088766 A1 | 4/2012 | Choi et al. | |
| 2012/0165309 A1 | 6/2012 | Takahashi et al. | |
| 2012/0329771 A1 | 12/2012 | Treu et al. | |
| 2013/0040949 A1 | 2/2013 | Gray et al. | |
| 2014/0309249 A1 | 10/2014 | Gray et al. | |
| 2015/0157629 A1 | 6/2015 | Gray et al. | |
| 2015/0246913 A1 | 9/2015 | Gray et al. | |
| 2015/0274738 A1 | 10/2015 | Gray et al. | |

FOREIGN PATENT DOCUMENTS

| | | |
|---|---|---|
| CA | 2503646 A1 | 5/2004 |
| CA | 2550128 A1 | 6/2005 |

(Continued)

OTHER PUBLICATIONS

Ben-Av et al., Induction of vascular endothelial growth factor expression in synovial fibroblasts by prostaglandin E and interleukin-1: a potential mechanism for inflammatory angiogenesis. FEBS Lett. Sep. 18, 1995;372(1):83-7.

(Continued)

*Primary Examiner* — Nyeemah A Grazier
*Assistant Examiner* — Amanda L Aguirre
(74) *Attorney, Agent, or Firm* — Wolf, Greenfield & Sacks, P.C.

(57) ABSTRACT

The present application relates to therapeutic organic compounds, compositions comprising an effective amount of a therapeutic organic compound; and methods for treating and preventing disease comprising administering and effective amount of a therapeutic organic compound to a subject in need thereof.

27 Claims, 1 Drawing Sheet

(56) References Cited

FOREIGN PATENT DOCUMENTS

| | | |
|---|---|---|
| CA | 2563212 A1 | 10/2005 |
| EP | 0 604 181 A1 | 6/1994 |
| EP | 0 618 221 A2 | 10/1994 |
| EP | 0 675 112 A1 | 10/1995 |
| EP | 0 696 593 A2 | 2/1996 |
| EP | 1 935 890 A1 | 6/2008 |
| EP | 2 311 842 A2 | 4/2011 |
| JP | 2007-500725 | 1/2007 |
| JP | 2009-510110 | 3/2009 |
| JP | 2011-516533 | 5/2011 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/24612 A1 | 9/1995 |
| WO | WO 95/25086 A1 | 9/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/05529 A1 | 2/1996 |
| WO | WO 96/06138 A1 | 2/1996 |
| WO | WO 96/06193 A1 | 2/1996 |
| WO | WO 96/16443 A1 | 5/1996 |
| WO | WO 96/17861 A1 | 6/1996 |
| WO | WO 96/21456 A1 | 7/1996 |
| WO | WO 96/21701 A2 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 | 10/1996 |
| WO | WO 96/30362 A1 | 10/1996 |
| WO | WO 96/30363 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/02920 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 | 6/1997 |
| WO | WO 97/23478 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 00/44777 A1 | 8/2000 |
| WO | WO 00/50032 | 8/2000 |
| WO | WO 00/61186 A1 | 10/2000 |
| WO | WO 02/076986 A1 | 10/2002 |
| WO | WO 02/079197 A1 | 10/2002 |
| WO | WO 02/080926 A1 | 10/2002 |
| WO | WO 02/096905 A1 | 12/2002 |
| WO | WO 02/102800 A1 | 12/2002 |
| WO | WO 03/026664 A1 | 4/2003 |
| WO | WO 2004/005283 A1 | 1/2004 |
| WO | WO 2004/039796 A1 | 5/2004 |
| WO | WO 2004/078757 A2 | 9/2004 |
| WO | WO 2004/087699 A2 | 10/2004 |
| WO | WO 2004/100868 A2 | 11/2004 |
| WO | WO 2005/011597 A2 | 2/2005 |
| WO | WO 2005/058891 A1 | 6/2005 |
| WO | WO 2005/097790 A1 | 10/2005 |
| WO | WO 2005/116025 A2 | 12/2005 |
| WO | WO 2006/024834 A1 | 3/2006 |
| WO | WO 2006/031806 A2 | 3/2006 |
| WO | WO 2006/040568 A1 | 4/2006 |
| WO | WO 2007/035428 A1 | 3/2007 |
| WO | WO 2007/041365 A2 | 4/2007 |
| WO | WO 2007/042786 A2 | 4/2007 |
| WO | WO 2007/129195 A2 | 11/2007 |
| WO | WO 2007/138277 A1 | 12/2007 |
| WO | WO 2008/068171 A1 | 6/2008 |
| WO | WO 2008/112913 A1 | 9/2008 |
| WO | WO 2008/124393 A1 | 10/2008 |
| WO | WO 2008/144253 A1 | 11/2008 |
| WO | WO 2008/151183 A1 | 12/2008 |
| WO | WO 2009/017822 A2 | 2/2009 |
| WO | WO 2009/032694 A1 | 3/2009 |
| WO | WO 2009/125200 A2 | 10/2009 |
| WO | WO 2009/145360 A1 | 12/2009 |
| WO | WO 2009/155017 A2 | 12/2009 |
| WO | WO 2010/008847 A2 | 1/2010 |
| WO | WO 2010/051781 A1 | 5/2010 |
| WO | WO 2010/125799 | 11/2010 |
| WO | WO 2010/144909 A1 | 12/2010 |
| WO | WO 2013/014162 A1 | 1/2013 |
| WO | WO 2013/074986 A1 | 5/2013 |
| WO | WO 2013/154778 A1 | 10/2013 |
| WO | WO 2014/063061 A1 | 4/2014 |
| WO | WO 2014/063068 A1 | 4/2014 |

OTHER PUBLICATIONS

Benezra et al., In vivo angiogenic activity of interleukins. Arch Ophthalmol. Apr. 1990;108(4):573-6.

Black et al., Expression of platelet-derived growth factor transcripts in medulloblastomas and ependymomas. Pediatr Neurosurg. 1996;24(2):74-8.

Bower, Tumor Angiogenesis—New Drugs on the Block. Nature Biotechnology. Oct. 1999;17:963-8.

Chakraborty et al., Developmental expression of the cyclooxygenase-1 and cyclooxygenase-2 genes in the peri-implantation mouse uterus and their differential regulation by the blastocyst and ovarian steroids. J Mol Endocrinol. Apr. 1996;16(2):107-22.

Chiarugi et al., Cox-2, iNOS and p53 as play-makers of tumor angiogenesis (review). Int J Mol Med. Dec. 1998;2(6):715-9.

Daley et al., Transformation of an interleukin 3-dependent hematopoietic cell line by the chronic myelogenous leukemia-specific P210bcr/abl protein. Proc Natl Acad Sci U S A. Dec. 1988;85(23):9312-6.

Diaz-Flores et al., Intense Vascular Sprouting From Rat Femoral Vein Induced by Prostaglandins E1 and E2. Anat Rec. 1994;238:68-74.

Fernandez et al., Neovascularization produced by angiotensin II. J Lab Clin Med. Feb. 1985;105(2):141-5.

Fleisher et al. Improved oral drug delivery: solubility limitations overcome by the use of prodrugs. Advanced Drug Delivery Reviews. May 22, 1996;19(2):115-30.

Golub et al., Fusion of PDGF receptor beta to a novel ets-like gene, tel, in chronic myelomonocytic leukemia with t(5;12) chromosomal translocation. Cell. Apr. 22, 1994;77(2):307-16.

Gu et al., Effect of novel CAAX peptidomimetic farnesyltransferase inhibitor on angiogenesis in vitro and in vivo. Eur J Cancer. Sep. 1999;35(9):1394-401.

Harada et al., Expression and regulation of vascular endothelial growth factor in osteoblasts. Clin Orthop Relat Res. Apr. 1995;(313):76-80.

Hla et al., T, Neilson K. Human cyclooxygenase-2 cDNA. Proc Natl Acad Sci U S A. Aug. 15, 1992;89(16):7384-8.

(56) References Cited

OTHER PUBLICATIONS

Jouve et al. Oxidative Cyclization of N-Methyl-and N-Benzoylpyridylthioureas. Journal of Heterocyclic Chemistry. 2003;40(2):261-8.
Kim et al., Inhibition of vascular endothelial growth factor-induced angiogenesis suppresses tumour growth in vivo. Nature. Apr. 29, 1993;362(6423):841-4.
Majima et al., Significant roles of inducible cyclooxygenase (COX)-2 in angiogenesis in rat sponge implants. Jpn J Pharmacol. Oct. 1997;75(2):105-14.
Matulonis et al., Interleukin-3 and p210 BCR/ABL Activate Both Unique and Overlapping Pathways of Signal Transduction in a Factor-Dependent Myeloid Cell Line. Experimental Hematology. 1993;21:1460-6.
McCarthy et al., 11-Ketotigogenin cellobioside (pamaqueside): a potent cholesterol absorption inhibitor in the hamster. J Med Chem. May 10, 1996;39(10):1935-7.
Okuda et al., p210BCR/ABL, p190BCR/ABL, and TEL/ABL activate similar signal transduction pathways in hematopoietic cell lines. Oncogene. Sep. 19, 1996;13(6):1147-52.
Ray et al., Identification of BCR-ABL point mutations conferring resistance to the Abl kinase inhibitor AMN107 (nilotinib) by a random mutagenesis study. Blood. Jun. 1, 2007;109(11):5011-5. Epub Feb. 15, 2007.
Robinson et al., Discovery of the hemifumarate and (alpha-L-alanyloxy)methyl ether as prodrugs of an antirheumatic oxindole: prodrugs for the enolic OH group. J Med Chem. Jan. 5, 1996;39(1):10-8.
Sattler et al., The proto-oncogene product p120CBL and the adaptor proteins CRKL and c-CRK link c-ABL, p190BCR/ABL and p210BCR/ABL to the phosphatidylinositol-3' kinase pathway. Oncogene. Feb. 15, 1996;12(4):839-46.
Seed et al., The inhibition of colon-26 adenocarcinoma development and angiogenesis by topical diclofenac in 2.5% hyaluronan. Cancer Res. May 1, 1997;57(9):1625-9.
Tsujii et al., Cyclooxygenase regulates angiogenesis induced by colon cancer cells. Cell. May 29, 1998;93(5):705-16.
Weisberg et al., Characterization of AMN107, a selective inhibitor of native and mutant Bcr-Abl. Cancer Cell. Feb. 2005;7(2):129-41.
Weisberg et al., Discovery and characterization of novel mutant FLT3 kinase inhibitors. Mol Cancer Ther. Sep. 2010;9(9):2468-77. Epub Aug. 31, 2010.
Xin et al., Peroxisome proliferator-activated receptor gamma ligands are potent inhibitors of angiogenesis in vitro and in vivo. J Biol Chem. Mar. 26, 1999;274(13):9116-21.
Ziche et al., Role of prostaglandin E1 and copper in angiogenesis. J Natl Cancer Inst. Aug. 1982;69(2):475-82.
International Search Report and Written Opinion for PCT/US2012/065618, mailed Mar. 19, 2013.
International Preliminary Report on Patentability for PCT/US2012/065618, mailed May 30, 2014.
International Search Report and Written Opinion for PCT/US2013/065708, mailed Feb. 4, 2014.
International Search Report and Written Opinion for PCT/US2013/065689, mailed Mar. 4, 2014.
International Search Report and Written Opinion for PCT/US2013/065698, mailed Feb. 20, 2014.
International Search Report and Written Opinion for PCT/US2014/061232, mailed Dec. 23, 2014.
Extended European Search Report for EP 10786967.9, mailed Oct. 23, 2012.
International Search Report and Written Opinion for PCT/US2010/038518, mailed Aug. 6, 2010.
International Preliminary Report on Patentability for PCT/US2010/038518, mailed Dec. 22, 2011.
Extended European Search Report for EP 10844280.7, mailed Apr. 17, 2013.
International Search Report and Written Opinion for PCT/US2010/062310, mailed Oct. 4, 2011.
International Preliminary Report on Patentability for PCT/US2010/062310, mailed Jul. 12, 2012.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyflphenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Stanovnik et al., The Tautomerism of Heterocycles: Substituent Tautomerism of Six-Membered Ring Heterocycles. Advances in Heterocyclic Chemistry. 2006;91:1-134.
Zhang et al., Discovery of potent and selective covalent inhibitors of JNK. Chem Biol. Jan. 27, 2012;19(1):140-54. doi: 10.1016/j.chembiol.2011.11.010.
International Preliminary Report on Patentability for PCT/US2013/065708, mailed Apr. 30, 2015.
International Preliminary Report on Patentability for PCT/US2013/065689, mailed Apr. 30, 2015.
International Preliminary Report on Patentability for PCT/US2013/065698, mailed Apr. 30, 2015.
International Search Report and Written Opinion for PCT/US2015/027312, mailed Jul. 10, 2015.
International Search Report and Written Opinion for PCT/US2015/027294, mailed Jul. 10, 2015.
International Search Report and Written Opinion for PCT/US2015/41348, mailed Sep. 24, 2015.
Partial European Search Report for EP 15160591.2, dated Jul. 14, 2015.
Extended European Search Report for EP 15160591.2, dated Nov. 2, 2015.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials. 16 pages.
Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.

\* cited by examiner

FUSED 2-AMINOTHIAZOLE COMPOUNDS

RELATED APPLICATIONS

This application is a continuation of and claims priority under 35 U.S.C. §120 to U.S. application Ser. No. 13/376,539, filed Dec. 6, 2011, which is a §371 filing based on International Application No. PCT/US2010/038518, filed Jun. 14, 2010, which claims the benefit of Provisional U.S. Patent Application 61/186,584, filed Jun. 12, 2009. The entire contents of these patent applications are hereby incorporated herein by reference.

GOVERNMENT SUPPORT

This invention was made with government support under grant numbers CA130876 and GM079575 awarded by the National Institutes of Health. The government has certain rights in the invention.

BACKGROUND

According to data collected by the American Cancer Society, more than 1.43 million people in the United States were diagnosed with cancer in 2008. Although earlier diagnoses and improved treatments have allowed for modest increases in five-year survival rates, the overall mortality rate per 100,000 people has gone down only 5 percent since 1950 due to the increased incidence of several types of cancer over the same period (SEER Cancer Statistics Review 1975-2004, NCI "55-Year Trends in U.S. Cancer Death Rates").

Attending to this ongoing medical need, research directed toward the mechanisms by which cancer cells proliferate and survive has implicated the deregulation of protein kinases. Therefore, methods of modulating or inhibiting kinase activity, including the use of small molecule agents, represent a promising direction in oncology drug development.

Thus, there remains a need for compounds that inhibit the activity of one or more protein kinases, as they can be expected to be useful in the treatment of cancer.

SUMMARY OF THE INVENTION

The invention provides compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, c-kit, PDGFR and Src kinases. Such diseases include, for example, cancer, e.g. pancreatic cancer, non-small cell lung cancer, gastrointestinal stromal tumor, or chronic myelogenous leukemia.

Thus, in one aspect provided herein is a compound of Formula I. In one embodiment, Formula I is represented as Formula II.

In another aspect, provided herein is a compound of Formula III.

In another aspect, provided herein is a method of treating cancer, comprising administering to a subject in need thereof a compound of Formula I. The cancer can be selected from the group consisting of multiple myeloma, chronic myelogenous leukemia, pancreatic cancer, non-small cell lung cancer, lung cancer, breast cancer, colon cancer, ovarian cancer, prostate cancer, malignant melanoma, non-melanoma skin cancers, gastrointestinal stromal tumors, hematologic tumors, hematologic malignancies, childhood leukemia, childhood lymphomas, multiple myeloma, Hodgkin's disease, lymphomas of lymphocytic origin, lymphomas of cutaneous origin, acute leukemia, chronic leukemia, acute lymphoblastic leukemia, acute myelocytic leukemia, chronic myelocytic leukemia, plasma cell neoplasm, lymphoid neoplasm and cancers associated with AIDS. In another embodiment, the cancer is pancreatic cancer or non-small cell lung cancer. In still another embodiment, the cancer is gastrointestinal stromal tumor or chronic myelogenous leukemia. In yet another embodiment, the cancer is acute myeloid leukemia. The cancer can be resistant to treatment with Gleevec or imatinib, wherein treatment-resistance can be due to one or more point-mutations in an Abl kinase, a BCR-Abl kinase domain, a c-kit kinase, an Src kinase or a PDGFR kinase.

In another aspect, provided herein is the use of a compound of Formula I for the manufacture of a medicament for treating cancer in a subject.

In another aspect, provided herein is the use of a compound of Formula III for the manufacture of a medicament for treating cancer in a subject.

In yet another aspect, provided herein is a method of inhibiting the activity of a kinase, comprising utilizing a compound of Formula I. In one embodiment, the kinase is selected from Abl, Abl (T315I), BCR-Abl, BRAF, CDK11, CDK5, CDK2, CDK3, CDK7, DDR1, FLT1, FLT3, FLT4, HIPK1, kit, LOK, p38-gamma, PDGFRA, PDGFRB, or Src comprising utilizing a compound of Formula I.

In still another aspect, provided herein is a method of inhibiting the activity of a kinase, comprising utilizing a compound of Formula III. In one embodiment, the kinase is selected from Abl, Abl (T315I), BCR-Abl, BRAF, CDK11, CDK5, CDK2, CDK3, CDK7, DDR1, FLT1, FLT3, FLT4, HIPK1, kit, LOK, p38-gamma, PDGFRA, PDGFRB, or Src comprising utilizing a compound of Formula III.

In another aspect, provided herein is a method of inhibiting the activity of Abl kinase, BCR-Abl kinase, c-kit kinase, PDGFRA or PDGFRB kinase, or Src kinase comprising utilizing a compound of Formula I. In yet another embodiment, provided herein is a method of treating a disease in a subject, wherein the disease etiology or progression is at least partially mediated by the activity of Abl kinase, BCR-Abl kinase, c-kit kinase, Src kinase, or PDGFR kinase, comprising administering to the subject a compound of Formula I. In still another embodiment, provided herein is a method of treating cancer, comprising administering to a subject in need thereof a compound of Formula I in combination with a pharmaceutically effective amount of an additional anti-cancer agent. The additional anti-cancer agent can be imatinib or nilotinib.

In still another aspect, provided herein is a method of inhibiting the activity of Abl kinase, BCR-Abl kinase, c-kit kinase, PDGFRA or PDGFRB kinase, or Src kinase comprising utilizing a compound of Formula III. In yet another embodiment, provided herein is a method of treating a disease in a subject, wherein the disease etiology or progression is at least partially mediated by the activity of Abl kinase, BCR-Abl kinase, c-kit kinase, Src kinase, or PDGFR kinase, comprising administering to the subject a compound of Formula III. In still another embodiment, provided herein is a method of treating cancer, comprising administering to a subject in need thereof a compound of Formula III in combination with a pharmaceutically effective amount of an additional anti-cancer agent. The additional anti-cancer agent can be imatinib or nilotinib.

In another aspect, provided herein is a method of inhibiting the activity of FLT3 kinase comprising utilizing a compound of Formula III. In yet another embodiment, provided herein is a method of treating a disease in a subject, wherein the disease etiology or progression is at least partially mediated by the activity of FLT3 kinase, comprising administering to the subject a compound of Formula III. In still another embodiment, provided herein is a method of treating cancer, comprising administering to a subject in need thereof a compound of Formula III in combination with a pharmaceutically effective amount of an additional anti-cancer agent.

DETAILED DESCRIPTION OF THE INVENTION

Compounds of the Invention

Figure 1:
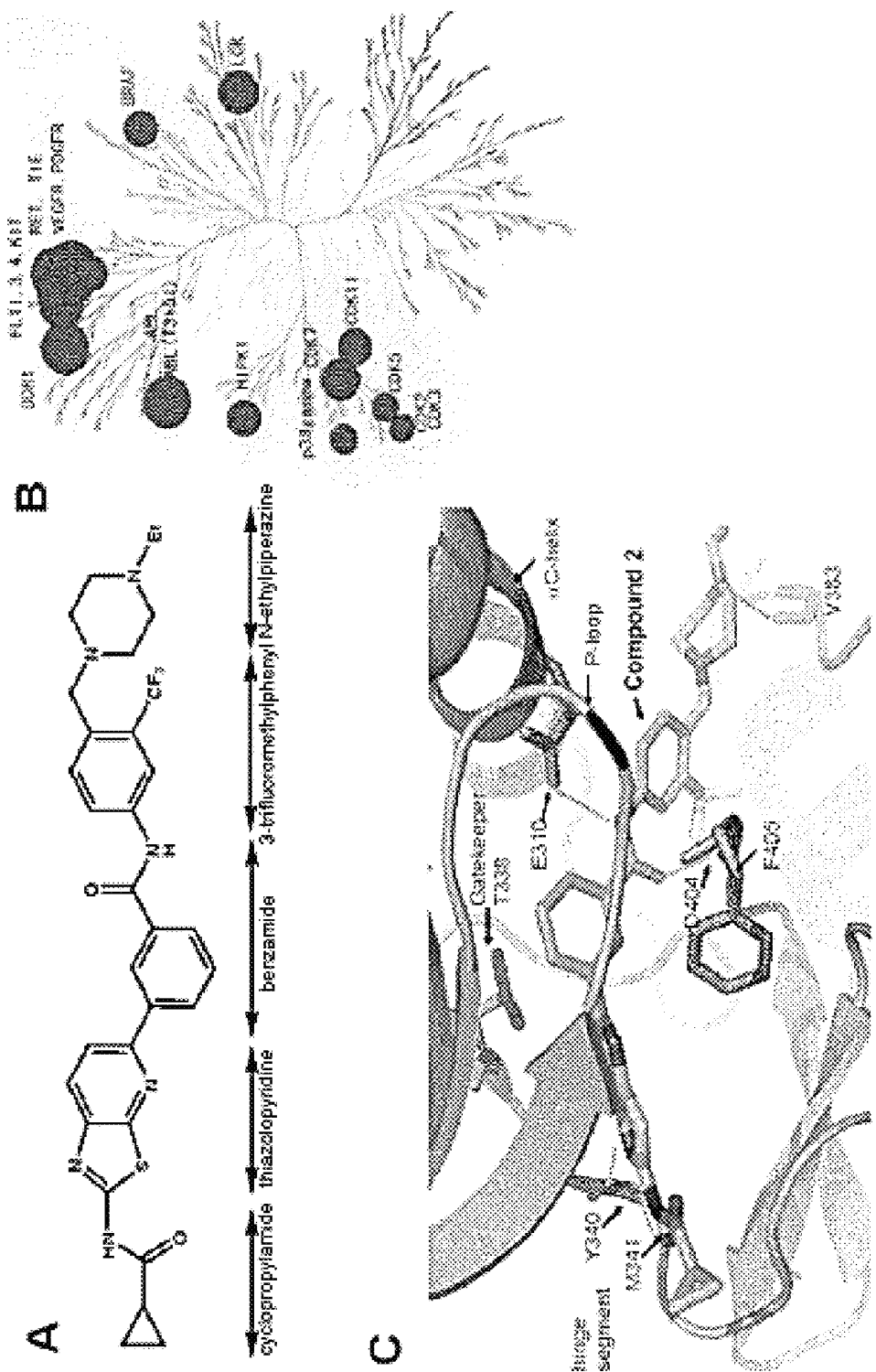
FIG. 1A shows a. Chemical structure of compound 2 (Table A).
FIG. 1B shows the kinase selectivity of compound 2.
FIG. 1C shows the crystal structure of compound 2 with Src kinase domain showing the ATP-binding site.

This invention is directed toward compounds, intermediates thereto and derivatives thereof, as well as pharmaceutical compositions containing the compounds for use in treatment of protein kinase-associated disorders. The compounds of the invention or compositions thereof are useful as inhibitors of the kinase enzymes c-Abl, c-kit, BCR-Abl, PDGFR and combinations thereof. Furthermore, the compounds of the invention or compositions thereof can be used in the treatment of cancer, e.g. pancreatic cancer, non-small cell lung cancer, gastrointestinal stromal tumor, or chronic myelogenous leukemia. The present invention is also directed to methods of inhibiting protein kinase activity in cells, or for treating, preventing or ameliorating one or more symptoms of cancer using the compounds of the invention or pharmaceutical compositions, in combination with an additional anti-cancer agent.

In one aspect, the invention provides compounds of the Formula I:

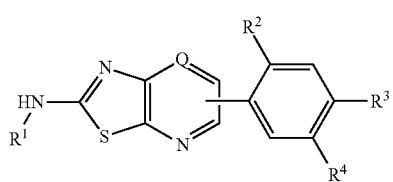

(I)

and pharmaceutically acceptable salts, enantiomers, stereoisomers, rotamers, tautomers, diastereomers, or racemates thereof, wherein Q is CH or N;

$R^1$ is H, C(O)—$C_{3-6}$-cycloalkyl, aryl, heteroaryl, C(O)N(H)-heteroaryl, C(O)-heteroaryl, C(O)-heterocycle, C(O)-aryl, C(O)—$C_{1-6}$-alkyl, $CO_2$—$C_{1-6}$-alkyl, $C_{3-6}$-cycloalkyl, or C(O)—$C_{1-6}$-alkyl-heterocycle, wherein the aryl or heteroaryl groups can be substituted or unsubstituted;

$R^2$ is H, $C_{1-6}$-alkyl, $C_{1-6}$-alkoxy, or halogen;

$R^3$ is H, C(O)—N(H)-aryl, C(O)—N(H)—$C_{1-6}$-alkyl-heterocycle, C(O)—N(H)—$C_{1-6}$-alkyl-heteroaryl, wherein the aryl, heteroaryl or heterocycle groups can be substituted or unsubstituted; and $R^4$ is H, C(O)N(H)-aryl, N(H)C(O)N(H)-aryl, C(O)N(H)—$C_{1-6}$-alkoxy, C(O)—N(H)—$C_{3-6}$-cycloalkyl, C(O)N(H)—$C_{1-6}$-alkyl-heterocycle, $CO_2$—$C_{1-6}$-alkyl, $CO_2$H, C(O)N(H)—$C_{1-6}$-alkyl-heteroaryl, N(H)$CO_2$—$C_{1-6}$-alkyl, $NH_2$, N(H)C(O)aryl, or N(H)C(O)N(H)—$C_{1-6}$-alkyl-heterocycle, wherein the aryl, heteroaryl or heterocycle groups can be substituted or unsubstituted, and wherein one of $R^3$ and $R^4$ is not H.

In one embodiment of Formula I, the aryl, heteroaryl and heterocyclic groups of $R^1$, $R^3$ and $R^4$ can optionally be independently substituted one or more times with OH, $C_{1-6}$-alkyl, $C_{1-6}$-alkoxy, $C_{1-6}$-alkyl-heterocycle, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen;

wherein the substituent aryl, heteroaryl and heterocyclic groups can be further independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen.

In another embodiment, the aryl, heteroaryl and heterocyclic groups of $R^1$, $R^3$ and $R^4$ can optionally be independently substituted one or more times with $C_{1-6}$-alkyl, $C_{1-6}$-alkoxy, $SO_2$-heterocycle, $C_{1-6}$-alkyl-heterocycle, heterocycle, $CF_3$, or heteroaryl;

wherein the substituent heterocycle and heteroaryl groups can be optionally further independently substituted one or more times with OH, $C_{1-6}$-alkyl, $C_{1-6}$-alkoxy, $C_{1-6}$-alkyl-OH, or C(O)—$C_{1-6}$-alkyl.

In still another embodiment of Formula I, $R^1$ is H, C(O)—$C_{3-6}$-cycloalkyl, pyrimidine, C(O)N(H)-piperidine, C(O)-piperidine, C(O)—$C_{1-6}$-alkyl, $C_{3-6}$-cycloalkyl, pyridine, phenyl, C(O)-phenyl, C(O)—$C_{1-6}$-alkyl-piperazine, or C(O)-oxazolidinone, wherein the pyrimidine, piperidine, pyridine, and phenyl groups of $R^1$ can be optionally independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen; and wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl.

In yet another embodiment of Formula I, $R^3$ is H, C(O)—N(H)-phenyl, C(O)—N(H)—$(CH_2)_2$-morpholino, C(O)—N(H)—$C_{1-6}$-alkyl-morpholino, or C(O)—N(H)—$C_{1-6}$-alkyl-imidazole, wherein the morpholino, imidazole, and phenyl groups of $R^3$ can optionally be independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen and wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl.

In another embodiment of Formula I, $R^4$ is H, C(O)N(H)Ph, N(H)C(O)N(H)Ph, C(O)N(H)—$C_{1-6}$-alkoxy, C(O)—N(H)—$C_{3-6}$-cycloalkyl, C(O)N(H)—$C_{1-6}$-alkyl-morpholino, C(O)N(H)$(CH_2)_3$-morpholino, $CO_2$—$C_{1-6}$-alkyl, $CO_2$H, C(O)—N(H)—$C_{1-6}$-alkyl-imidazole, N(H)$CO_2C_{1-6}$-alkyl, $NH_2$, N(H)C(O)Ph, N(H)C(O)N(H)Ph, N(H)C(O)N(H)—$C_{1-6}$-alkyl-morpholino, or N(H)C(O)Ph, wherein the morpholino, imidazole, and phenyl groups of $R^4$ can optionally be independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen, wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl.

In another embodiment, at least one of $R^3$ and $R^4$ are not H. In yet another embodiment, $R^1$ is C(O)—$C_{3-6}$-cycloalkyl, pyrimidine, C(O)N(H)-piperidine, C(O)-piperidine, C(O)$C_{1-6}$-alkyl, H, $C_{3-6}$-cycloalkyl, pyridine, Ph-$SO_2$-piperazine, C(O)-PhCH$_2$-piperazine-$C_{1-6}$-alkyl, C(O)—$C_{1-6}$-alkyl-piperazine, Ph-piperazine-$C_{1-6}$-alkyl, C(O)-oxazolidinone-$C_{1-6}$-alkyl-morpholino, wherein the pyrimidine group is optionally independently substituted one or more times with $C_{1-6}$-alkyl or piperazine, wherein the piperazine is optionally substituted with $C_{1-6}$-alkyl-OH; and wherein C(O)—$C_{1-6}$-alkyl-piperazine is optionally substituted with C(O)$C_{1-6}$-alkyl.

In another embodiment of Formula I, $R^3$ is H, C(O)—N(H)-Ph, C(O)—N(H)—$C_{1-6}$-alkyl-morpholino, C(O)—N(H)—$C_{1-6}$-alkyl-morpholino, or C(O)—N(H)—$C_{1-6}$-alkyl-imidazole, wherein Ph is optionally substituted one or more times with $CF_3$, $C_{1-6}$-alkyl-piperazine-$C_{1-6}$-alkyl, or imidazole-$C_{1-6}$-alkyl. In another embodiment, $R^4$ is H, C(O)N(H)Ph, N(H)C(O)N(H)Ph, C(O)N(H)$C_{1-6}$-alkoxy, C(O)—N(H)—$C_{3-6}$-cycloalkyl, C(O)N(H)—$C_{1-6}$-alkyl-morpholino, $CO_2$—$C_{1-6}$-alkyl, $CO_2$H, N(H)$CO_2$—$C_{1-6}$-alkyl, $NH_2$, or N(H)C(O)N(H)—$C_{1-6}$-alkyl-morpholino, wherein the Ph group is optionally independently substituted one or more times with $CF_3$, $C_{1-6}$-alkyl-piperazine-$C_{1-6}$-alkyl, imidazole-$C_{1-6}$-alkyl, imidazole, tetrazole, pyrazole, piperazine, $C_{1-6}$-alkyl-piperazine-$C_{1-6}$-alkyl, morpholino, $C_{1-6}$-alkyl, $C_{1-6}$-alkoxy, $C_{1-6}$-alkyl-imidazole, $C_{1-6}$-alkyl-morpholino, $C_{1-6}$-alkyl-piperidine-OH, $C_{1-6}$-alkyl-piperazine-$C_{1-6}$-alkyl), imidazole-$C_{1-6}$-alkyl, piperazine-$C_{1-6}$-alkyl-OH, or O-piperidine-$C_{1-6}$-alkyl.

In still another embodiment, $R^1$ is C(O)-cyclopropyl, pyrimidine, C(O)N(H)-piperidine, C(O)-piperidine, C(O)CH$_3$, H, cyclopropyl, pyridine, Ph-$SO_2$-piperazine, C(O)-PhCH$_2$-piperazine-CH$_2$CH$_3$, C(O)—(CH$_2$)$_2$-piperazine, Ph-piperazine-CH$_3$, or C(O)-oxazolidinone-(CH$_2$)$_3$-morpholino, wherein the pyrimidine is substituted with CH$_3$ and piperazine that is optionally substituted with (CH$_2$)$_2$OH, and wherein the piperazine of the C(O)—(CH$_2$)$_2$-piperazine group is optionally substituted with C(O)CH$_3$; $R^2$ is H, CH$_3$, F or Cl; $R^3$ is H, C(O)—N(H)-Ph, C(O)—N(H)—(CH$_2$)$_2$-morpholino, C(O)—N(H)—(CH$_2$)$_3$-morpholino, or C(O)—N(H)—(CH$_2$)$_3$-imidazole, wherein Ph is substituted with $CF_3$ and CH$_2$-piperazine-CH$_2$CH$_3$, or $CF_3$ and imidazole-CH$_3$; and $R^4$ is H, C(O)N(H)Ph-$CF_3$, N(H)C(O)N(H)Ph($CF_3$)(CH$_2$-piperazine-CH$_2$CH$_3$), C(O)N(H)Ph($CF_3$)(CH$_2$-piperazine-CH$_2$CH$_3$), C(O)N(H)OCH$_3$, C(O)N(H)Ph($CF_3$)(imidazole-CH$_3$), C(O)—N(H)-cyclopropyl, C(O)N(H)(CH$_2$)$_2$-morpholino, C(O)N(H)(CH$_2$)$_3$-morpholino, $CO_2$CH$_2$CH$_3$, C(O)N(H)Ph-imidazole, C(O)N(H)Ph-tetrazole, C(O)N(H)Ph-pyrazole, C(O)N(H)Ph($CF_3$)(piperazine), $CO_2$H, C(O)N(H)Ph-CH$_2$-piperazine-CH$_2$CH$_3$, C(O)—N(H)Ph-morpholino, C(O)—N(H)Ph-t-butyl, —C(O)N(H)Ph(OCH$_2$CH$_3$)(morpholino), C(O)N(H)Ph(OCH$_3$)(morpholino), C(O)N(H)Ph(OCH$_3$)$_2$, C(O)—N(H)—(CH$_2$)$_3$-imidazole, C(O)N(H)(CH$_2$)$_2$-morpholino, N(H)CO$_2$-t-butyl, $NH_2$, N(H)C(O)Ph($CF_3$)(CH$_2$-piperidine-OH), N(H)C(O)Ph($CF_3$)(CH$_2$-piperazine-CH$_2$CH$_3$), N(H)C(O)N(H)Ph($CF_3$)(imidazole-CH$_3$), N(H)C(O)N(H)—(CH$_2$)$_2$-morpholino, N(H)C(O)N(H)—(CH$_2$)$_3$-morpholino, N(H)C(O)Ph($CF_3$)(piperazine-(CH$_2$)$_2$OH), or N(H)C(O)Ph($CF_3$)(O-piperidine-CH$_3$).

In another embodiment of the invention, Formula I is represented by the Formula II:

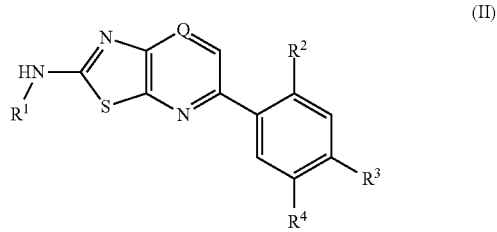

(II)

wherein Q is CH; $R^1$ is C(O)—$C_{3-6}$-cycloalkyl, C(O)N(H)-heteroaryl, C(O)-heteroaryl, C(O)-aryl, C(O)—$C_{1-6}$-alkyl, $CO_2$—$C_{1-6}$-alkyl, $C_{3-6}$-cycloalkyl, or C(O)—$C_{1-6}$-alkyl-heteroaryl; $R^2$ and $R^3$ are H; and $R^4$ is C(O)N(H)-aryl, N(H)C(O)N(H)-aryl, C(O)N(H)—$C_{1-6}$-alkoxy, C(O)—N(H)—$C_{3-6}$-cycloalkyl, C(O)N(H)—$C_{1-6}$-alkyl-heterocycle, $CO_2$—$C_{1-6}$-alkyl, $CO_2$H, C(O)N(H)—$C_{1-6}$-alkyl-heteroaryl, N(H)$CO_2$—$C_{1-6}$-alkyl, $NH_2$, N(H)C(O)aryl, or N(H)C(O)N(H)—$C_{1-6}$-alkyl-heterocycle, wherein the aryl, heteroaryl or heterocycle groups can be substituted or unsubstituted.

In one embodiment of Formula II, $R^1$ is C(O)—$C_{3-6}$-cycloalkyl; Q is C(H); $R^2$ and $R^3$ are H; and $R^4$ is C(O)N(H)Ph, wherein the Ph group is optionally independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen, wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl.

In another embodiment of Formula II, Ph is optionally independently substituted one or more times with $CF_3$, piperazine, $C_{1-6}$-alkyl-piperazine, $C_{1-6}$-alkyl-piperazine-$C_{1-6}$-alkyl, CH$_2$CH$_3$, imidazole, or imidazole-$C_{1-6}$-alkyl.

In still another embodiment of Formula II, $R^1$ is C(O)—$C_{3-6}$-cycloalkyl; Q is C(H); $R^2$ and $R^3$ are H; and $R^4$ is C(O)N(H)Ph, wherein the Ph group is optionally independently substituted one or more times with $CF_3$, $C_{1-6}$-alkyl-piperazine, or imidazole, and wherein the substituent piperazine or imidazole is optionally independently substituted one or more times with $C_{1-6}$-alkyl.

In yet another embodiment of Formula II, Ph is optionally independently substituted one or more times with $CF_3$, piperazine, $C_{1-6}$-alkyl-piperazine, $C_{1-6}$-alkyl-piperazine-$C_{1-6}$-alkyl, CH$_2$CH$_3$, imidazole, or imidazole-$C_{1-6}$-alkyl.

In yet another embodiment, compounds of Formula (III) are included in the present invention:

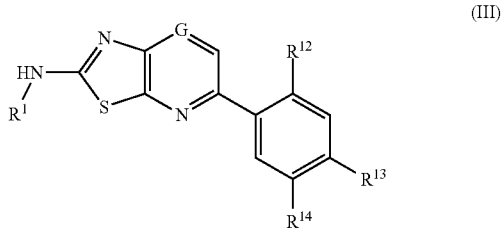

(III)

wherein G is $CR^{10}$ or N;
$R^1$ is H, C(O)—$C_{3-6}$-cycloalkyl, aryl, heteroaryl, C(O)N(H)-heteroaryl, C(O)-heteroaryl, C(O)-heterocycle, C(O)—

NH-heterocycle, C(O)-aryl, C(O)—$C_{1-6}$-alkyl, $CO_2$—$C_{1-6}$-alkyl, $C_{3-6}$-cycloalkyl, or C(O)—$C_{1-6}$-alkyl-heterocycle;

wherein the aryl, heteroaryl and heterocycle groups can optionally be substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen; and wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl.

$R^{10}$ is H or $C_{1-3}$-alkyl;

$R^{12}$ is H, $C_{1-6}$-alkyl, $C_{1-6}$-alkoxy, or halogen;

$R^{13}$ is H, C(O)—N($R^{28}$)-aryl, C(O)—N($R^{29}$)—$C_{1-6}$-alkyl-heterocycle, C(O)—N($R^{30}$)—$C_{1-6}$-alkyl-heteroaryl, wherein the aryl, heteroaryl or heterocycle groups are optionally substituted with one or more of OH, $C_{1-6}$-alkyl, $C_{1-6}$-alkoxy, $C_{1-6}$-alkyl-heterocycle, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen;

wherein the substituent aryl, heteroaryl and heterocyclic groups can be further independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen; and $R^{14}$ is H, C(O)$NR^{15}$-aryl, $NR^{16}$C(O)$NR^{17}$-aryl, C(O)$NR^{18}$—$C_{1-6}$-alkoxy, C(O)—$NR^{19}$—$C_{3-6}$-cycloalkyl, C(O)$NR^{20}$—$C_{1-6}$-alkyl-heterocycle, $CO_2$—$C_{1-6}$-alkyl, $CO_2H$, C(O)$NR^{21}$—$C_{1-6}$-alkyl-heterocycle, $NR^{22}CO_2$—$C_{1-6}$-alkyl, $NR^{23}R^{24}$, $NR^{25}$C(O)aryl or $NR^{26}$C(O)$NR^{27}$—$C_{1-6}$-alkyl-heterocycle, wherein the aryl, heteroaryl or heterocycle groups are optionally substituted with one or more of OH, $C_{1-6}$-alkyl, $C_{1-6}$-alkoxy, $C_{1-6}$-alkyl-heterocycle, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen;

wherein the substituent aryl, heteroaryl and heterocyclic groups can be further independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen, and wherein one of $R^{13}$ and $R^{14}$ is not H;

$R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are independently $C_{1-6}$alkyl, halogen, or H.

In one embodiment of Formula III, $R^1$ is H, C(O)—$C_{3-6}$-cycloalkyl, pyrimidine, C(O)N(H)-piperidine, C(O)-piperidine, C(O)—$C_{1-6}$-alkyl, $C_{3-6}$-cycloalkyl, pyridine, phenyl, C(O)-phenyl, C(O)—$C_{1-6}$-alkyl-piperazine, or C(O)-oxazolidinone, wherein the pyrimidine, piperidine, pyridine, and phenyl groups of $R^1$ can be optionally independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen; and wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl.

In another embodiment of Formula III, $R^{13}$ is H, C(O)—N($R^{28}$)-phenyl, C(O)—N($R^{29}$)—$(CH_2)_2$-morpholino, C(O)—N($R^{30}$)—$C_{1-6}$-alkyl-morpholino, or C(O)—N($R^{30}$)—$C_{1-6}$-alkyl-imidazole, wherein the morpholino, imidazole, and phenyl groups of $R^{13}$ can optionally be independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen and wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl.

In still another embodiment of Formula III, $R^{14}$ is H, C(O)N($R^{15}$)Ph, N($R^{16}$)C(O)N($R^{17}$)Ph, C(O)N($R^{18}$)—$C_{1-6}$-alkoxy, C(O)—N($R^{19}$)—$C_{3-6}$-cycloalkyl, C(O)N($R^{20}$)—$C_{1-6}$-alkyl-morpholino, C(O)N($R^{20}$)$(CH_2)_3$-morpholino, $CO_2$—$C_{1-6}$-alkyl, $CO_2H$, C(O)—N($R^{21}$)—$C_{1-6}$-alkyl-imidazole, N($R^{22}$)$CO_2C_{1-6}$-alkyl, $NR^{23}R^{24}$, N($R^{25}$)C(O)Ph, $NR^{26}$C(O)$NR^{27}$—$C_{1-6}$-alkyl-morpholino, wherein the morpholino, imidazole, and phenyl groups of $R^{14}$ can optionally be independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen, wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl.

In yet another embodiment of Formula III, at least one of $R^{13}$ and $R^{14}$ are not H.

In yet another embodiment, $R^1$ is C(O)—$C_{3-6}$-cycloalkyl, pyrimidine, C(O)N(H)-piperidine, C(O)-piperidine, C(O)$C_{1-6}$-alkyl, H, $C_{3-6}$-cycloalkyl, pyridine, Ph-$SO_2$-piperazine, C(O)-PhCH$_2$-piperazine-$C_{1-6}$-alkyl, C(O)—$C_{1-6}$-alkyl-piperazine, Ph-piperazine-$C_{1-6}$-alkyl, C(O)-oxazolidinone-$C_{1-6}$-alkyl-morpholino, wherein the pyrimidine group is optionally independently substituted one or more times with $C_{1-6}$-alkyl or piperazine, wherein the piperazine is optionally substituted with $C_{1-6}$-alkyl-OH; and wherein C(O)—$C_{1-6}$-alkyl-piperazine is optionally substituted with C(O)$C_{1-6}$-alkyl.

In another embodiment of Formula III, $R^{13}$ is H, C(O)—N(H)-Ph, C(O)—N(H)—$C_{1-6}$-alkyl-morpholino, C(O)—N(H)—$C_{1-6}$-alkyl-morpholino, or C(O)—N(H)—$C_{1-6}$-alkyl-imidazole, wherein Ph is optionally substituted one or more times with $CF_3$, $C_{1-6}$-alkyl-piperazine-$C_{1-6}$-alkyl, or imidazole-$C_{1-6}$-alkyl. In another embodiment, $R^{14}$ is H, C(O)N($R^{15}$)Ph, N($R^{16}$)C(O)N($R^{17}$)Ph, C(O)N($R^{18}$)—$C_{1-6}$-alkoxy, C(O)—N($R^{19}$)—$C_{3-6}$-cycloalkyl, C(O)N($R^{20}$)—$C_{1-6}$-alkyl-morpholino, $CO_2$—$C_{1-6}$-alkyl, $CO_2H$, N($R^{22}$)$CO_2C_{1-6}$-alkyl, $NR^{23}R^{24}$, N($R^{25}$)C(O)Ph, $NR^{26}$C(O)$NR^{27}$—$C_{1-6}$-alkyl-morpholino, wherein the Ph group is optionally independently substituted one or more times with $CF_3$, $C_{1-6}$-alkyl-piperazine-$C_{1-6}$-alkyl, imidazole-$C_{1-6}$-alkyl, imidazole, tetrazole, pyrazole, piperazine, $C_{1-6}$-alkyl-piperazine-$C_{1-6}$-alkyl, morpholino, $C_{1-6}$-alkyl, $C_{1-6}$-alkoxy, $C_{1-6}$-alkyl-imidazole, $C_{1-6}$-alkyl-morpholino, $C_{1-6}$-alkyl-piperidine-OH, $C_{1-6}$-alkyl-piperazine-$C_{1-6}$-alkyl), imidazole-$C_{1-6}$-alkyl, piperazine-$C_{1-6}$-alkyl-OH, or O-piperidine-$C_{1-6}$-alkyl.

In still another embodiment of Formula III, $R^1$ is C(O)-cyclopropyl, pyrimidine, C(O)N(H)-piperidine, C(O)-piperidine, C(O)CH$_3$, H, cyclopropyl, pyridine, Ph-$SO_2$-piperazine, C(O)-PhCH$_2$-piperazine-CH$_2$CH$_3$, C(O)—$(CH_2)_2$-piperazine, Ph-piperazine-CH$_3$, or C(O)-oxazolidinone-$(CH_2)_3$-morpholino, wherein the pyrimidine is substituted with CH₃ and piperazine that is optionally substituted with (CH₂)₂OH, and wherein the piperazine of the C(O)—(CH₂)₂-piperazine group is optionally substituted with C(O)CH₃; R¹² is H, CH₃, F or Cl; R¹³ is H, C(O)—N(H)-Ph, C(O)—N(H)—(CH₂)₂-morpholino, C(O)—N(H)—(CH₂)₃-morpholino, or C(O)—N(H)—(CH₂)₃-imidazole, wherein Ph is substituted with CF₃ and CH₂-piperazine-CH₂CH₃, or CF₃ and imidazole-CH₃; and R¹⁴ is H, C(O)N(H)Ph-CF₃, N(H)C(O)N(H)Ph(CF₃)(CH₂-piperazine-CH₂CH₃), C(O)N(H)Ph(CF₃)(CH₂-piperazine-CH₂CH₃), C(O)N(H)OCH₃, C(O)N(H)Ph(CF₃)(imidazole-CH₃), C(O)—N(H)-cyclopropyl, C(O)N(H)(CH₂)₂-morpholino, C(O)N(H)(CH₂)₃-morpholino, CO₂CH₂CH₃, C(O)N(H)Ph-imidazole, C(O)N(H)Ph-tetrazole, C(O)N(H)Ph-pyrazole, C(O)N(H)Ph(CF₃)(piperazine), CO₂H, C(O)N(H)Ph-CH₂-piperazine-CH₂CH₃, C(O)—N(H)Ph-morpholino, C(O)—N(H)Ph-t-butyl, —C(O)N(H)Ph(OCH₂CH₃)(morpholino), C(O)N(H)Ph(OCH₃)(morpholino), C(O)N(H)Ph(OCH₃)₂, C(O)—N(H)—(CH₂)₃-imidazole, C(O)N(H)(CH₂)₂-morpholino, N(H)CO₂-t-butyl, NH₂, N(H)C(O)Ph(CF₃)(CH₂-piperidine-OH), N(H)C(O)Ph(CF₃)(CH₂-piperazine-CH₂CH₃), N(H)C(O)N(H)Ph(CF₃)(imidazole-CH₃), N(H)C(O)N(H)—(CH₂)₂-morpholino, N(H)C(O)N(H)—(CH₂)₃-morpholino, N(H)C(O)Ph(CF₃)(piperazine-(CH₂)₂OH), or N(H)C(O)Ph(CF₃)(O-piperidine-CH₃).

Preferred embodiments of Formula I are equivalent to preferred embodiments of Formula III (including pharmaceutically acceptable salts thereof, as well as enantiomers, stereoisomers, rotamers, tautomers, diastereomers, atropisomers or racemates thereof) and are shown below in Table A and are also considered to be "compounds of the invention." The compounds of the invention are also referred to herein as "protein kinase inhibitors."

TABLE A

| Compound Number | Structure | Physical Data ¹H NMR 600 MHz and/or MS (m/z) |
|---|---|---|
| 1 | 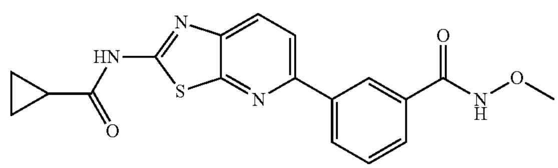 [SMILES: CONC(=O)c1cccc(-c2ccc3nc(NC(=O)C4CC4)sc3n2)c1] | ¹H NMR 600 MHz (CDCl₃) δ 12.80 (s, 1H), 11.87 (s, 1H), 8.45 (s, 1H), 8.26 (d, J = 3.6 Hz, 1H), 8.17 (d, J = 7.8 Hz, 1H), 7.82 (d, J = 7.8 Hz, 1H), 7.57 (t, 1H), 3.71 (s, 3H), 2.01 (m, 1H), 0.96 (m, 4H), MS m/z: 369.23 (M + 1). |
| 2 | 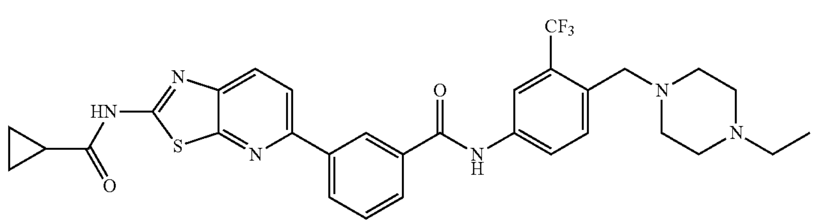 [SMILES: CCN1CCN(Cc2ccc(NC(=O)c3cccc(-c4ccc5nc(NC(=O)C6CC6)sc5n4)c3)cc2C(F)(F)F)CC1] | ¹H NMR 600 MHz (DMSO-d₆) δ 12.82 (s, 1H), 10.65 (s, 1H), 8.67 (s, 1H), 8.35 (d, J = 7.8 Hz, 1H), 8.22 (m, 2H), 8.17 (d, J = 8.4 Hz, 1H), 8.07 (d, J = 8.4 Hz, 1H), 8.01 (d, J = 7.2 Hz, 1H), 7.72 (d, J = 8.4 Hz, 1H), 7.67 (t, 1H), 3.56 (m, 2H), 3.29 (m, 2H), 2.41 (m, 8H), 2.03 (m, 1H), 0.99 (m, 7H), MS m/z: 609.28 (M + 1). |
| 3 | 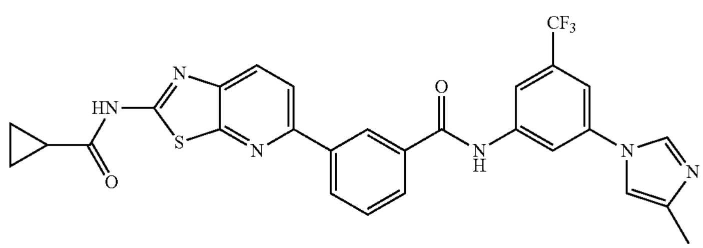 [SMILES: Cc1cn(-c2cc(NC(=O)c3cccc(-c4ccc5nc(NC(=O)C6CC6)sc5n4)c3)cc(C(F)(F)F)c2)cn1] | ¹H NMR 600 MHz (DMSO-d₆) δ 12.83 (s, 1H), 10.84 (s, 1H), 8.71 (s, 1H), 8.37 (d, J = 7.2 Hz, 1H), 8.31 (s, 1H), 8.22 (m, 2H), 8.18 (d, J = 8.4 Hz, 1H), 8.04 (d, J = 7.8 Hz, 1H), 7.74 (s, 1H), 7.69 (t, 1H), 7.49 (s, 1H), 3.29 (s, 3H), 2.17 (s, 3H), 2.03 (m, 1H), 0.99 (m, 4H), MS m/z: 563.18 (M + 1). |

TABLE A-continued

| Compound Number | Structure | Physical Data ¹H NMR 600 MHz and/or MS (m/z) |
|---|---|---|
| 4 | 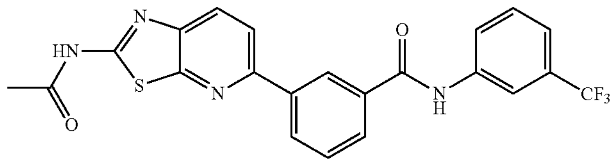 [SMILES: CC(=O)Nc1nc2ccc(-c3cccc(C(=O)Nc4cccc(C(F)(F)F)c4)c3)nc2s1] | ¹H NMR 600 MHz (DMSO-d$_6$) δ 12.52 (s, 1H), 10.69 (s, 1H), 8.68 (s, 1H), 8.57 (d, J = 7.8 Hz, 1H), 8.26 (s, 1H), 8.21 (d, J = 7.8 Hz, 1H), 8.17 (d, J = 9.0 Hz, 1H), 8.09 (d, J = 8.4 Hz, 1H), 8.02 (d, J = 7.8 Hz, 1H), 7.67 (t, J = 7.2 Hz, 1H), 7.61 (t, J = 7.8 Hz, 1H), 7.46 (d, J = 9.0 Hz, 1H), 2.23 (s, 3H), MS m/z: 457.17 (M + 1). |
| 5 | 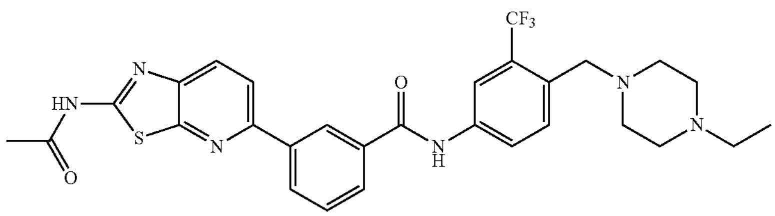 [SMILES: CCN1CCN(Cc2ccc(NC(=O)c3cccc(-c4ccc5nc(NC(C)=O)sc5n4)c3)cc2C(F)(F)F)CC1] | ¹H NMR 600 MHz (DMSO-d$_6$) δ 12.53 (s, 1H), 10.69 (s, 1H), 8.68 (s, 1H), 8.35 (d, J =7.8 Hz, 1H), 8.22 (m, 2H), 8.17 (d, J = 9.0 Hz, 1H), 8.13 (d, J = 7.8 Hz, 1H), 8.02 (d, J = 7.2 Hz, 1H), 7.73 (d, J = 7.8 Hz, 1H), 7.69 (m, 1H), 3.68 (s, 2H), 3.46 (m, 2H), 3.14 (m, 2H), 2.98 (m, 2H), 2.92 (m, 2H), 2.40 (m, 2H), , 2.23 (s, 3H), 1.26 (m, 3H), MS m/z: 583.39 (M + 1). |
| 6 | 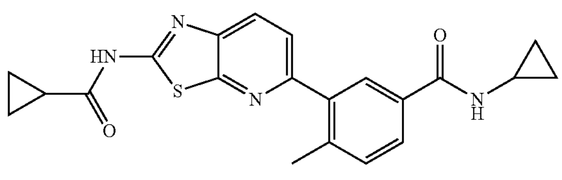 [SMILES: Cc1ccc(C(=O)NC2CC2)cc1-c1ccc2nc(NC(=O)C3CC3)sc2n1] | ¹H NMR 600 MHz (CDCl$_3$) δ 10.51 (s, 1H), 7.97 (s, 1H), 7.72 (d, J = 8.4 Hz, 1H), 7.58 (d, J = 7.8 Hz, 1H), 7.28 (d, J = 7.8 Hz, 1H), 7.24 (d, J = 8.4 Hz, 1H), 6.34 (s, 1H), 2.64 (m, 1H), 1.77 (m, 1H), 1.39 (m, 4H), 0.84 (m, 4H), MS m/z: 393.27 (M + 1). |
| 7 | 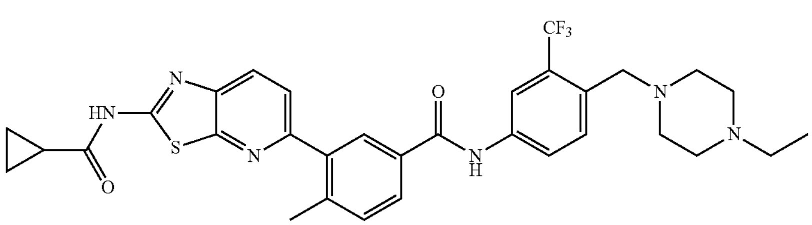 [SMILES: CCN1CCN(Cc2ccc(NC(=O)c3ccc(C)c(-c4ccc5nc(NC(=O)C6CC6)sc5n4)c3)cc2C(F)(F)F)CC1] | ¹H NMR 600 MHz (DMSO-d$_6$) δ 12.82 (s, 1H), 10.53 (s, 1H), 8.20 (m, 2H), 8.09 (m, 2H), 7.95 (d, J = 8.4 Hz, 1H), 7.70 (m, 2H), 7.51 (d, J = 6.6 Hz, 1H), 3.68 (s, 2H), 3.45 (m, 2H), 3.13 (m, 2H), 2.97 (m, 4H), 2.42 (m, 5H), 2.03 (m, 1H), 1.89 (m, 3H), 0.97 (m, 4H), MS m/z: 623.33 (M + 1). |

TABLE A-continued

| Compound Number | Structure | Physical Data $^1$H NMR 600 MHz and/or MS (m/z) |
|---|---|---|
| 8 | 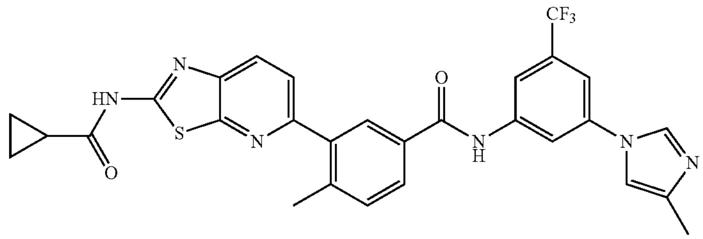 [SMILES: Cc1cn(-c2cc(NC(=O)c3ccc(C)c(-c4ccc5nc(NC(=O)C6CC6)sc5n4)c3)cc(C(F)(F)F)c2)cn1] | $^1$H NMR 600 MHz (DMSO-d$_6$) δ 12.83 (s, 1H), 10.87 (s, 1H), 9.58 (s, 1H), 8.57 (s, 1H), 8.24 (s, 1H), 8.21 (d, J = 7.8 Hz, 1H), 8.13 (d, J = 1.8 Hz, 1H), 8.02 (s, 1H), 7.98 (dd, J = 1.2 Hz, J = 7.8 Hz, 1H), 7.90 (s, 1H), 7.71 (d, J = 8.4 Hz, 1H), 7.54 (d, J = 7.8 Hz, 1H), 2.43 (s, 3H), 2.34 (s, 3H), 2.04 (m, 1H), 0.99 (m, 4H), MS m/z: 577.26 (M + 1). |
| 9 | 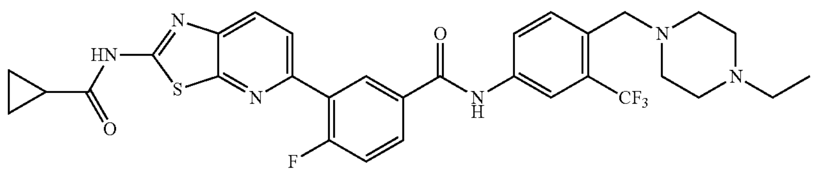 [SMILES: CCN1CCN(Cc2ccc(NC(=O)c3ccc(F)c(-c4ccc5nc(NC(=O)C6CC6)sc5n4)c3)cc2C(F)(F)F)CC1] | $^1$H NMR 600 MHz (DMSO-d$_6$) δ 12.86 (s, 1H), 10.70 (s, 1H), 8.60 (dd, J = 2.4 Hz, J = 7.2 Hz, 1H), 8.22 (m, 2H), 8.10 (m, 2H), 7.94 (d, J = 6.6 Hz, 1H), 7.72 (d, J = 8.4 Hz, 1H), 7.55 (t, 1H), 3.72 (s, 2H), 3.46 (m, 2H), 3.15 (q, 2H), 2.98 (m, 4H), 2.43 (m, 2H), 2.06 (m, 1H), 1.42 (m, 3H), 1.02 (m, 4H), MS m/z: 627.41 (M + 1). |
| 10 | 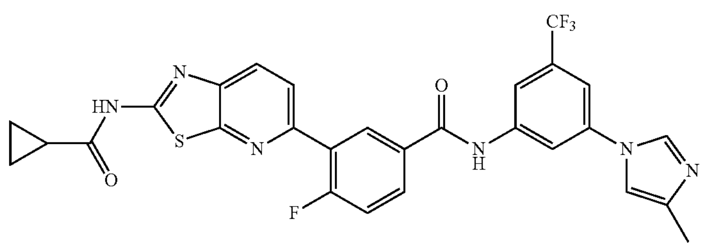 | $^1$H NMR 600 MHz (DMSO-d$_6$) δ 12.89 (s, 1H), 11.02 (s, 1H), 9.60 (s, 1H), 8.65 (d, J = 5.4 Hz, 1H), 8.55 (s, 1H), 8.25 (s, 1H), 8.23 (d, J = 7.8 Hz, 1H), 8.13 (m, 1H), 8.03 (m, 1H), 7.95 (m, 2H), 7.59 (t, 1H), 2.34 (s, 3H), 2.04 (m, 1H), 0.99 (m, 4H), MS m/z: 581.14 (M + 1). |
| 11 | 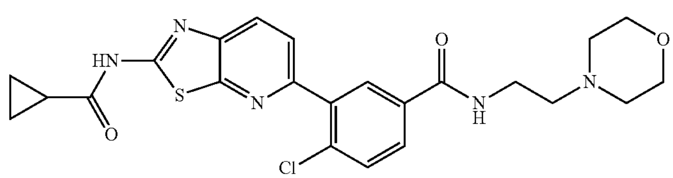 [SMILES: O=C(NCCN1CCOCC1)c1ccc(Cl)c(-c2ccc3nc(NC(=O)C4CC4)sc3n2)c1] | $^1$H NMR 600 MHz (DMSO-d$_6$) δ 12.88 (s, 1H), 8.89 (t, 1H), 8.22 (d, J = 9.0 Hz, 1H), 8.11 (d, J = 2.4 Hz, 1H), 7.93 (dd, J = 2.4 Hz, J = 8.4 Hz, 1H), 7.83 (d, J = 8.4 Hz, 1H), 7.74 (d, J = 8.4 Hz, 1H), 3.69 (m, 4H), 3.63 (m, 4H), 3.52 (m, 2H), 3.11 (m, 2H), 2.04 (m, 1H), 0.98 (m, 4H), MS m/z: 486.24 (M + 1). |

TABLE A-continued

| Compound Number | Structure | Physical Data ¹H NMR 600 MHz and/or MS (m/z) |
|---|---|---|
| 12 | 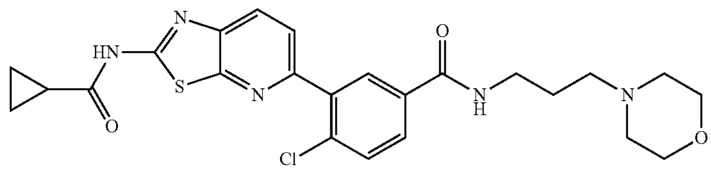 [SMILES: O=C(NCCCN1CCOCC1)c1ccc(Cl)c(-c2ccc3nc(NC(=O)C4CC4)sc3n2)c1] | ¹H NMR 600 MHz (DMSO-d₆) δ 12.87 (s, 1H), 8.79 (t, 1H), 8.21 (d, J = 8.4 Hz, 1H), 8.09 (s, 1H), 7.92 (dd, J = 2.4 Hz, J = 8.4 Hz, 1H), 7.78 (d, J = 8.4 Hz, 1H), 7.72 (d, J = 8.4 Hz, 1H), 3.96 (m, 2H), 3.63 (m, 2H), 3.42 (m, 2H), 3.14 (m, 2H), 3.07 (m, 4H), 2.88 (m, 2H), 2.03 (m, 1H), 0.98 (m, 4H), MS m/z: 500.24 (M + 1). |
| 13 | 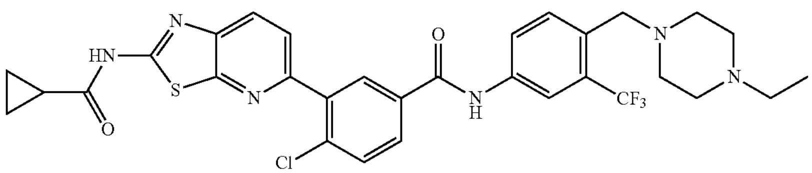 [SMILES: CCN1CCN(Cc2ccc(NC(=O)c3ccc(Cl)c(-c4ccc5nc(NC(=O)C6CC6)sc5n4)c3)cc2C(F)(F)F)CC1] | MS m/z: 643.30 (M + 1). |
| 14 | 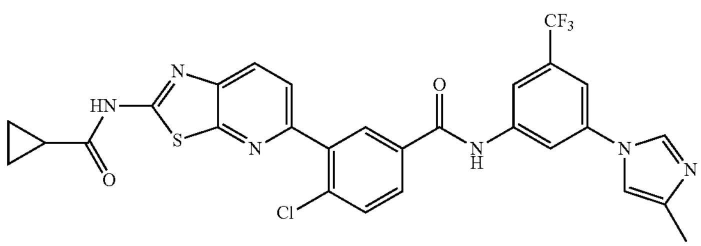 [SMILES: Cc1cn(-c2cc(NC(=O)c3ccc(Cl)c(-c4ccc5nc(NC(=O)C6CC6)sc5n4)c3)cc(C(F)(F)F)c2)cn1] | MS m/z: 597.12 (M + 1). |
| 15 | 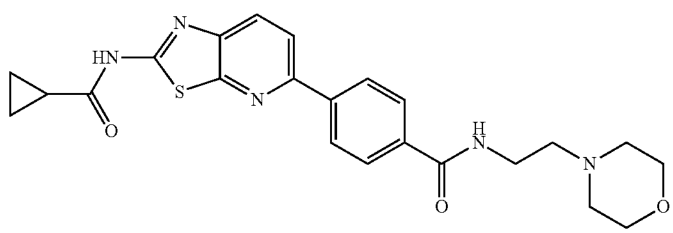 [SMILES: O=C(NCCN1CCOCC1)c1ccc(-c2ccc3nc(NC(=O)C4CC4)sc3n2)cc1] | MS m/z: 452.30 (M + 1). |
| 16 | 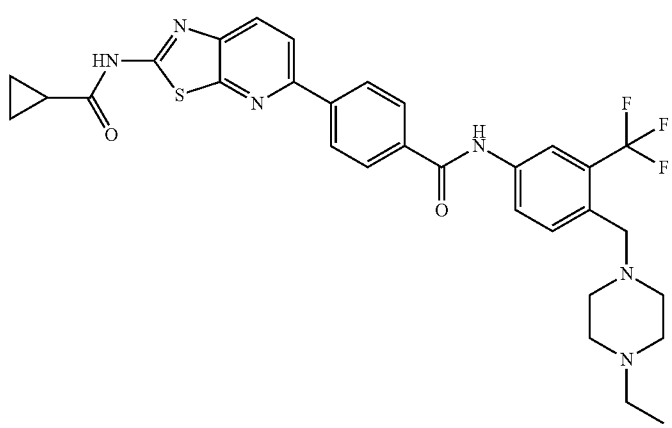 [SMILES: CCN1CCN(Cc2ccc(NC(=O)c3ccc(-c4ccc5nc(NC(=O)C6CC6)sc5n4)cc3)cc2C(F)(F)F)CC1] | MS m/z: 609.32 (M + 1). |

TABLE A-continued

| Compound Number | Structure | Physical Data $^1$H NMR 600 MHz and/or MS (m/z) |
|---|---|---|
| 17 | 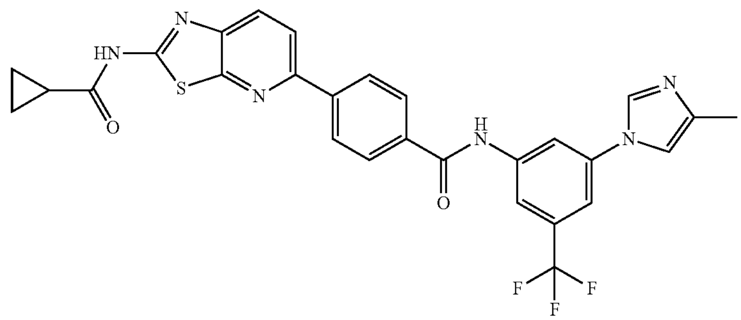 [SMILES: Cc1cn(-c2cc(NC(=O)c3ccc(-c4ccc5nc(NC(=O)C6CC6)sc5n4)cc3)cc(C(F)(F)F)c2)cn1] | MS m/z: 563.26 (M + 1). |
| 18 | 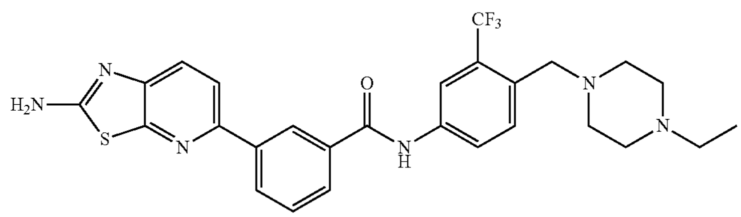 [SMILES: CCN1CCN(Cc2ccc(NC(=O)c3cccc(-c4ccc5nc(N)sc5n4)c3)cc2C(F)(F)F)CC1] | $^1$H NMR 600 MHz (DMSO-d$_6$) δ 10.67 (s, 1H), 9.45 (bs, 2H), 8.59 (s, 1H), 8.24 (m, 2H), 8.12 (d, J = 8.4 Hz, 1H), 7.96 (m, 2H), 7.73 (d, J = 8.4 Hz, 2H), 7.69 (t, 1H), 3.71 (s, 2H), 3.47 (m, 2H), 3.14 (m, 2H), 2.98 (m, 4H), 2.42 (m, 2H), 1.21 (m, 3H), MS m/z: 541.30 (M + 1). |
| 19 | 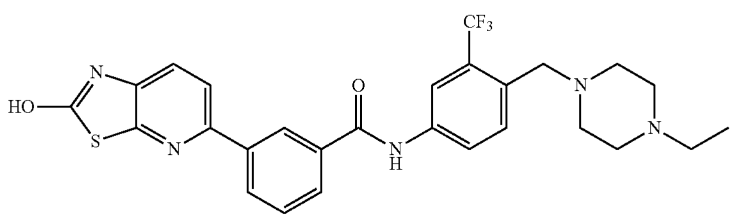 [SMILES: CCN1CCN(Cc2ccc(NC(=O)c3cccc(-c4ccc5nc(O)sc5n4)c3)cc2C(F)(F)F)CC1] | $^1$H NMR 600 MHz (DMSO-d$_6$) δ 12.26 (s, 1H), 10.68 (s, 1H), 8.58 (s, 1H), 8.24 (m, 2H), 8.12 (d, J = 8.4 Hz, 1H), 7.99 (m, 2H), 7.72 (d, J = 8.4 Hz, 1H), 7.64 (t, 1H), 7.57 (d, J = 8.4 Hz, 1H), 3.69 (s, 2H), 3.46 (m, 2H), 3.14 (m, 2H), 2.98 (m, 2H), 2.94 (m, 2H), 2.42 (m, 2H), 1.19 (m, 3H), MS m/z: 542.16 (M + 1). |
| 20 | 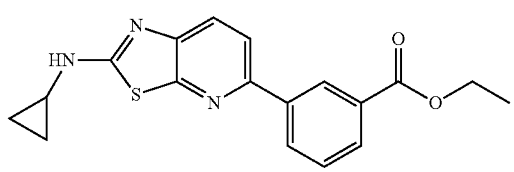 [SMILES: CCOC(=O)c1cccc(-c2ccc3nc(NC4CC4)sc3n2)c1] | $^1$H NMR 600 MHz (CDCl$_3$) δ 8.58 (s, 1H), 8.16 (d, J = 7.2 Hz, 1H), 7.99 (d, J = 7.8 Hz, 1H), 7.73 (d, J = 8.4 Hz, 1H), 7.69 (d, J = 9.0 Hz, 1H), 7.47 (t, J = 7.8 Hz, 1H), 4.37 (q, 2H), 2.73 (m, 1H), 1.36 (t, J = 7.2 Hz, 2H), 0.87 (m, 2H), 0.73 (m, 2H), MS m/z: 340.19 (M + 1). |

TABLE A-continued

| Compound Number | Structure | Physical Data ¹H NMR 600 MHz and/or MS (m/z) |
|---|---|---|
| 21 | 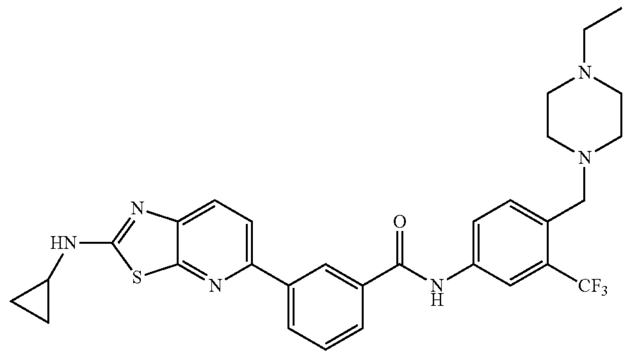 [SMILES: CCN1CCN(Cc2ccc(NC(=O)c3cccc(-c4ccc5nc(NC6CC6)sc5n4)c3)cc2C(F)(F)F)CC1] | MS m/z: 581.32 (M + 1). |
| 22 | 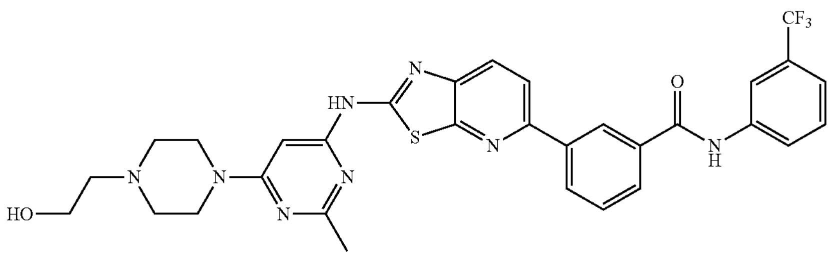 [SMILES: Cc1nc(Nc2nc3ccc(-c4cccc(C(=O)Nc5cccc(C(F)(F)F)c5)c4)nc3s2)cc(N2CCN(CCO)CC2)n1] | MS m/z: 635.37 (M + 1). |
| 23 | 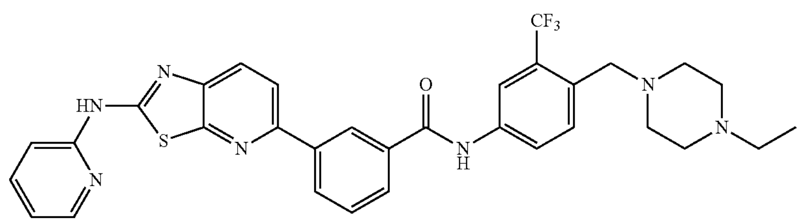 [SMILES: CCN1CCN(Cc2ccc(NC(=O)c3cccc(-c4ccc5nc(Nc6ccccn6)sc5n4)c3)cc2C(F)(F)F)CC1] | ¹H NMR 600 MHz (DMSO-$d_6$) δ 11.80 (s, 1H), 10.71 (s, 1H), 8.67 (s, 1H), 8.38 (m, 1H), 8.34 (d, J = 6.6 Hz, 1H), 8.25 (s, 1H), 8.14 (d, J = 7.2 Hz, 1H), 8.11 (d, J = 8.4 Hz, 1H), 8.06 (d, J = 8.4 Hz, 1H), 7.99 (d, J = 7.2 Hz, 1H), 7.80 (m, 1H), 7.74 (m, J = 7.8 Hz, 1H), 7.67 (t, 1H), 7.22 (d, J = 7.8 Hz, 1H), 7.06 (m, 1H), 3.70 (s, 2H), 3.47 (m, 2H), 3.14 (m, 2H), 2.96 (m, 4H), 2.42 (m, 2H), 2.23 (s, 3H), 1.20 (m, 3H), MS m/z: 618.32 (M + 1). |
| 24 | 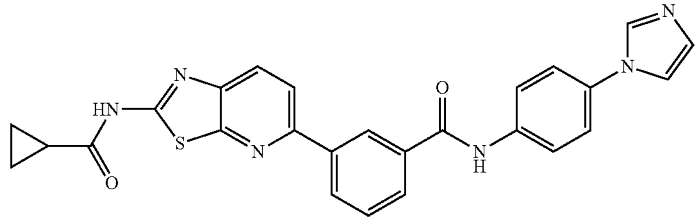 [SMILES: O=C(Nc1ccc(-n2ccnc2)cc1)c1cccc(-c2ccc3nc(NC(=O)C4CC4)sc3n2)c1] | ¹H NMR 600 MHz (DMSO-$d_6$) δ 12.84 (s, 1H), 10.72 (s, 1H), 9.63 (s, 1H), 8.69 (s, 1H), 8.35 (d, J = 7.8 Hz, 1H), 8.26 (s, 1H), 8.21 (d, J = 8.4 Hz, 1H), 8.17 (d, J = 9.0 Hz, 1H), 8.05 (d, J = 8.4 Hz, 2H), 8.03 (d, J = 7.8 Hz, 1H), 7.89 (s, 1H), 7.81 (d, J = 9.0 Hz, 2H), 2.48 (s, 3H), 2.03 (m, 1H), 0.97 (m, 4H), MS m/z: 481.24 (M + 1). |

TABLE A-continued

| Compound Number | Structure | Physical Data ¹H NMR 600 MHz and/or MS (m/z) |
|---|---|---|
| 25 | 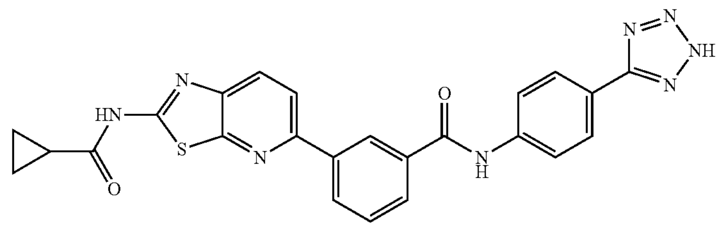 [SMILES: O=C(Nc1ccc(-c2nn[nH]n2)cc1)c1cccc(-c2ccc3nc(NC(=O)C4CC4)sc3n2)c1] | ¹H NMR 600 MHz (DMSO-d$_6$) δ 12.83 (s, 1H), 10.67 (s, 1H), 8.70 (s, 1H), 8.62 (s, 1H), 8.34 (m, 1H), 8.19 (m, 3H), 8.04 (m, 3H), 7.77 (d, J = 7.2 Hz, 1H), 7.68 (t, 1H), 7.61 (m, 1H), 2.03 (m, 1H), 0.97 (m, 4H), MS m/z: 483.22 (M + 1). |
| 26 | 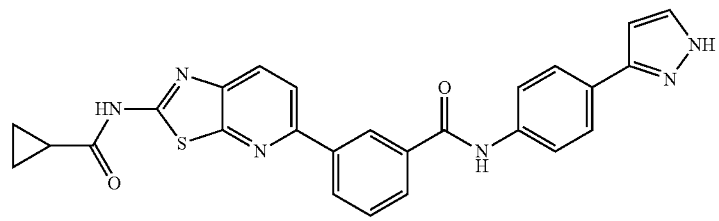 [SMILES: O=C(Nc1ccc(-c2cc[nH]n2)cc1)c1cccc(-c2ccc3nc(NC(=O)C4CC4)sc3n2)c1] | ¹H NMR 600 MHz (DMSO-d$_6$) δ 12.82 (s, 1H), 10.46 (s, 1H), 8.70 (s, 1H), 8.69 (s, 1H), 8.34 (d, J = 8.4 Hz, 1H), 8.24 (s, 1H), 8.19 (m, 2H), 8.03 (d, J = 7.2 Hz, 1H), 7.78 (d, J = 8.4 Hz, 1H), 7.74 (m, 1H), 7.67 (t, 1H), 7.55 (d, J = 7.8 Hz, 1H), 7.04 (t, 1H), 6.60 (m, 1H), 2.03 (m, 1H), 0.97 (m, 4H), MS m/z: 481.17 (M + 1). |
| 27 | 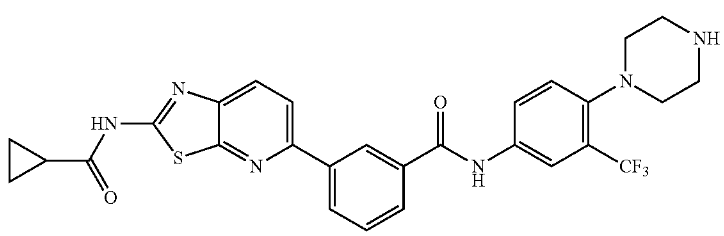 [SMILES: O=C(Nc1ccc(N2CCNCC2)c(C(F)(F)F)c1)c1cccc(-c2ccc3nc(NC(=O)C4CC4)sc3n2)c1] | ¹H NMR 600 MHz (DMSO-d$_6$) δ 12.83 (s, 1H), 10.67 (s, 1H), 8.81 (m, 2H), 8.67 (s, 1H), 8.34 (d, J = 7.2 Hz, 1H), 8.02 (m, 2H), 8.13 (m, 2H), 8.01 (d, J = 7.8 Hz, 1H), 7.67 (t, 1H), 7.58 (d, J = 8.4 Hz, 1H), 3.20 (m, 4H), 3.04 (m, 4H), 2.04 (m, 1H), 0.97 (m, 4H), MS m/z: 567.22 (M + 1). |
| 28 | 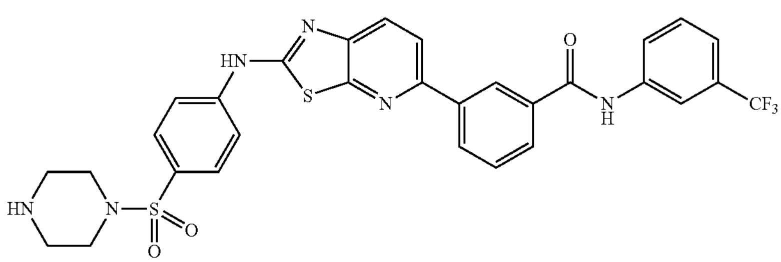 [SMILES: O=C(Nc1cccc(C(F)(F)F)c1)c1cccc(-c2ccc3nc(Nc4ccc(S(=O)(=O)N5CCNCC5)cc4)sc3n2)c1] | ¹H NMR 600 MHz (DMSO-d$_6$) δ 11.37 (s, 1H), 10.69 (s, 1H), 8.67 (m, 3H), 8.32 (d, J = 7.2 Hz, 1H), 8.27 (s, 1H), 8.12 (m, 3H), 8.09 (d, J = 7.4 Hz, 2H), 8.02 (d, J = 7.8 Hz, 1H), 7.81 (d, J = 8.4 Hz, 2H), 7.62 (m, 1H), 7.61 (t, J = 7.8 Hz, 1H), 7.47 (d, J = 7.2 Hz, 1H), 3.19 (m, 4H), 3.09 (m, 4H), MS m/z: 639.23 (M + 1). |

TABLE A-continued

| Compound Number | Structure | Physical Data ¹H NMR 600 MHz and/or MS (m/z) |
|---|---|---|
| 29 | 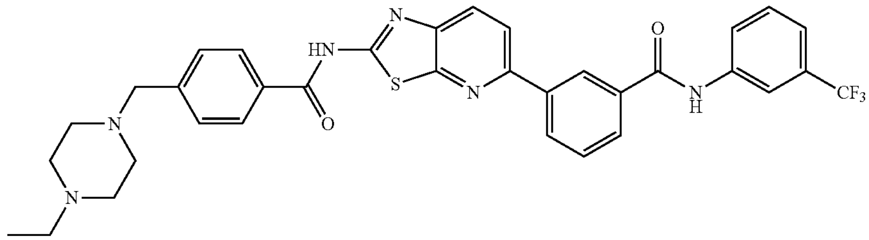 [SMILES: CCN1CCN(Cc2ccc(C(=O)Nc3nc4ccc(-c5cccc(C(=O)Nc6cccc(C(F)(F)F)c6)c5)nc4s3)cc2)CC1] | ¹H NMR 600 MHz (DMSO-d$_6$) δ 13.08 (s, 1H), 10.72 (s, 1H), 8.71 (s, 1H), 8.38 (d, J = 7.2 Hz, 1H), 8.27 (m, 2H), 8.22 (d, J = 8.4 Hz, 1H), 8.17 (d, J = 7.88 Hz, 2H), 8.09 (d, J = 7.8 Hz, 1H), 8.04 (d, J = 7.8 Hz, 1H), 7.69 (m, 1H), 7.61 (t, J = 7.8 Hz, 1H), 7.57 (d, J = 7.2 Hz, 2H), 7.47 (d, J = 7.8 Hz, 1H), 3.82 (s, 2H), 3.47 (m, 2H), 3.12 (m, 2H), 3.05 (m, 4H), 2.52 (m, 2H), 1.92 (m, 3H), MS m/z: 645.29 (M + 1). |
| 30 | 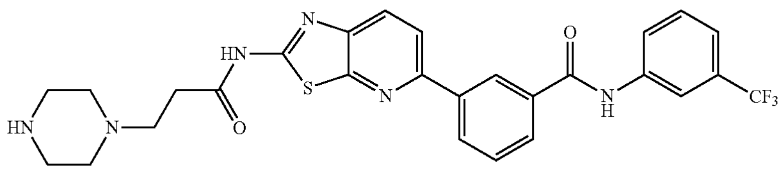 [SMILES: O=C(CCN1CCNCC1)Nc1nc2ccc(-c3cccc(C(=O)Nc4cccc(C(F)(F)F)c4)c3)nc2s1] | ¹H NMR 600 MHz (DMSO-d$_6$) δ 12.78 (s, 1H), 10.71 (s, 1H), 9.04 (bs, 1H), 8.69 (s, 1H), 8.36 (d, J = 8.4 Hz, 1H), 8.27 (s, 1H), 8.25 (d, J = 9.0 Hz, 1H), 8.20 (d, J = 9.0 Hz, 1H), 8.09 (d, J = 8.4 Hz, 1H), 8.04 (d, J = 7.8 Hz, 1H), 7.69 (t, J = 7.8 Hz, 1H), 7.61 (t, J = 7.8 Hz, 1H), 7.47 (d, J = 7.8 Hz, 1H), 3.33 (m, 6H), 3.24 (m, 4H), 2.98 (m, 2H), MS m/z: 555.25 (M + 1). |
| 31 | 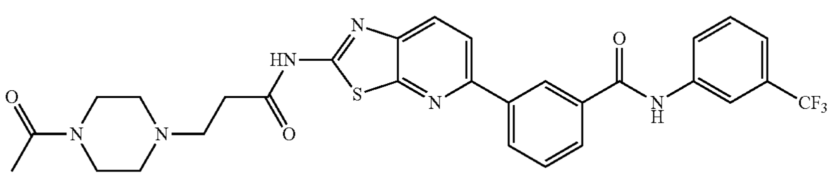 [SMILES: CC(=O)N1CCN(CCC(=O)Nc2nc3ccc(-c4cccc(C(=O)Nc5cccc(C(F)(F)F)c5)c4)nc3s2)CC1] | ¹H NMR 600 MHz (DMSO-d$_6$) δ 12.82 (s, 1H), 10.70 (s, 1H), 8.69 (s, 1H), 8.36 (d, J = 6.0 Hz, 1H), 8.27 (m, 2H), 8.21 (d, J = 7.2 Hz, 1H), 8.07 (m, 1H), 8.04 (d, J = 7.2 Hz, 1H), 7.69 (t, 1H), 7.61 (t, 1H), 7.47 (m, 1H), 4.42 (m, 1H), 4.01 (m, 1H), 3.40 (m, 4H), 3.07 (m, 4H), 2.96 (m, 2H), 2.04 (s, 3H), MS m/z: 597.29 (M + 1). |
| 32 | 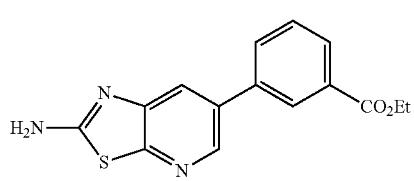 [SMILES: CCOC(=O)c1cccc(-c2cnc3sc(N)nc3c2)c1] | |

TABLE A-continued

| Compound Number | Structure | Physical Data <br> ¹H NMR 600 MHz and/or MS (m/z) |
| --- | --- | --- |
| 33 | 3-(2-aminothiazolo[5,4-b]pyridin-6-yl)benzoic acid | |
| 34 | 3-(2-aminothiazolo[5,4-b]pyridin-6-yl)-4-methylbenzoic acid | |
| 35 | 3-(2-aminothiazolo[5,4-b]pyridin-6-yl)-4-methyl-N-(3-(trifluoromethyl)phenyl)benzamide | |
| 36 | 3-(2-aminothiazolo[5,4-b]pyridin-6-yl)-N-(4-((4-ethylpiperazin-1-yl)methyl)phenyl)-4-methylbenzamide | |
| 37 | 3-(2-aminothiazolo[5,4-b]pyridin-6-yl)-N-(4-((4-ethylpiperazin-1-yl)methyl)-3-(trifluoromethyl)phenyl)-4-methylbenzamide | |

TABLE A-continued

| Compound Number | Structure | Physical Data $^1$H NMR 600 MHz and/or MS (m/z) |
|---|---|---|
| 38 | 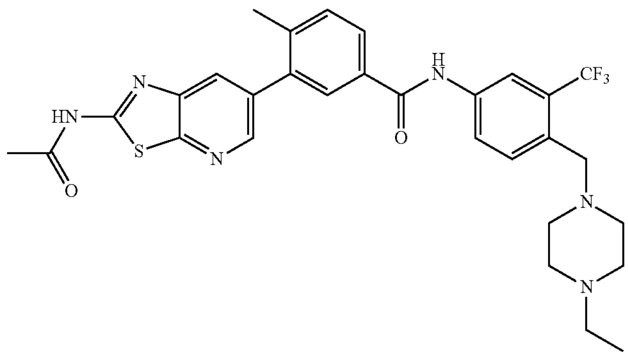 [SMILES: CCN1CCN(Cc2ccc(NC(=O)c3ccc(C)c(-c4cnc5sc(NC(C)=O)nc5c4)c3)cc2C(F)(F)F)CC1] | |
| 39 | 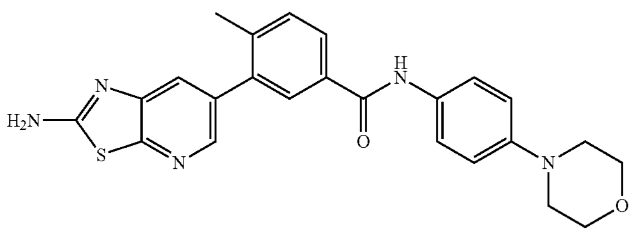 [SMILES: Cc1ccc(C(=O)Nc2ccc(N3CCOCC3)cc2)cc1-c1cnc2sc(N)nc2c1] | |
| 40 | 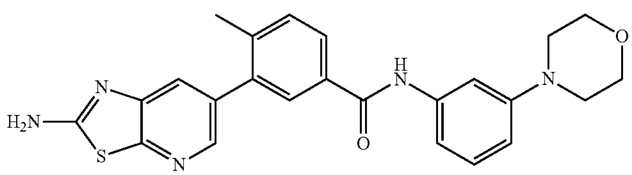 [SMILES: Cc1ccc(C(=O)Nc2cccc(N3CCOCC3)c2)cc1-c1cnc2sc(N)nc2c1] | |
| 41 | 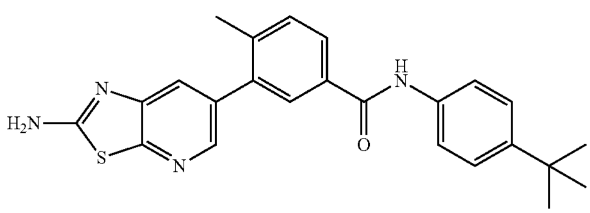 [SMILES: Cc1ccc(C(=O)Nc2ccc(C(C)(C)C)cc2)cc1-c1cnc2sc(N)nc2c1] | |
| 42 | 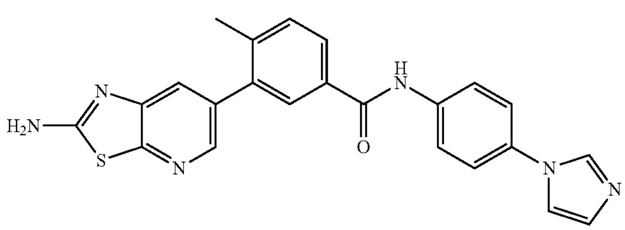 [SMILES: Cc1ccc(C(=O)Nc2ccc(-n3ccnc3)cc2)cc1-c1cnc2sc(N)nc2c1] | |
| 43 | 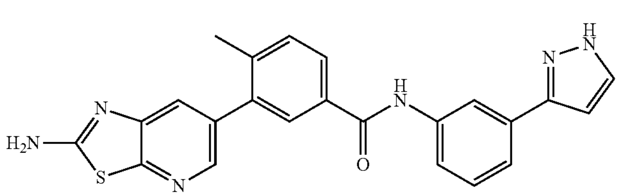 [SMILES: Cc1ccc(C(=O)Nc2cccc(-c3cc[nH]n3)c2)cc1-c1cnc2sc(N)nc2c1] | |

TABLE A-continued

| Compound Number | Structure | Physical Data<br>¹H NMR 600 MHz and/or MS (m/z) |
|---|---|---|
| 44 | 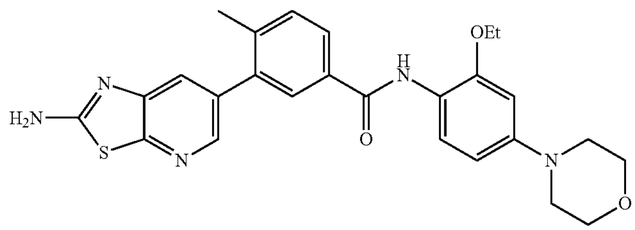 [SMILES: CCOc1cc(N2CCOCC2)ccc1NC(=O)c1ccc(C)c(-c2cnc3sc(N)nc3c2)c1] | |
| 45 | 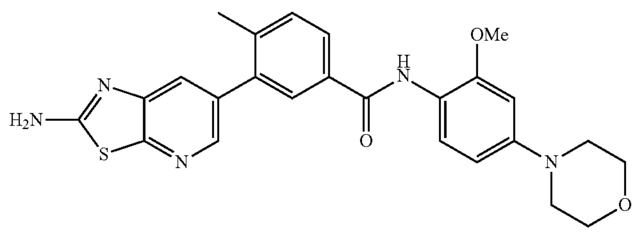 [SMILES: COc1cc(N2CCOCC2)ccc1NC(=O)c1ccc(C)c(-c2cnc3sc(N)nc3c2)c1] | |
| 46 | 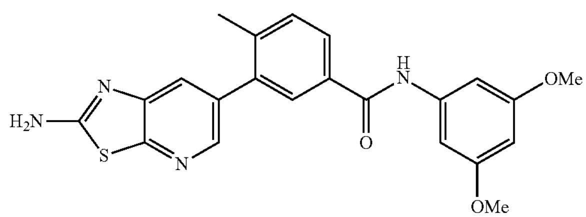 [SMILES: COc1cc(NC(=O)c2ccc(C)c(-c3cnc4sc(N)nc4c3)c2)cc(OC)c1] | |
| 47 | 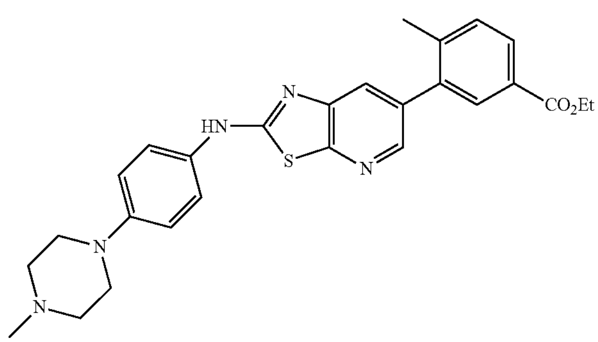 [SMILES: CCOC(=O)c1ccc(C)c(-c2cnc3sc(Nc4ccc(N5CCN(C)CC5)cc4)nc3c2)c1] | |
| 48 | 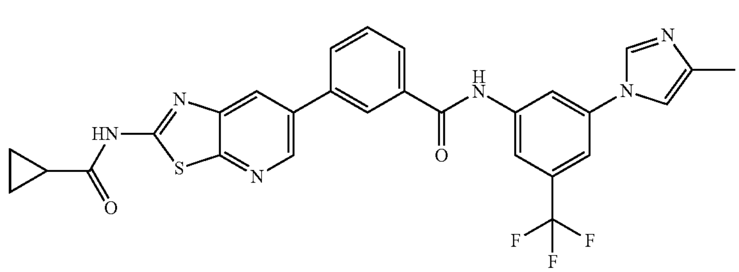 [SMILES: Cc1cn(-c2cc(NC(=O)c3cccc(-c4cnc5sc(NC(=O)C6CC6)nc5c4)c3)cc(C(F)(F)F)c2)cn1] | ¹H NMR 600 MHz (DMSO-d$_6$) δ 12.86 (s, 1H), 11.00 (s, 1H), 9.55 (s, 1H), 8.87 (s, 1H), 8.57 (s, 1H), 8.47 (s, 1H), 8.41 (s, 1H), 8.26 (m, 1H), 8.04 (m, 3H), 7.93 (s, 1H), 7.72 (m, 1H), 2.32 (s, 3H), 2.02 (m, 1H), 0.96 (m, 4H), MS m/z: 563.19 (M + 1). |

TABLE A-continued

| Compound Number | Structure | Physical Data ¹H NMR 600 MHz and/or MS (m/z) |
|---|---|---|
| 49 | 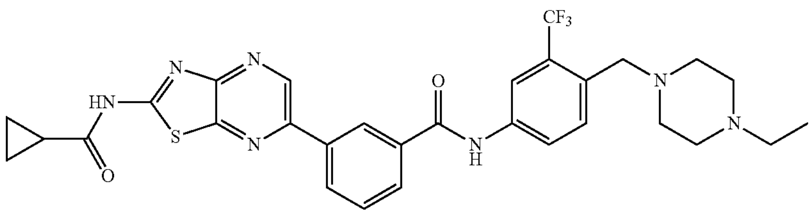 [SMILES: CCN1CCN(Cc2ccc(NC(=O)c3cccc(-c4cnc5nc(NC(=O)C6CC6)sc5n4)c3)cc2C(F)(F)F)CC1] | ¹H NMR 600 MHz (DMSO-d$_6$) δ 13.20 (s, 1H), 10.71 (s, 1H), 9.28 (s, 1H), 8.71 (s, 1H), 8.37 (d, J = 7.8 Hz, 1H), 8.25 (m, 1H), 8.12 (d, J = 9.0 Hz, 1H), 8.06 (d, J = 7.8 Hz, 1H), 7.73 (d, J = 8.4 Hz, 1H), 7.69 (t, 1H), 7.61 (m, 1H), 3.72 (s, 2H), 3.46 (m, 2H), 3.15 (q, 2H), 3.00 (m, 4H), 2.44 (m, 2H), 2.06 (m, 1H), 1.21 (m, 3H), 1.02 (m, 4H), MS m/z: 610.25 (M + 1). |
| 50 | 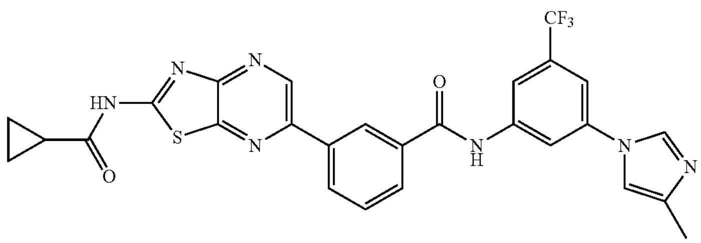 [SMILES: Cc1cn(-c2cc(NC(=O)c3cccc(-c4cnc5nc(NC(=O)C6CC6)sc5n4)c3)cc(C(F)(F)F)c2)cn1] | ¹H NMR 600 MHz (DMSO-d$_6$) δ 13.20 (s, 1H), 11.04 (s, 1H), 9.57 (s, 1H), 9.29 (s, 1H), 8.75 (s, 1H), 8.57 (s, 1H), 8.41 (d, J = 8.4 Hz, 1H), 8.27 (s, 1H), 8.09 (d, J = 7.8 Hz, 1H), 8.02 (s, 1H), 7.92 (s, 1H), 7.73 (t, 1H), 7.61 (m, 1H), 2.35 (s, 3H), 2.07 (m, 1H), 1.02 (m, 4H), MS m/z: 564.25 (M + 1). |
| 51 | 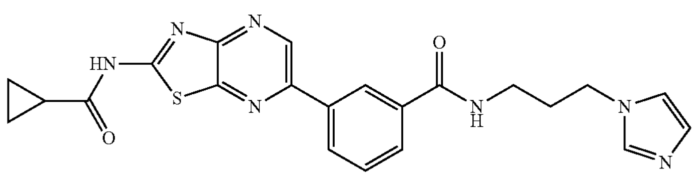 [SMILES: O=C(NCCCn1ccnc1)c1cccc(-c2cnc3nc(NC(=O)C4CC4)sc3n2)c1] | ¹H NMR 600 MHz (DMSO-d$_6$) δ 13.20 (s, 1H), 9.25 (s, 1H), 9.13 (s, 1H), 8.76 (t, 1H), 8.59 (s, 1H), 8.31 (d, J = 8.4 Hz, 1H), 7.94 (d, J = 7.8 Hz, 1H), 7.82 (s, 1H), 7.68 (s, 1H), 7.63 (t, 1H), 4.27 (m, 2H), 3.23 (m, 2H), 2.12 (m, 2H), 2.05 (m, 1H), 1.03 (m, 4H), MS m/z: 448.23 (M + 1). |
| 52 | 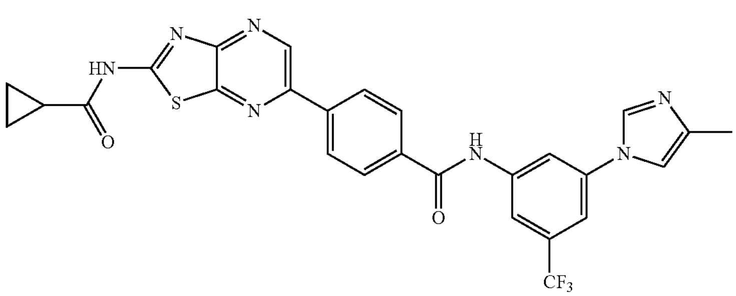 [SMILES: Cc1cn(-c2cc(NC(=O)c3ccc(-c4cnc5nc(NC(=O)C6CC6)sc5n4)cc3)cc(C(F)(F)F)c2)cn1] | ¹H NMR 600 MHz (DMSO-d$_6$) δ 13.22 (s, 1H), 10.97 (s, 1H), 9.32 (s, 1H), 8.58 (s, 1H), 8.38 (d, J = 8.4 Hz, 2H), 8.25 (s, 1H), 8.17 (d, J = 8.4 Hz, 2H), 8.02 (s, 1H), 7.92 (s, 1H), 6.85 (s, 1H), 2.34 (s, 3H), 2.06 (m, 1H), 1.02 (m, 4H), MS m/z: 564.26 (M + 1). |

TABLE A-continued

| Compound Number | Structure | Physical Data ¹H NMR 600 MHz and/or MS (m/z) |
|---|---|---|
| 53 | 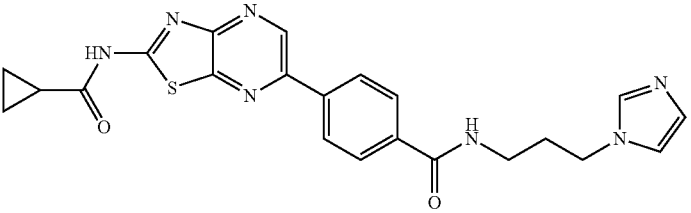 [SMILES: O=C(NCCCn1ccnc1)c1ccc(-c2cnc3nc(NC(=O)C4CC4)sc3n2)cc1] | ¹H NMR 600 MHz (DMSO-d$_6$) δ 13.20 (s, 1H), 9.26 (s, 1H), 9.14 (s, 1H), 8.71 (t, 1H), 8.27 (d, J = 9.0 Hz, 2H), 7.99 (d, J = 8.4 Hz, 2H), 7.82 (s, 1H), 7.69 (s, 1H), 4.27 (t, 2H), 3.30 (m, 2H), 2.11 (t, 2H), 2.06 (m, 1H), 1.02 (m, 4H), MS m/z: 448.20 (M + 1). |
| 54 | 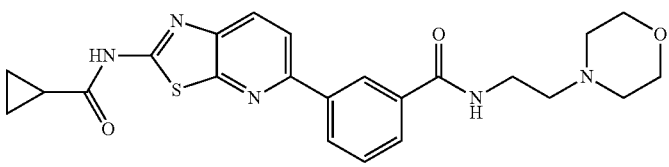 [SMILES: O=C(NCCN1CCOCC1)c1cccc(-c2ccc3nc(NC(=O)C4CC4)sc3n2)c1] | ¹H NMR 600 MHz (DMSO-d$_6$) δ 12.84 (s, 1H), 9.92 (s, 1H), 8.92 (t, 1H), 8.60 (s, 1H), 8.29 (d, J = 7.8 Hz, 1H), 8.19 (d, J = 8.4 Hz, 1H), 8.12 (d, J = 8.4 Hz, 1H), 7.92 (d, J = 7.8 Hz, 1H), 7.62 (t, 1H), 4.00 (m, 2H), 3.68 (m, 4H), 3.58 (m, 2H), 3.36 (m, 2H), 3.15 (m, 2H), 2.04 (m, 1H), 0.99 (m, 4H), MS m/z: 452.30 (M + 1). |
| 55 | 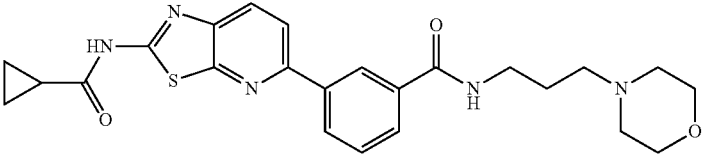 [SMILES: O=C(NCCCN1CCOCC1)c1cccc(-c2ccc3nc(NC(=O)C4CC4)sc3n2)c1] | ¹H NMR 600 MHz (DMSO-d$_6$) δ 12.83 (s, 1H), 9.86 (s, 1H), 8.81 (t, 1H), 8.57 (s, 1H), 8.27 (d, J = 7.2 Hz, 1H), 8.19 (d, J = 8.4 Hz, 1H), 8.12 (d, J = 8.4 Hz, 1H), 7.92 (d, J = 7.8 Hz, 1H), 7.62 (t, 1H), 3.97 (m, 2H), 3.65 (m, 2H), 3.45 (m, 2H), 3.38 (m, 2H), 3.17 (m, 2H), 3.07 (m, 2H), 2.03 (m, 1H), 1.94 (m, 2H), 0.99 (m, 4H), MS m/z: 466.30 (M + 1). |
| 56 | 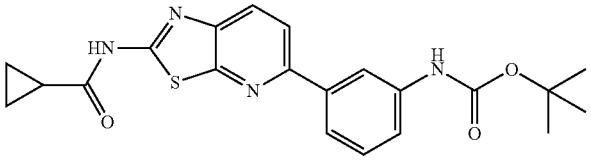 [SMILES: CC(C)(C)OC(=O)Nc1cccc(-c2ccc3nc(NC(=O)C4CC4)sc3n2)c1] | ¹H NMR 600 MHz (DMSO-d$_6$) δ 12.80 (s, 1H), 9.46 (s, 1H), 8.26 (s, 1H), 8.15 (d, J = 8.4 Hz, 1H), 7.94 (d, J = 8.4 Hz, 1H), 7.68 (d, J = 8.0 Hz, 1H), 7.49 (d, J = 8.0 Hz, 1H), 7.37 (t, 1H), 2.05 (m, 1H), 1.48 (m, 9H), 0.98 (m, 4H), MS m/z: 411.24 (M + 1). |

TABLE A-continued

| Compound Number | Structure | Physical Data ¹H NMR 600 MHz and/or MS (m/z) |
|---|---|---|
| 57 | 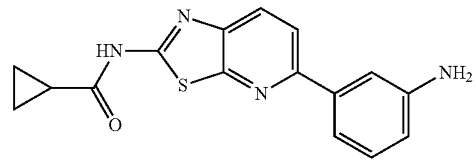 [SMILES: Nc1cccc(-c2ccc3nc(NC(=O)C4CC4)sc3n2)c1] | ¹H NMR 400 MHz (DMSO-d₆) δ 12.77 (s, 1H), 8.13 (d, J = 8.8 Hz, 1H), 7.89 (d, J = 8.8 Hz, 1H), 7.39 (s, 1H), 7.20 (d, J = 8.0 Hz, 1H), 7.13 (t, 1H), 6.62 (d, J = 6.4 Hz, 1H), 5.23 (bs, 2H), 2.02 (m, 1H), 0.96 (m, 4H), MS m/z: 311.10 (M + 1). |
| 58 | 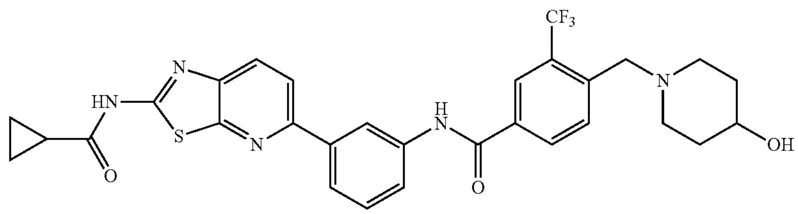 [SMILES: O=C(Nc1cccc(-c2ccc3nc(NC(=O)C4CC4)sc3n2)c1)c1ccc(CN2CCC(O)CC2)c(C(F)(F)F)c1] | ¹H NMR 600 MHz (DMSO-d₆) δ 12.82 (s, 1H), 10.73 (s, 1H), 9.86 (s, 1H), 8.51 (s, 1H), 8.44 (m, 2H), 8.17 (d, J = 9.0 Hz, 1H), 8.11 (d, J = 8.4 Hz, 1H), 8.04 (d, J = 8.4 Hz, 1H), 7.99 (d, J = 7.8 Hz, 1H), 7.52 (t, 1H), 4.57 (m, 2H), 3.36 (m, 2H), 3.23 (m, 2H), 2.03 (m, 1H), 1.98 (m, 2H), 1.75 (m, 1H), 0.99 (m, 4H), MS m/z: 596.26 (M + 1). |
| 59 | 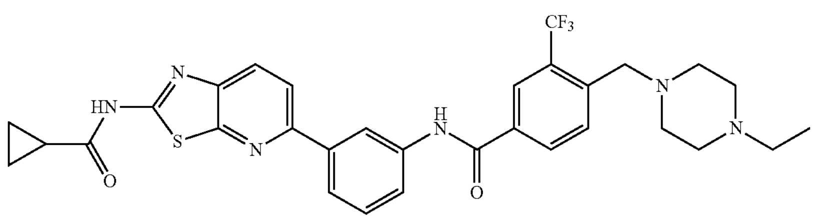 [SMILES: CCN1CCN(Cc2ccc(C(=O)Nc3cccc(-c4ccc5nc(NC(=O)C6CC6)sc5n4)c3)cc2C(F)(F)F)CC1] | ¹H NMR 600 MHz (DMSO-d₆) δ 12.83 (s, 1H), 10.66 (s, 1H), 8.51 (s, 1H), 8.35 (s, 1H), 8.31 (d, J = 8.4 Hz, 1H), 8.17 (d, J = 8.4 Hz, 1H), 8.03 (d, J = 8.4 Hz, 1H), 7.97 (d, J = 7.8 Hz, 1H), 7.94 (d, J = 7.8 Hz, 1H), 7.84 (d, J = 7.2 Hz, 1H), 7.48 (t, 1H), 3.80 (m, 2H), 3.47 (m, 2H), 3.15 (m, 2H), 2.97 (m, 4H), 2.43 (m, 2H), 2.03 (m, 1H), 1.21 (m, 3H), 0.99 (m, 4H), MS m/z: 609.32 (M + 1). |
| 60 | 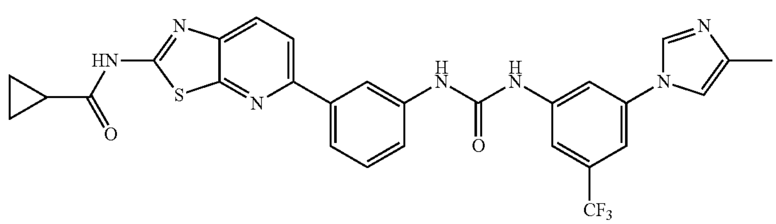 [SMILES: Cc1cn(-c2cc(NC(=O)Nc3cccc(-c4ccc5nc(NC(=O)C6CC6)sc5n4)c3)cc(C(F)(F)F)c2)cn1] | ¹H NMR 400 MHz (DMSO-d₆) δ 12.86 (s, 1H), 9.21 (s, 1H), 9.16 (s, 1H), 8.29 (s, 1H), 8.25 (s, 1H), 8.17 (d, J = 8.4 Hz, 1H), 8.04 (d, J = 9.2 Hz, 1H), 7.88 (s, 1H), 7.85 (s, 1H), 7.77 (d, J = 8.8 Hz, 1H), 7.62 (m, 2H), 7.53 (s, 1H), 7.45 (t, 1H), 2.21 (s, 3H), 2.02 (m, 1H), 0.97 (m, 4H), MS m/z: 578.24 (M + 1). |

TABLE A-continued
| Compound Number | Structure | Physical Data <br> ¹H NMR 600 MHz and/or MS (m/z) |
|---|---|---|
| 61 | 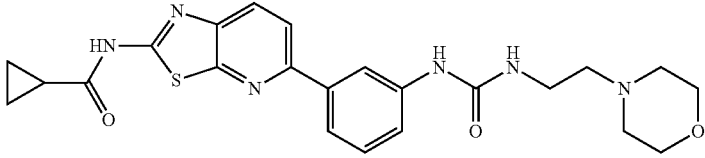 [SMILES: O=C(NCCN1CCOCC1)Nc1cccc(-c2ccc3nc(NC(=O)C4CC4)sc3n2)c1] | ¹H NMR 600 MHz (DMSO-$d_6$) δ 12.80 (s, 1H), 9.81 (s, 1H), 9.15 (s, 1H), 8.21 (s, 1H), 8.14 (d, J = 8.4 Hz, 1H), 7.95 (d, J = 9.0 Hz, 1H), 7.62 (d, J = 7.8 Hz, 1H), 7.53 (d, J = 7.8 Hz, 1H), 7.36 (t, 1H), 6.67 (m, 1H), 3.98 (m, 2H), 3.68 (m, 2H), 3.54 (m, 2H), 3.49 (m, 2H), 3.24 (m, 2H), 3.11 (m, 2H), 2.02 (m, 1H), 0.97 (m, 4H), MS m/z: 467.25 (M + 1). |
| 62 | 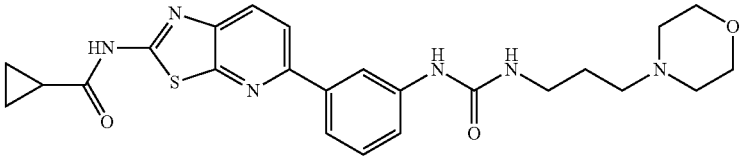 [SMILES: O=C(NCCCN1CCOCC1)Nc1cccc(-c2ccc3nc(NC(=O)C4CC4)sc3n2)c1] | ¹H NMR 600 MHz (DMSO-$d_6$) δ 12.80 (s, 1H), 9.92 (s, 1H), 8.98 (s, 1H), 8.21 (s, 1H), 8.14 (d, J = 8.4 Hz, 1H), 7.94 (d, J = 8.4 Hz, 1H), 7.61 (d, J = 7.8 Hz, 1H), 7.49 (d, J = 7.8 Hz, 1H), 7.34 (t, 1H), 6.56 (m, 1H), 3.97 (m, 2H), 3.66 (m, 2H), 3.44 (m, 2H), 3.18 (m, 4H), 3.06 (m, 2H), 2.02 (m, 1H), 1.85 (m, 2H), 0.97 (m, 4H), MS m/z: 481.3 (M + 1). |
| 63 | 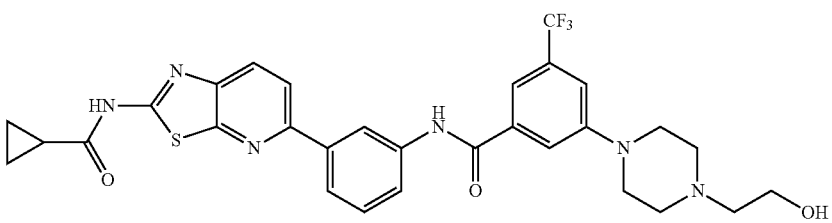 [SMILES: O=C(Nc1cccc(-c2ccc3nc(NC(=O)C4CC4)sc3n2)c1)c1cc(N2CCN(CCO)CC2)cc(C(F)(F)F)c1] | ¹H NMR 400 MHz (DMSO-$d_6$) δ 12.83 (s, 1H), 10.51 (s, 1H), 8.62 (s, 1H), 8.19 (d, J = 8.4 Hz, 1H), 8.05 (d, J = 8.4 Hz, 1H), 7.96 (d, J = 8.0 Hz, 1H), 7.86 (d, J = 8.0 Hz, 1H), 7.76 (s, 1H), 7.66 (s, 1H), 7.41 (t, 1H), 7.36 (m, 1H), 4.46 (m, 1H), 3.53 (m, 2H), 3.18 (m, 6H), 3.03 (m, 2H), 2.67 (m, 2H), 2.02 (m, 1H), 0.97 (m, 4H), MS m/z: 611.3 (M + 1). |

TABLE A-continued

| Compound Number | Structure | Physical Data ¹H NMR 600 MHz and/or MS (m/z) |
|---|---|---|
| 64 | 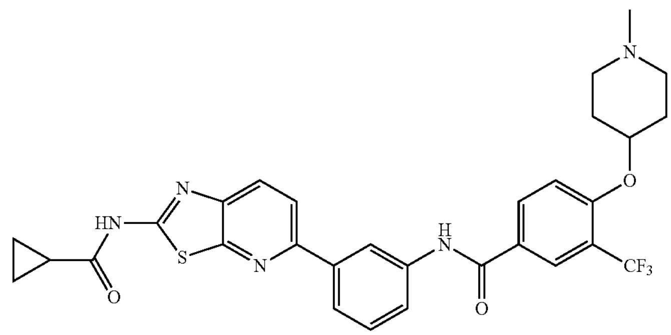 [SMILES: CN1CCC(Oc2ccc(C(=O)Nc3cccc(-c4ccc5nc(NC(=O)C6CC6)sc5n4)c3)cc2C(F)(F)F)CC1] | ¹H NMR 400 MHz (DMSO-$d_6$) δ 12.84 (s, 1H), 10.50 (s, 1H), 8.49 (s, 1H), 8.34 (m, 2H), 8.18 (d, J = 8.8 Hz, 1H), 8.04 (d, J = 8.4 Hz, 1H), 7.98 (d, J = 7.6 Hz, 1H), 7.84 (d, J = 8.0 Hz, 1H), 7.51 (m, 2H), 3.44 (m, 2H), 3.15 (m, 1H), 2.91 (m, 1H), 2.82 (s, 3H), 2.34 (m, 1H), 2.08 (m, 4H), 1.85 (m, 1H), 0.97 (m, 4H), MS m/z: 596.26 (M + 1). |
| 65 | 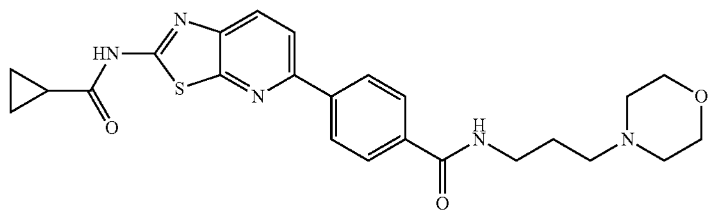 [SMILES: O=C(NCCCN1CCOCC1)c1ccc(-c2ccc3nc(NC(=O)C4CC4)sc3n2)cc1] | ¹H NMR 400 MHz (DMSO-$d_6$) δ 12.84 (s, 1H), 8.70 (m, 1H), 8.23 (d, J = 8.0 Hz, 2H), 8.20 (d, J = 8.4 Hz, 1H), 8.14 (d, J = 8.8 Hz, 1H), 7.97 (d, J = 8.4 Hz, 1H), 3.92 (m, 4H), 3.15 (s, 2H), 2.88 (m, 6H), 2.04 (m, 1H), 1.89 (m, 2H), 0.97 (m, 4H), MS m/z: 466.30 (M + 1). |
| 66 | 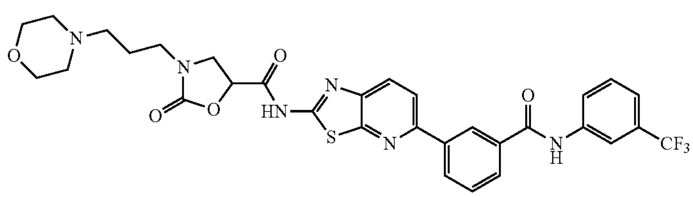 [SMILES: O=C(Nc1cccc(C(F)(F)F)c1)c1cccc(-c2ccc3nc(NC(=O)C4CN(CCCN5CCOCC5)C(=O)O4)sc3n2)c1] | ¹H NMR 400 MHz (DMSO-$d_6$) δ 10.73 (s, 1H), 8.85 (s, 1H), 8.50 (s, 1H), 8.26 (m, 3H), 8.08 (m, 3H), 7.67 (m, 2H), 7.46 (m, 1H), 5.24 (m, 1H), 3.68 (m, 2H), 3.72 (m, 4H), 3.21 (m, 4H), 2.36 (m, 4H), 1.66 (m, 2H), MS m/z: 655.32 (M + 1). |
| 67 | 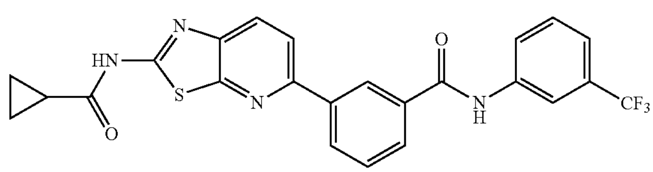 [SMILES: O=C(Nc1cccc(C(F)(F)F)c1)c1cccc(-c2ccc3nc(NC(=O)C4CC4)sc3n2)c1] | ¹H NMR 600 MHz (DMSO-$d_6$) δ 12.81 (s, 1H), 10.67 (s, 1H), 8.66 (s, 1H), 8.34 (d, J = 6.6 Hz, 1H), 8.24 (s, 1H), 8.19 (d, J = 8.4 Hz, 1H), 8.16 (d, J = 8.4 Hz, 1H), 8.07 (d, J = 7.8 Hz, 1H), 8.00 (d, J = 7.2 Hz, 1H), 7.76 (t, J = 7.2 Hz, 1H), 7.59 (t, J = 7.2 Hz, 1H), 7.45 (d, J = 7.2 Hz, 1H), 2.01 (m, 1H), 0.96 (m, 4H), MS m/z: 483.22 (M + 1). |

TABLE A-continued

| Compound Number | Structure | Physical Data ¹H NMR 600 MHz and/or MS (m/z) |
|---|---|---|
| 68 | 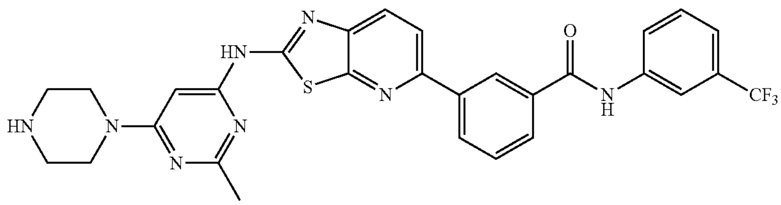 [SMILES: Cc1nc(Nc2nc3ccc(-c4cccc(C(=O)Nc5cccc(C(F)(F)F)c5)c4)nc3s2)cc(N2CCNCC2)n1] | ¹H NMR 600 MHz (DMSO-d$_6$) δ 11.75 (s, 1H), 10.67 (s, 1H), 8.82 (bs, 1H), 8.66 (s, 1H), 8.33 (d, J = 7.2 Hz, 1H), 8.25 (s, 1H), 8.10 (d, J = 9.0 Hz, 1H), 8.08 (m, 2H), 7.99 (d, J = 7.8 Hz, 1H), 7.65 (t, 1H), 7.60 (t, 1H), 7.46 (d, J = 7.2 Hz, 1H), 6.22 (s, 1H), 3.74 (m, 4H), 3.18 (m, 4H), 2.45 (s, 3H), MS m/z: 591.34 (M + 1). |
| 69 | 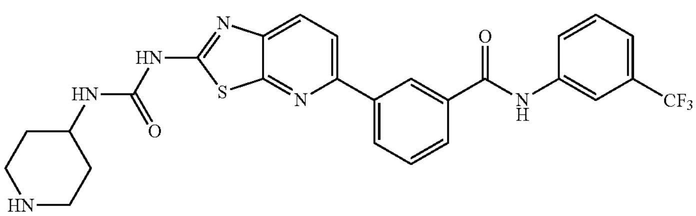 [SMILES: O=C(Nc1nc2ccc(-c3cccc(C(=O)Nc4cccc(C(F)(F)F)c4)c3)nc2s1)NC1CCNCC1] | ¹H NMR 600 MHz (DMSO-d$_6$) δ 10.68 (s, 1H), 8.65 (s, 1H), 8.32 (d, J = 8.4 Hz, 1H), 8.26 (s, 1H), 8.13 (m, 3H), 8.00 (d, J = 7.2 Hz, 1H), 7.66 (t, 1H), 7.62 (t, 1H), 7.47 (d, J = 8.4 Hz, 1H), 7.31 (d, J = 6.0 Hz, 1H), 6.09 (d, J = 7.2 Hz, 1H), 3.62 (m, 1H), 3.28 (m, 2H), 2.93 (m, 2H), 1.88 (m, 2H), 1.45 (m, 2H), MS m/z: 541.20 (M + 1). |
| 70 | 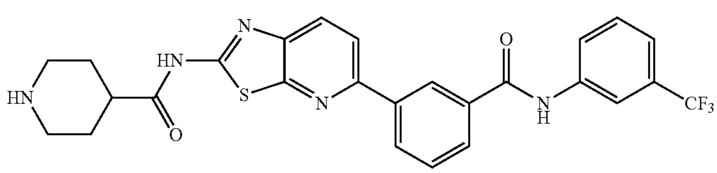 [SMILES: O=C(Nc1cccc(C(F)(F)F)c1)c1cccc(-c2ccc3nc(NC(=O)C4CCNCC4)sc3n2)c1] | ¹H NMR 600 MHz (DMSO-d$_6$) δ 12.71 (s, 1H), 10.71 (s, 1H), 8.69 (s, 1H), 8.46 (m, 1H), 8.36 (d, J = 8.4 Hz, 1H), 8.27 (s, 1H), 8.24 (d, J = 8.4 Hz, 1H), 8.20 (d, J = 9.0 Hz, 1H), 8.09 (d, J = 7.8 Hz, 1H), 8.03 (d, J = 7.2 Hz, 1H), 7.68 (t, 1H), 7.62 (t, 1H), 7.47 (d, J = 7.8 Hz, 1H), 3.66 (m, 2H), 2.96 (m, 2H), 2.88 (m, 1H), 2.06 (m, 2H), 1.83 (m, 2H), MS m/z: 526.32 (M + 1). |

TABLE A-continued

| Compound Number | Structure | Physical Data $^1$H NMR 600 MHz and/or MS (m/z) |
|---|---|---|
| 71 | 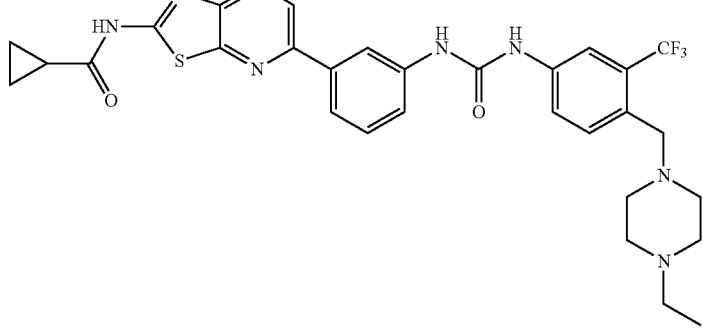 | $^1$H NMR 600 MHz (CDCl$_3$) δ 8.51 (s, 1H), 7.83 (d, J = 1.8 Hz, 1H), 7.48 (m, 2H), 7.19 (m, 3H), 7.12 (m, 2H), 6.85 (d, J = 3.0 Hz, 1H), 6.49 (m, 1H), 6.19 (m, 2H), 3.84 (m, 1H), 3.78 (s, 3H), 3.46 (m, 2H), 3.19 (m, 1H), 2.90 (m, 2H), 1.99 (m, 2H), 1.69 (m, 2H), 1.19 (d, J = 6.6 Hz, 6H), MS m/z: 624.36 (M + 1). |
| 72 | 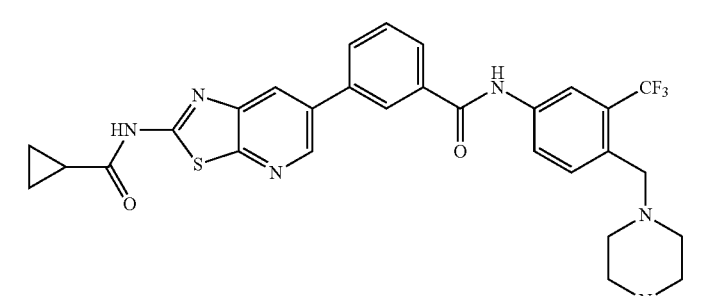 | $^1$H NMR 600 MHz (DMSO-d$_6$) δ 12.87 (s, 1H), 10.65 (s, 1H), 9.74 (bs, 1H), 8.47 (d, J = 1.8 Hz, 1H), 8.37 (s, 1H), 8.23 (s, 1H), 8.11 (d, J = 8.4 Hz, 1H), 8.06 (d, J = 7.8 Hz, 1H), 8.01 (d, J = 7.8 Hz, 1H), 7.73 (d, J = 8.4 Hz, 1H), 7.68 (t, 1H), 3.69 (s, 2H), 3.48 (m, 2H), 3.14 (q, 2H), 2.98 (m, 4H), 2.45 (m, 2H), 2.05 (m, 1H), 1.20 (m, 3H), 0.99 (m, 4H), MS m/z: 609.37 (M + 1). |
| 73 | 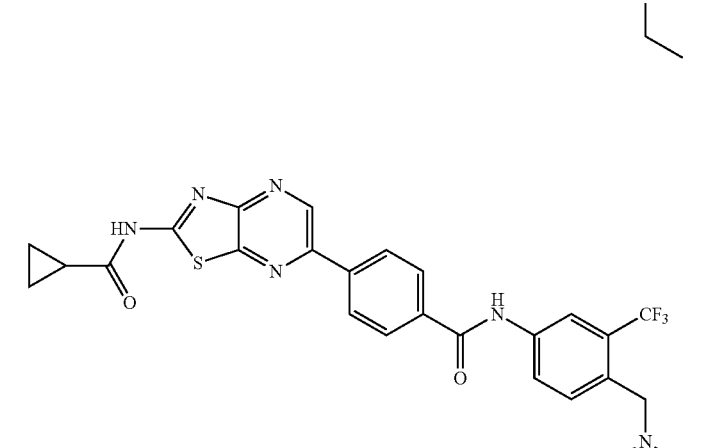 | $^1$H NMR 600 MHz (DMSO-d$_6$) δ 13.21 (s, 1H), 10.65 (s, 1H), 9.56 (bs, 1H), 9.29 (s, 1H), 8.36 (d, J = 7.2, 1H), 8.24 (s, 1H), 8.13 (m, 3H), 7.72 (d, J = 7.8 Hz, 1H), 3.69 (s, 2H), 3.46 (m, 2H), 3.13 (m, 2H), 2.98 (m, 4H), 2.40 (m, 2H), 2.06 (m, 1H), 1.19 (m, 3H), 1.02 (m, 4H), MS m/z: 610.25 (M + 1). |

Methods of Treatment

Compounds of the present invention are useful for the treatment of protein kinase-associated disorders.

As used herein, the term "protein kinase-associated disorder" includes disorders and states (e.g., a disease state) that are associated with the activity of a protein kinase.

Non-limiting examples of protein kinase-associated disorders include abnormal cell proliferation, including protein kinase-associated cancers, viral infections, fungal infections, autoimmune diseases and neurodegenerative disorders.

Non-limiting examples of protein-kinase associated disorders include proliferative diseases, such as viral infections, auto-immune diseases, fungal disease, cancer, psoriasis, vascular smooth cell proliferation associated with atherosclerosis, pulmonary fibrosis, arthritis glomerulonephritis, chronic inflammation, neurodegenerative disorders, such as Alzheimer's disease, and post-surgical stenosis and restenosis. Protein kinase-associated disorders also include diseases related to abnormal cell proliferation, including, but not limited to, cancers of the head and neck, breast, ovary, cervix, prostate, testis, esophagus, stomach, skin, lung, bone, colon, pancreas, thyroid, biliary passages, buccal cavity and pharynx (oral), larynx, lip, tongue, mouth, small intestine, colon-rectum, large intestine, rectum, prostate, brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia.

Protein kinase-associated disorders also include diseases associated with apoptosis, including, but not limited to, cancer, viral infections, autoimmune diseases and neurodegenerative disorders.

Examples of protein kinase-associated cancers include carcinomas, hematopoietic tumors of lymphoid lineage, hematopoietic tumors of myeloid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

Additional, non-limiting examples of protein-kinase associated disorders include tumor angiogenesis and metastasis. Non-limiting examples of protein-kinase associated disorders also include vascular smooth muscle proliferation associated with atherosclerosis, postsurgical vascular stenosis and restenosis, and endometriosis.

Non-limiting examples of protein-kinase associated disorders include viral infections in a patient in need thereof, wherein the viral infections include, but are not limited to, HIV, human papilloma virus, herpes virus, poxyvirus, Epstein-Barr virus, Sindbis virus and adenovirus.

Further non-limiting examples of protein-kinase associated disorders include those associated with infectious agents, including yeast, fungi, protozoan parasites such as *Plasitiodium falciparum*, and DNA and RNA viruses.

Compounds of the present invention are useful for the treatment of cancer, wherein the cancer is selected from the group consisting of multiple myeloma, chronic myelogenous leukemia, pancreatic cancer, non-small cell lung cancer, lung cancer, breast cancer, colon cancer, ovarian cancer, prostate cancer, malignant melanoma, non-melanoma skin cancers, gastrointestinal stromal tumors, hematologic tumors, hematologic malignancies, childhood leukemia, childhood lymphomas, multiple myeloma, Hodgkin's disease, lymphomas of lymphocytic origin, lymphomas of cutaneous origin, acute leukemia, chronic leukemia, acute lymphoblastic leukemia, acute myelocytic leukemia, chronic myelocytic leukemia, plasma cell neoplasm, lymphoid neoplasm and cancers associated with AIDS.

In another embodiment, compounds of the present invention are used for modulating the activity of a protein kinase, including, but not limited to, protein kinases selected from the group consisting of Abl, ATK, BCR-Abl, Blk, Brk, Btk, BRAF, c-fms, e-kit, c-met, c-src, CDK, cRaf1, CSFIR, CSK, EGFR, ErbB2, ErbB3, ErbB4, ERK, DDR-1, Fak, fes, FGFR1, FGFR2, FGFR3, FGFR4, FGFR5, Fgr, FLK-4, flt-1, flt-3, flt-4, Fps, Frk, Fyn, GSK, Gst-Flk1, Hck, Her-2, Her-4, HIPK-1, IGF-1R, INS-R, Jak, JNK, KDR, Lck, LOK, Lyn, MEK, p38, panHER, PDGFR, PLK, PKC, PYK2, Raf, Rho, ros, SRC, TRK, TYK2, UL97, VEGFR, Yes, Zap70, Aurora-A, GSK3-alpha, HIPK1, HIPK2, HIP3, IRAK1, JNK1, JNK2, JNK3, TRKB, CAMKII, CK1, CK2, RAF, GSK3Beta, MAPK1, MKK4, MKK7, MST2, NEK2, AAK1, PKCalpha, PKD, RET, RIPK2, ROCK-II, and TIE2

As used herein, the term "modulating" or "modulation" refers to the alteration of the catalytic activity of a protein kinase. In particular, modulating refers to the activation or inhibition of the catalytic activity of a protein kinase, depending on the concentration of the compound or salt to which the protein kinase is exposed or, more preferably, the inhibition of the catalytic activity of a protein kinase. The term "catalytic activity" as used herein refers to the rate of phosphorylation of tyrosine, serine or threonine under the influence, direct or indirect, of a protein kinase.

The three main classes that pharmacological inhibitors of kinase activity are categorized by are (1) Type I, or "DFG-in" ATP competitive inhibitors, which directly compete with ATP in the ATP binding site (i.e. dual SRrc ABL inhibitor dasatinib, (2) Type II, or "DFG-out" ATP competitive inhibitors, which, in addition to binding the ATP binding site also engage an adjacent hydrophobic binding site that is only accessible when the kinase is in an inactivated configuration (i.e. the activation loop is oriented in a conformation that would block substrate binding) (i.e. imatinib, nilotinib), and (3) non-ATP competitive inhibitors that binds at sites outside the ATP binding site that affect the activity of the kinase (i.e. GNF-2).

Second generation Abl inhibitors, such as dasatinib, and nilotinib, are highly active against imatinib-resistant leukemia. Both agents are significantly more potent against Bcr-Abl than imatinib, and are active against many imatinib-resistant Bcr-Abl mutants. However, neither agent is able to override imatinib resistance due to the mutation of a threonine to an isoleucine at residue 315 (T315I, the "gatekeeper" position). This highly prevalent and highly imatinib-resistant mutation is centrally located in the nucleotide binding cleft of Abl. Both dasatinib and nilotinib make a hydrogen bonding interaction to the side-chain hydroxyl group of T315, which is resistant to these compounds due to direct steric intrusion of the isobutyl side chain and a loss in the middle of the ATP-cleft of a hydrogen-bonding interaction.

In addition to BCR-Abl T315I, other gatekeeper residues that play an integral role in imatinib-resistant disease include c-kit-T670I, which is associated with imatinib-resistant gastrointestinal stromal tumor characterized by early metastasis and shorter progression-free survival; this mutation substantially modifies the binding pocket of c-Kit, and occurs only under the selective pressure of imatinib therapy, PDGFRA-T674M/I, which is found in the FIP1LI-PDGFRA kinase domain and gives rise to imatinib resistance in idiopathic hypereosinophilic syndrome (HES), and PDGFRB-T681M/I.

The compounds of the invention are type II class kinase inhibitors that traverse the gatekeeper position in a manner that accommodates amino acid side chains of a variety of sizes. A co-crystal structure of compound 2 (Table A) with Src demonstrates that compound 2 does indeed bind as a type II inhibitor (FIG. 1).

The above-listed protein kinases may exhibit one or more point mutations, including, but not limited to mutations of the hinge region, mutations of the P-loop, and mutations of the A-loop.

In a preferred embodiment, the protein kinase is selected from the group consisting of mutated or non-mutated Abl, mutated or non-mutated c-kit, mutated or non-mutated BCR-Abl, mutated or non-mutated PDGFR, mutated or non-mutated Src and any combination thereof. In a particularly preferred embodiment, the protein kinase is selected from the group consisting of mutated or non-mutated c-kit, mutated or non-mutated BCR-Abl, mutated or non-mutated PDGFR, and mutated or non-mutated Src.

In one embodiment, a compound of the present invention is characterized as an inhibitor of a combination of protein kinases, e.g., BCR-Abl and/or c-kit and/or PDGFR.

In certain embodiments, a compound of the present invention is used for protein kinase-associated diseases, and/or as an inhibitor of any one or more protein kinases. It is envisioned that a use can involve the inhibition one or more isoforms of the protein kinase.

In one embodiment, the compounds of the present invention selectively inhibit FLT3 kinase activity and the proliferation, viability, and cell cycle progression of leukemic cells harboring mutant FLT3.

In another embodiment, the compounds of the present invention selectively inhibit FLT3 kinase activity and the proliferation, viability, and cell cycle progression of leukemic cells harboring mutant FLT3, with no apparent effect on cells harboring wild-type FLT3.

The efficacy of therapeutic kinase inhibitors such as imatinib, dasatinib and nilotinib is typically correlated with their affinity toward one or more kinase targets that are associated with a particular disease state. Point-mutations, which can occur naturally or under the selective pressure of chemotherapy, can decrease the affinity of the chemotherapeutic for its kinase target, thereby conferring resistance to these therapies.

The compounds of the present invention are useful in overcoming drug resistance due to acquired point mutations in the molecular targets.

The compounds of the invention are also inhibitors of mutated or non-mutated forms of the kinase enzymes Abl, BCR-Abl, c-kit PDGFR and Src, which are implicated in certain disease states related to cancer, e.g. pancreatic cancer, non-small cell lung cancer, gastrointestinal stromal tumor, or chronic myelogenous leukemia. BCR-Abl activates a number of cell cycle-controlling proteins and enzymes, speeding up cell division and inhibiting DNA repair, thus resulting in genomic instability and, potentially, blast crisis in CML. Aberrant activation of c-kit is observed in most gastrointestinal stromal tumors, while the effects of PDGFR include cell proliferation and angiogenesis.

Without being bound by theory, it is believed that inhibition of the kinase enzymes Abl, BCR-Abl, c-kit, PDGFR and Src will promote apoptosis, inhibit cancer cell proliferation and inhibit tumor growth.

The present invention also includes treatment of one or more symptoms of cancer, e.g. pancreatic cancer, non-small cell lung cancer, gastrointestinal stromal tumor, or chronic myelogenous leukemia, as well as protein kinase-associated disorders as described above, but the invention is not intended to be limited to the manner by which the compound performs its intended function for treatment of a disease. The present invention includes treatment of diseases described herein in any manner that allows treatment to occur.

In certain embodiments, the compounds of the invention are used alone or in combination with other therapeutic agents, e.g. imatinib, nilotinib or dasatinib.

In another embodiment, the invention provides a pharmaceutical composition of any of the compounds of the present invention. In a related embodiment, the invention provides a pharmaceutical composition of any of the compounds of the present invention and a pharmaceutically acceptable carrier or excipient. In certain embodiments, the invention includes the compounds as novel chemical entities.

In other embodiments, the present invention provides a method for inhibiting the activity of a protein kinase. The method includes contacting a cell with any of the compounds of the present invention. In a related embodiment, the method further provides that the compound is present in an amount effective to selectively inhibit the activity of a protein kinase.

Additionally, a method of the invention includes administering to a subject an effective amount of a protein kinase-modulating compound of the invention, e.g., protein kinase-modulating compounds of Formula I, Formula II or Formula III, as well as Table A (including pharmaceutically acceptable salts thereof, as well as enantiomers, stereoisomers, rotamers, tautomers, diastereomers, atropisomers or racemates thereof).

In certain embodiments, the compounds of the invention are used for the treatment of cancer. In one embodiment, compound 2 is used for the treatment of cancer. In another embodiment, compound 3 is used for the treatment of cancer.

In other embodiments, the present invention provides a use of any of the compounds of the invention for manufacture of a medicament to treat cancer.

In other embodiments, the invention provides a method of manufacture of a medicament, including formulating any of the compounds of the present invention for treatment of a subject.

One embodiment provided herein is a method of treating pancreatic cancer, comprising administering compound 2 to a subject in need thereof, such that the pancreatic cancer is treated.

Another embodiment provided herein is a method of treating non-small cell lung cancer, comprising administering compound 2 to a subject in need thereof, such that the non-small cell lung cancer is treated.

In yet another embodiment provided herein is a method of treating gastrointestinal stromal tumor, comprising administering compound 2 to a subject in need thereof, such that the gastrointestinal stromal tumor is treated.

In still another embodiment provided herein is a method of treating chronic myelogenous leukemia, comprising administering compound 2 to a subject in need thereof, such that the chronic myelogenous leukemia is treated.

In another embodiment provided herein is a method of treating acute myeloid leukemia, comprising administering compound 2 to a subject in need thereof, such that the acute myeloid leukemia is treated.

One other embodiment provided herein is a method of treating pancreatic cancer, comprising administering compound 3 to a subject in need thereof, such that the pancreatic cancer is treated.

Another embodiment provided herein is a method of treating non-small cell lung cancer, comprising administering compound 3 to a subject in need thereof, such that the non-small cell lung cancer is treated.

In yet another embodiment provided herein is a method of treating gastrointestinal stromal tumor, comprising administering compound 3 to a subject in need thereof, such that the gastrointestinal stromal tumor is treated.

In still another embodiment provided herein is a method of treating chronic myelogenous leukemia, comprising administering compound 3 to a subject in need thereof, such that the chronic myelogenous leukemia is treated.

In another embodiment provided herein is a method of treating acute myeloid leukemia, comprising administering compound 3 to a subject in need thereof, such that the acute myeloid leukemia is treated.

In certain embodiments, the compounds of the invention are used as medicaments. In one embodiment, compound 2 is used as a medicament. In another embodiment, compound 3 is used as a medicament.

One embodiment, provided herein is the use of compound 2 for the manufacture of a medicament for the treatment of pancreatic cancer in a subject in need thereof.

In another embodiment, provided herein is the use of compound 2 for the manufacture of a medicament for the treatment of non-small cell lung cancer in a subject in need thereof.

In yet another embodiment, provided herein is the use of compound 2 for the manufacture of a medicament for the treatment of gastrointestinal stromal tumor in a subject in need thereof.

In still another embodiment, provided herein is the use of compound 2 for the manufacture of a medicament for the treatment of chronic myelogenous leukemia in a subject in need thereof.

In one embodiment, provided herein is the use of compound 2 for the manufacture of a medicament for the treatment of acute myeloid leukemia in a subject in need thereof.

One other embodiment, provided herein is the use of compound 3 for the manufacture of a medicament for the treatment of pancreatic cancer in a subject in need thereof.

In another embodiment, provided herein is the use of compound 3 for the manufacture of a medicament for the treatment of non-small cell lung cancer in a subject in need thereof.

In yet another embodiment, provided herein is the use of compound 3 for the manufacture of a medicament for the treatment of gastrointestinal stromal tumor in a subject in need thereof.

In still another embodiment, provided herein is the use of compound 3 for the manufacture of a medicament for the treatment of chronic myelogenous leukemia in a subject in need thereof.

In another embodiment, provided herein is the use of compound 3 for the manufacture of a medicament for the treatment of acute myeloid leukemia in a subject in need thereof.

DEFINITIONS

The term "treat," "treated," "treating" or "treatment" includes the diminishment or alleviation of at least one symptom associated or caused by the state, disorder or disease being treated. In certain embodiments, the treatment comprises the induction of a protein kinase-associated disorder, followed by the activation of the compound of the invention, which would in turn diminish or alleviate at least one symptom associated or caused by the protein kinase-associated disorder being treated. For example, treatment can be diminishment of one or several symptoms of a disorder or complete eradication of a disorder.

The term "use" includes any one or more of the following embodiments of the invention, respectively: the use in the treatment of protein kinase-associated disorders; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from cancer, e.g. pancreatic cancer, non-small cell lung cancer, gastrointestinal stromal tumor, or chronic myelogenous leukemia, or inflammation, cardiac hypertrophy, and HIV infection, as well as those diseases that depend on the activity of protein kinases. The term "use" further includes embodiments of compositions herein which bind to a protein kinase sufficiently to serve as tracers or labels, so that when coupled to a fluor or tag, or made radioactive, can be used as a research reagent or as a diagnostic or an imaging agent.

The term "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, e.g. pancreatic cancer, non-small cell lung cancer, gastrointestinal stromal tumor, or chronic myelogenous leukemia, or inflammation, cardiac hypertrophy, and HIV infection, and other diseases or conditions described herein (e.g., a protein kinase-associated disorder). In another embodiment, the subject is a cell.

The language "protein kinase-modulating compound," "modulator of protein kinase" or "protein kinase inhibitor" refers to compounds that modulate, e.g., inhibit, or otherwise alter, the activity of a protein kinase. Examples of protein kinase-modulating compounds include compounds of the invention, i.e., Formula I, as well as the compounds of Table A (including pharmaceutically acceptable salts thereof, as well as enantiomers, stereoisomers, rotamers, tautomers, diastereomers, atropisomers or racemates thereof).

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, 1 to 6 carbons, 1 to 4 carbons, or 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

As used herein, the term "cycloalkyl" refers to saturated or unsaturated monocyclic, bicyclic or tricyclic hydrocarbon groups of 3-12 carbon atoms, preferably 3-9, or 3-7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group.

"Alkoxy" refers to those alkyl groups, having from 1 to 10 carbon atoms, attached to the remainder of the molecule via an oxygen atom. Alkoxy groups with 1-8 carbon atoms are preferred. The alkyl portion of an alkoxy may be linear, cyclic, or branched, or a combination thereof. Examples of alkoxy groups include methoxy, ethoxy, isopropoxy, butoxy, cyclopentyloxy, and the like. An alkoxy group can also be represented by the following formula: —$OR^i$, where $R^i$ is the "alkyl portion" of an alkoxy group.

The term "heteroalkyl," by itself or in combination with another term, means, unless otherwise stated, a stable straight or branched chain, or combinations thereof, consisting of the stated number of carbon atoms and from one to five heteroatoms, more preferably from one to three heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

The term "alkylcarbonyl" refers to a group having the formula —C(O)—$R^{ii}$, wherein $R^{ii}$ is an alkyl group as defined above and wherein the total number of carbon atoms refers to the combined alkyl and carbonyl moieties. An "alkylcarbonyl" group can be attached to the remainder of the molecule via an alkyl group (i.e., -alkyl-C(O)—$R^{ii}$).

The term "alkoxycarbonyl" refers to a group having the formula —C(O)O—$R^{ii}$, wherein $R^{iii}$ is an alkyl group as defined above and wherein the total number of carbon atoms refers to the combined alkyl and carbonyl moieties. An "alkoxycarbonyl" group can be attached to the remainder of the molecule via an alkyl group (i.e., -alkyl-C(O)O—$R^{iii}$).

The term "heteroalkylcarbonyl" refers to a group having the formula —C(O)$R^{iv}$, wherein $R^{iv}$ is a heteroalkyl group as defined above and wherein the total number of carbon atoms refers to the combined alkyl and carbonyl moieties. A "heteroalkylcarbonyl" group can be attached to the remainder of the molecule via an alkyl or heteroalkyl group (i.e., -alkyl-C(O)O—$R^{iv}$ or -heteroalkyl-C(O)O—$R^{iv}$).

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" refers to a five-member to ten-member, fully saturated or partially unsaturated nonaromatic heterocylic groups containing at least one heteroatom such as O, S or N. The most frequent examples are piperidinyl, morpholinyl, piperazinyl, pyrrolidinyl or pirazinyl. Attachment of a heterocyclyl substituent can occur via a carbon atom or via a heteroatom.

Moreover, the alkyl, alkenyl, cycloalkyl, cycloalkenyl, alkoxy, aryl, heteroaryl, and heterocycle groups described above can be "unsubstituted" or "substituted." The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$, —$OSO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

In a particular embodiment of the invention, the term "amine" or "amino" refers to substituents of the formulas $N(R^8)R^9$, $CH_2N(R^8)R^9$ and $CH(CH_3)N(R^8)R^9$, wherein $R^8$ and $R^9$ are each, independently, selected from the group consisting of H and $(C_1-C_4-alkyl)_{0-1}G$, wherein G is selected from the group consisting of COOH, H, $PO_3H$, $SO_3H$, Br, Cl, F, O—$C_{1-4}$-alkyl, S—$C_{1-4}$-alkyl, aryl, $C(O)OC_1-C_6$-alkyl, $C(O)C_1-C_4$-alkyl-COOH, $C(O)C_1-C_4$-alkyl and $C(O)$-aryl.

The description of the disclosure herein should be construed in congruity with the laws and principals of chemical bonding. For example, it may be necessary to remove a hydrogen atom in order accommodate a substituent at any given location. Furthermore, it is to be understood that definitions of the variables (i.e., "R groups"), as well as the bond locations of the generic formulae of the invention (e.g., Formulas I, II or III), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

The compounds of this invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

Isotopes

The present invention includes all pharmaceutically acceptable isotopically-labeled compounds of the invention, i.e. compounds of Formulas (I), (II) and (III), wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formulas (I), (II) and (III), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of Formulas (I), (II) and (III) can generally be prepared by conventional techniques known to those skilled in the art or by processes analogous to those described in the accompanying Examples and Preparations using an appropriate isotopically-labeled reagents in place of the non-labeled reagent previously employed.

Combinations

The compounds of this invention are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds, which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2dimethyl-1-oxopropoxy-4-methyl-2-[4-[2-(1-piperidinyl)ethoxy]phenyl]-2H-1- benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds, which interfere or inhibit the binding of retinoids to the receptor, regardless of mechanism. Examples of such retinoid receptor modulators include bexarotene, tretinoin, 13-cis-retinoic acid, 9-cis-retinoic acid, .alpha.-difluoromethylornithine, ILX23-7553, trans-N-(4'-hydroxyphenyl) retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, doxorubicin, altretamine, prednimustine, dibromodulcitol, ranimustine, fotemustine, nedaplatin, oxaliplatin, temozolomnide, heptaplatin, estramustine, improsulfan tosilate, trofosfainide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamiine(-chloro) platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy4-methyl-1H,12H-benzo[de]pyrano[3',4':b,7]indolizino[1,2b]quinoline-10,13(9H, 15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d-)-1,3-dioxol-6-one, 2,3-(methylenedioxy)-5-methyl-7-hydroxy-8-methoxybenzo[c]-phenanthridinium, 6,9-bis[[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen4-ylmethyl-]formamide, N-(2-(dimethylamino)ethyl)acridine4-carboxamide, 6-[[2-(dimethylamino)ethyl]amino]-3-hydroxy-7H-indeno[2,1-c] quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino4-oxo4,6,7,8-tetrahydro-3H-pyrimidino[5,4-b][1,4]thiazin-6-yl-(-S)-ethyl]-2,5-thienoyl-L-glutamic acid, aminopterin, 5-flurouracil, alanosine, 11-acetyl-8-(carbamoyloxymethyl)4-formyl-6-methoxy-14-oxa-1,11-diazatetra-cyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-amninopyridine-2-carboxaldehyde thiosemicarbazone.

"Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include, but are not limited to lovastatin, simvastatin, pravastatin, fluvastatin, atorvastatin and cerivastatin. The structural formulae of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (+/−)-6-[amino(4-chlorophenyl)(1-methyl-1H-imidazol-5- yl)methyl]-4-(3-chlorophenyl)-1-methyl-2(1H)-quinolinone, (−)-6-[amino(4-chlorophenyl)(1-methyl-1H-imidazol-5-yl)methyl]4-(3-chloro-phenyl)-1-methyl-2(1H)-quinolinone, (+)-6-[amino(4-chlorophenyl)(1-methyl-1H-imidazol-5-yl)methyl]4-(3-chlorophenyl)-1-methyl-2(1H)-quinolinone, 5(S)-n-butyl-1-(2,3-dimethylphenyl)4-[1-(4-cyanobenzyl)-5-imidazolylmethy-1]-2-piperazinone, (S)-1-(3-chlorophenyl) 4-[1-(4-cyanobenzyl)-5-imidazolylmethyl]-5-[2-(ethanesulfonyl)methyl)-2-piperazinone, 5(S)-n-Butyl-1-(2-methylphenyl)4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl4-(4-chloropyridin-2-ylmethyl)-piperidine-1-ylmethyl-]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol4-ylmethyl}benzonitrile-, 4-{3-[4-(5-chloro-2-oxo-2H-[1,2']bipyridin-5'-ylmethyl]-3H-imidazol4-ylmethyl}benzonitrile, 4-{3-[4-(2-oxo-2H-[1,2']bipyridin-5'-ylmethyl]-3H-imidazol4-ylmethyl}benzonitrile, 4-[3-(2-oxo-1-phenyl-1,2-dihydropyridin4-ylmethyl)-3H-imidazol4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (+/−)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H,17H-18,21-ethano-6,10:12,16-dimetheno-22H-imidazo-[3,4-h][1,8,11,14]oxatriazacycloeicosine-9-carbonitrile, and (+/−)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-.alpha., interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamnine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF. (see, Nature Biotechnology, Vol. 17, pp. 963-968 (October 1999); Kim et al., Nature, 362, 841-844 (1993); WO 00/44777; and WO 00/61186).

Assays

The inhibition of protein kinase activity by the compounds of the invention may be measured using a number of assays available in the art. Examples of such assays are described in the Exemplification section below.

Pharmaceutical Compositions

The compounds of the present invention are suitable as active agents in pharmaceutical compositions that are efficacious particularly for treating protein kinase-associated disorders and cancer, e.g. pancreatic cancer, non-small cell lung cancer, gastrointestinal stromal tumor, or chronic myelogenous leukemia. The pharmaceutical composition in various embodiments has a pharmaceutically effective amount of the present active agent along with other pharmaceutically acceptable excipients, carriers, fillers, diluents and the like.

The language "pharmaceutically effective amount" or "pharmaceutically acceptable amount" of the compound is that amount necessary or sufficient to treat or prevent a protein kinase-associated disorder, e.g. prevent the various morphological and somatic symptoms of a protein kinase-associated disorder, and/or a disease or condition described herein. In an example, an effective amount of a compound of the invention is the amount sufficient to treat a protein kinase-associated disorder in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes a pharmaceutically effective amount. A compound of the invention can be administered to the subject either prior to or after the onset of a protein kinase-associated disorder. Further, several divided dosages, as well as staggered dosages can be administered daily or sequentially, or the dose can be continuously infused, or can be a bolus injection.

Further, the dosages of the compound(s) of the invention can be proportionally increased or decreased as indicated by the exigencies of the therapeutic or prophylactic situation.

In one non-limiting embodiment, the phrase "pharmaceutically effective amount" refers to the amount of a compound of the present invention that, when administered to a subject, is effective to (1) at least partially alleviate, inhibit, prevent and/or ameliorate a condition, or a disorder or a disease (i) mediated by kinase enzymes c-Abl, BCR-Abl, c-kit and/or PDGFR, or (ii) associated with kinase enzymes c-Abl, BCR-Abl, c-kit and/or PDGFR activity, or (iii) characterized by abnormal activity of kinase enzymes c-Abl, BCR-Abl, c-kit and/or PDGFR; or (2) reduce or inhibit the activity of kinase enzymes c-Abl, BCR-Abl, c-kit and/or PDGFR; or (3) reduce or inhibit the expression of kinase enzymes c-Abl, BCR-Abl, c-kit and/or PDGFR. In another non-limiting embodiment, the phrase "pharmaceutically effective amount" refers to the amount of a compound of the present invention that, when administered to a subject, is effective to at least partially alleviate, inhibit, prevent and/or ameliorate cancer, e.g. pancreatic cancer, non-small cell lung cancer, gastrointestinal stromal tumor, or chronic myelogenous leukemia. In still another non-limiting embodiment, the term "pharmaceutically effective amount" refers to the amount of a compound of the present invention that, when administered to a cell, or a tissue, or a non-cellular biological material, or a medium, is effective to at least partially reduce or inhibit the activity of kinase enzymes c-Abl, BCR-Abl, c-kit and/or PDGFR; or at least partially reduce or inhibit the expression of kinase enzymes c-Abl, BCR-Abl, c-kit and/or PDGFR.

The effective amount can vary depending on such factors as the size and weight of the subject, the type of illness, or the particular organic compound. For example, the choice of the organic compound can affect what constitutes an "effective amount." One of ordinary skill in the art would be able to study the aforementioned factors and make the determination regarding the acceptable amount of the organic compound without undue experimentation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a protein kinase-associated disorder.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.
Synthetic Procedure Compounds of the present invention are prepared from commonly available compounds using procedures known to those skilled in the art, including any one or more of the following conditions without limitation:

Acid addition salts of the compounds of the invention are most suitably formed from pharmaceutically acceptable acids, and include for example those formed with inorganic acids e.g. hydrochloric, hydrobromic, sulphuric or phosphoric acids and organic acids e.g. succinic, malaeic, acetic or fumaric acid. Other non-pharmaceutically acceptable salts e.g. oxalates can be used for example in the isolation of the compounds of the invention, for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Particularly preferred salts are sodium, lysine and arginine salts of the compounds of the invention. Such salts can be formed by procedures well known and described in the art.

Other acids such as oxalic acid, which can not be considered pharmaceutically acceptable, can be useful in the preparation of salts useful as intermediates in obtaining a chemical compound of the invention and its pharmaceutically acceptable acid addition salt.

Metal salts of a chemical compound of the invention include alkali metal salts, such as the sodium salt of a chemical compound of the invention containing a carboxy group.

In vivo hydrolyzable esters or amides of certain compounds of the invention can be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of the invention having a free carboxy group can be esterified using standard conditions which can include activation followed by treatment with the desired alcohol in the presence of a suitable base.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany, 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals can, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Prodrugs

This invention also encompasses pharmaceutical compositions containing, and methods of treating protein kinase-associated disorders through administering, pharmaceutically acceptable prodrugs of compounds of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Any reference to a compound of the present invention is therefore to be understood as referring also to the corresponding pro-drugs of the compound of the present invention, as appropriate and expedient.

Kits

Advantageously, the present invention also provides kits for use by a consumer for treating disease. The kits comprise a) a pharmaceutical composition comprising an antibiotic and a pharmaceutically acceptable carrier, vehicle or diluent; and, optionally, b) instructions describing a method of using the pharmaceutical composition for treating the specific disease. The instructions may also indicate that the kit is for treating disease while substantially reducing the concomitant liability of adverse effects associated with antibiotic administration.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXEMPLIFICATION OF THE INVENTION

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

General Synthesis Processes

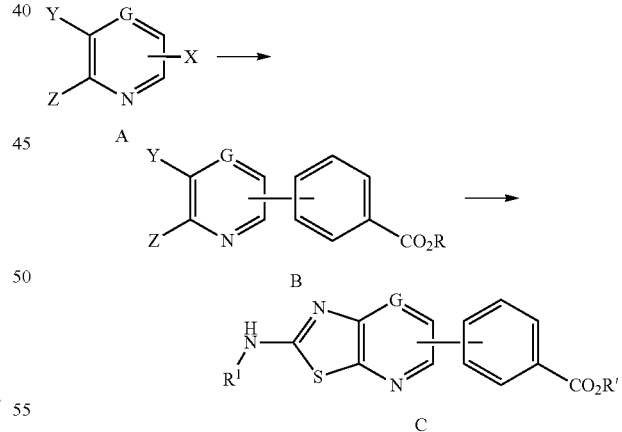

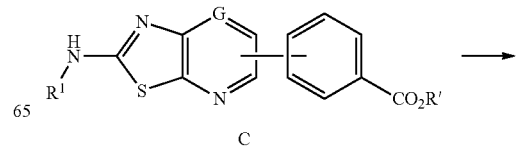

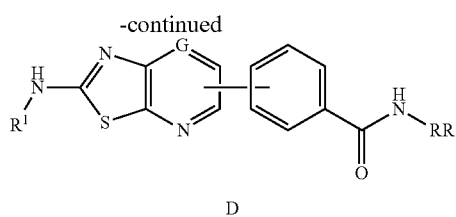

D

Scheme 3

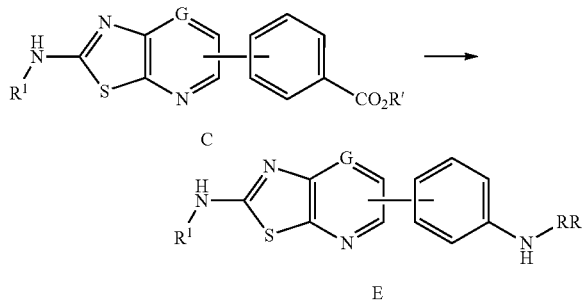

E

General Synthesis Methods

Non-limiting general synthesis procedures are depicted in Schemes 1-3. A variety of alternative conditions are known to those of skill in the art.

As shown in Scheme 1, the transformation of A to B involves coupling of the aryl compound A to an organometallic coupling partner (e.g., a boronic acid), using conditions well-known in the art (e.g., using a metal catalyst such as dichlorobis(triphenylphospine)palladium(II), a ligand such as 2-di-tert-butylphosphino-2',4',6'-triisopropylbiphenyl, a base such as $Na_2CO_3$, and a solvent such as dioxane). The transformation of B to C involves formation of a 2-aminothiazole moiety using conditions well-known in the art. For example, when Y is $NH_2$ and Z is a halogen, said compound may be treated with reagents such as cyclopropanecarbonyl chloride, ammonium thiocyanate, and potassium carbonate in solvents such as acetone and dioxane, at a temperature such as 50° C. The transformation of B to C also involves the replacement of the substituent R (e.g., $C_1$-$C_6$ alkyl) with the substituent R' (e.g., H) using conditions well-known in the art (e.g., using solvents such as water, methanol, and tetrahydrofuran, and reagents such as lithium hydroxide monohydrate and hydrochloric acid).

As shown in Scheme 2, the transformation of C to D involves the reaction of the carboxylic acid or carboxylic acid derivative C with a compound $RR-NH_2$ using conditions well-known in the art (e.g., using solvents such as DMF and reagents such as N,N-diisopropylethylamine and 2-(1H-7-azabenzotriazol-1-yl)-1,1,3,3-tetramethyl uronium hexafluorophosphate methanaminium at a temperature such as room temperature).

As shown in Scheme 3, the transformation of C to E involves conditions well-known in the art (e.g., using solvents such as toluene and reagents such as triethylamine and diphenylphosphorylazide), followed by reaction with a compound such as $RR-NH_2$, or a compound such as $RR-CO_2H$ using conditions well-known in the art (e.g., using solvents such as DMF and reagents such as N,N-diisopropylethylamine and 2-(1H-7-azabenzotriazol-1-yl)-1,1,3,3-tetramethyl uronium hexafluorophosphate methanaminium at a temperature such as room temperature).

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Referring to the examples that follow, compounds of the preferred embodiments were synthesized using the methods described herein, or other methods, which are known in the art.

Synthesis Examples

Example 1

3-(2-(cyclopropanecarboxamido)thiazolo[5,4-b]pyridin-5-yl)-N-(3-(trifluoromethyl)phenyl)benzamide

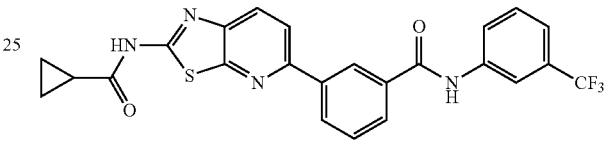

Part A

To a solution of 2-chloro-5-nitropyridine (5.23 g, 32.99 mmol) in dioxane (170 mL) was added 3-(ethoxycarbonyl) phenylboronic acid (6.28 g, 32.99 mmol) and 1N $Na_2CO_3$ aqueous solution (82.5 mL, 82.5 mmol). The reaction mixture was degassed using Argon gas for 20 min followed by the addition of dichlorobis(triphenylphospine)palladium(II) (1.38 g, 1.99 mmol) and 2-di-tert-butylphosphino-2',4',6'-triisopropylbiphenyl (1.26 g, 2.97 mmol). The reaction flask was put into the preheated oil-bath at 90° C. The reaction mixture was further stirred at 90° C. for a period of 10 h after which it was filtered and partitioned between ethyl acetate and water. The organic layer was separated and the aqueous layer was extracted with ethyl acetate. The combined organic extracts were washed with brine, dried over $MgSO_4$, filtered and concentrated. The crude product was purified by flash column chromatography using a 95:5 v/v hexane:ethyl acetate as solvent to afford ethyl 3-(5-nitropyridin-2-yl) benzoate (8.0 g, 89% yield) as a bright yellow solid.

$^1$H NMR 600 MHz (CDCl$_3$) δ 9.50 (s, 1H), 8.71 (s, 1H), 8.55 (d, J=7.8 Hz, 1H), 8.32 (d, J=7.2 Hz, 1H), 8.18 (d, J=7.2 Hz, 1H), 7.98 (d, J=8.4 Hz, 1H), 7.61 (t, J=7.2 Hz, 1H), 4.43 (q, 2H), 1.43 (t, 3H), MS m/z: 273.22 (M+1).

Part B

To a solution of ethyl 3-(5-nitropyridin-2-yl)benzoate (8.0 g, 29.40 mmol) in ethanol (150 mL) was added 5% Pd/C (800 mg). The reaction mixture was stirred under $H_2$ balloon pressure for 16 h. The reaction mixture was filtered and concentrated to give 6.9 g (97%, yield) of ethyl 3-(5-aminopyridin-2-yl)benzoate as a tan solid.

$^1$H NMR 600 MHz (CDCl$_3$) δ 8.52 (s, 1H), 8.18 (d, J=2.4 Hz, 1H), 8.13 (d, J=7.8 Hz, 1H), 8.00 (d, J=7.8 Hz, 1H), 7.59 (d, J=8.4 Hz, 1H), 7.49 (t, J=7.8 Hz, 1H), 7.06 (dd, J=2.4 Hz, J=8.4 Hz, 1H), 4.40 (q, 2H), 3.82 (s, 2H), 1.48 (t, 3H), MS m/z: 243.35 (M+1).

Part C

To a solution of ethyl 3-(5-aminopyridin-2-yl)benzoate (7.52 g, 31.06 mmol) in DMF (150 mL) was added N-bromosuccinimide (5.58 g, 31.37 mmol) at 0° C. for 5 min. The reaction mixture was quenched with satd. NaHCO₃ solution (150 mL) at 0° C. The mixture was partitioned between ethyl acetate and water. The organic layer was separated and the aqueous layer was extracted with ethyl acetate. The combined organic extracts were washed with brine, dried over MgSO₄, filtered and concentrated. The crude product was purified by flash column chromatography using a 85:15 v/v hexane:ethyl acetate as solvent to afford ethyl 3-(5-amino-6-bromopyridin-2-yl)benzoate (8.6 g, 86% yield) as a reddish brown solid.

¹H NMR 600 MHz (CDCl₃) δ 8.49 (s, 1H), 8.16 (d, J=7.8 Hz, 1H), 8.05 (d, J=7.8 Hz, 1H), 7.59 (d, J=7.8 Hz, 1H), 7.49 (t, J=7.8 Hz, 1H), 7.09 (d, J=8.4 Hz, 1H), 4.43 (q, 2H), 4.21 (s, 2H), 1.42 (t, 3H), MS m/z: 321.22 (M+1).

Part D

To a solution of ethyl 3-(5-amino-6-bromopyridin-2-yl)benzoate (10.44 g, 32.60 mmol) in NMP (150 mL) was added potassium ethyl xanthogenate (26.14 g, 163.11 mmol) and acetic acid (9.4 mL, 163.11 mmol). The reaction mixture was heated at 150° C. for 16 hours. The mixture was cooled to 50° C. and iodomethane (20.3 mL, 326 mmol) was added. The reaction mixture was further stirred for 30 minutes and partitioned between ethyl acetate and water. The organic layer was separated and the aqueous layer was extracted with ethyl acetate. The combined organic extracts were washed with brine, dried over MgSO₄, filtered and concentrated. The crude product was purified by flash column chromatography using a 85:15 v/v hexane:ethyl acetate as solvent to afford ethyl 3-(2-(methylthio)thiazolo[5,4-b]pyridin-5-yl)benzoate (7.6 g, 70% yield) as a bright brown solid.

¹H NMR 600 MHz (CDCl₃) δ 8.67 (t, J=1.8 Hz, 1H), 8.27 (dt, J=7.8 Hz, 1H), 8.13 (d, J=8.4 Hz, 1H), 8.10 (dt, J=7.8 Hz, 1H), 7.81 (d, J=8.4 Hz, 1H), 7.57 (t, 1H), 4.43 (q, 2H), 2.82 (s, 3H), 1.43 (t, 3H), MS m/z: 331.11 (M+1).

Part E

To a solution was ethyl 3-(2-(methylthio)thiazolo[5,4-b]pyridin-5-yl)benzoate (5.6 g, 16.9 mmol) in THF (25 mL) and methanol (25 mL) was added Oxone (41.55 g, 67.67 mmol) in water (25 mL). The reaction mixture was stirred for 16 hours at room temperature. The reaction mixture was filtered and concentrated to give 5.8 g (94%, yield) of ethyl 3-(2-(methylsulfonyl)thiazolo[5,4-b]pyridin-5-yl)benzoate as a bright brown solid.

¹H NMR 600 MHz (DMSO-d₆) δ 8.77 (m, 2H), 8.47 (d, J=7.8 Hz, 1H), 8.44 (d, J=8.4 Hz, 1H), 8.09 (d, J=7.8 Hz, 1H), 7.71 (t, J=7.8 Hz, 1H), 4.38 (q, 2H), 3.62 (s, 3H), 1.35 (t, 3H), MS m/z: 363.09 (M+1).

Part F

Ethyl 3-(2-(methylsulfonyl)thiazolo[5,4-b]pyridin-5-yl)benzoate (3.6 g, 9.91 mmol) was added to a 2N ammonia solution in IPA (24.8 mL, 49.57 mmol). The reaction mixture was heated at 90° C. and stirred for 30 h. The solvent was removed with in vacuo to give 2.7 g (91%, crude yield) ethyl 3-(2-aminothiazolo[5,4-b]pyridin-5-yl)benzoate as a yellow solid.

¹H NMR 600 MHz (DMSO-d₆) δ 8.58 (t, J=1.8 Hz, 1H), 8.26 (dt, J=1.2 Hz, J=7.8 Hz, 1H), 7.93 (dt, J=1.2 Hz, J=7.8 Hz, 1H), 7.89 (s, 2H), 7.87 (d, J=8.4 Hz, 1H), 7.68 (d, J=8.4 Hz, 1H), 7.58 (t, J=7.8 Hz, 1H), 4.34 (q, 2H), 1.33 (t, 3H), MS m/z: 300.19 (M+1).

Part G

To a solution of ethyl 3-(2-aminothiazolo[5,4-b]pyridin-5-yl)benzoate (800 mg, 2.67 mmol) in dichloromethane (13 mL) was added pyridine (0.74 mL, 4.05 mmol) and cyclopropanecarbonyl chloride (0.27 mL, 2.94 mmol). The reaction mixture was stirred for 4 hours. The reaction mixture was diluted with dichloromethane (20 mL) and washed with 1N aqueous HCl solution and brine, dried over MgSO₄, filtered and concentrated. The crude product was used for the next step without further purification.

¹H NMR 600 MHz (CDCl₃) δ 10.50 (s, 1H), 8.61 (s, 1H), 8.24 (d, J=7.8 Hz, 1H), 8.03 (d, J=7.8 Hz, 1H), 7.97 (d, J=8.4 Hz, 1H), 7.81 (d, J=8.4 Hz, 1H), 7.50 (t, 1H), 4.37 (q, 2H), 2.38 (m, 1H), 1.36 (t, 3H), 0.99 (m, 4H), MS m/z: 368.14 (M+1).

Part H

Ethyl 3-(2-(cyclopropanecarboxamido)thiazolo[5,4-b]pyridin-5-yl)benzoate (870 mg, 2.37 mmol) was dissolved in the mixture of water (3.0 mL), THF (3.0 mL) and methanol (3.0 mL) followed by the addition of lithium hydroxide monohydrate (497 mg, 11.85 mmol). The reaction mixture was stirred at room temperature for 16 h and was neutralized with 1N aqueous HCl until pH=6 (monitored with pH paper). Upon removal of the organic solvent in vacuo the resulting brown solid was collected and dried to give 620 mg (87% yield) of 3-(2-(cyclopropanecarboxamido)thiazolo[5,4-b]pyridin-5-yl)benzoic acid.

MS m/z: 340.19 (M+1).

Part I

To a solution 3-(2-(cyclopropanecarboxamido)thiazolo[5,4-b]pyridin-5-yl)benzoic acid (35 mg, 0.10 mmol) in DMF (1.0 mL) was added N,N-diisopropylethylamine (50 μL, 0.31 mmol), 2-(1H-7-azabenzotriazol-1-yl)-1,1,3,3-tetramethyl uronium hexafluorophosphate methanaminium (59 mg, 0.15 mmol) and 3-(trifluoromethyl)aniline (26 μL, 0.21 mmol). The reaction mixture was stirred at room temperature for 16 h. The crude product was diluted with DMSO (1 mL) and purified by preparative reverse-phase HPLC (acetonitrile/water gradient) to give title compound as a TFA salt form.

¹H NMR 600 MHz (DMSO-d₆) δ 12.81 (s, 1H), 10.67 (s, 1H), 8.66 (s, 1H), 8.34 (d, J=6.6 Hz, 1H), 8.24 (s, 1H), 8.19 (d, J=8.4 Hz, 1H), 8.16 (d, J=8.4 Hz, 1H), 8.07 (d, J=7.8 Hz, 1H), 8.00 (d, J=7.2 Hz, 1H), 7.76 (t, J=7.2 Hz, 1H), 7.59 (t, J=7.2 Hz, 1H), 7.45 (d, J=7.2 Hz, 1H), 2.01 (m, 1H), 0.96 (m, 4H), MS m/z: 483.22 (M+1).

Example 2

3-(2-(2-methyl-6-(piperazin-1-yl)pyrimidin-4-ylamino)thiazolo[5,4-b]pyridin-5-yl)-N-(3-(trifluoromethyl)phenyl)benzamide

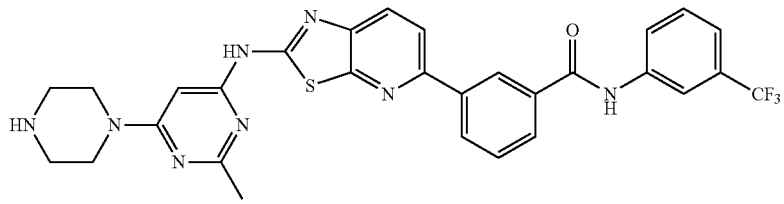 [SMILES: Cc1nc(Nc2nc3ccc(-c4cccc(C(=O)Nc5cccc(C(F)(F)F)c5)c4)nc3s2)cc(N2CCNCC2)n1]

Part A

To a solution of ethyl 3-(2-aminothiazolo[5,4-b]pyridin-5-yl)benzoate (400 mg, 1.34 mmol) in a mixture of water (2.0 mL), THF (2.0 mL) and methanol (2.0 mL) was added lithium hydroxide monohydrate (281 mg, 11.85 mmol). The reaction mixture was stirred at room temperature for 16 h and was neutralized with 1N aqueous HCl until pH=6 (monitored with pH paper). The organic solvent was removed in vacuo and the resulting brown solid was collected and dried to give 310 mg (85% yield) of 3-(2-aminothiazolo[5,4-b]pyridin-5-yl)benzoic acid.

MS m/z: 272.18 (M+1).

Part B

To a solution 3-(2-aminothiazolo[5,4-b]pyridin-5-yl)benzoic acid (310 mg, 1.14 mmol) in DMF (5.0 mL) was added N,N-diisopropylethylamine (0.56 mL, 3.42 mmol), 2-(1H-7-azabenzotriazol-1-yl)-1,1,3,3-tetramethyl uronium hexafluorophosphate methanaminium (649 mg, 1.71 mmol) and 3-(trifluoromethyl) aniline (0.28 mL, 2.28 mmol). The reaction mixture was stirred at room temperature for 16 h. The crude product was diluted with satd. NH$_4$Cl solution (10 mL). The resulting brown solid was collected and washed with water and dried to give 320 mg (67% yield) of the 3-(2-aminothiazolo[5,4-b]pyridin-5-yl)-N-(3-(trifluoromethyl)phenyl)benzamide.

$^1$H NMR 600 MHz (DMSO-d$_6$) δ 10.64 (s, 1H), 8.57 (s, 1H), 8.24 (m, 2H), 8.06 (d, J=7.8 Hz, 1H), 7.91 (m, 2H), 7.87 (m, 2H), 7.71 (d, J=7.8 Hz, 1H), 7.60 (m, 2H), 7.44 (d, J=7.2 Hz, 1H), MS m/z: 415.20 (M+1).

Part C

To a solution of 3-(2-aminothiazolo[5,4-b]pyridin-5-yl)-N-(3-(trifluoromethyl)phenyl)benzamide (33 mg, 0.079 mmol) in 2-butanol (1 mL) was added tert-butyl 4-(6-chloro-2-methylpyrimidin-4-yl)piperazine-1-carboxylate (24 mg, 0.079 mmol) and K$_2$CO$_3$ (82.5 mL). The reaction mixture was degassed using Argon gas for 20 min to which was added tris(dibenzylideneacetone)dipalladium(0) (4 mg, 7.1 µmol) and 9,9-dimethyl-4,5-bis(diphenylphosphino)xanthene (4 mg, 4.7 µmol). The reaction flask was put into the preheated oil-bath at 90° C. The reaction mixture was further stirred at 90° C. for a period of 4 hours after which, it was filtered and concentrated. The crude reaction mixture was dissolved in dichloromethane (1 mL) to which was added trifluoroacetic acid (30 µL, 0.40 mmol). The reaction mixture was stirred for 4 h. The majority of the organic solvent was removed in vacuo and the crude product was diluted with DMSO (1 mL) and purified by preparative HPLC to give the title compound as a TFA salt.

$^1$H NMR 600 MHz (DMSO-d$_6$) δ 11.75 (s, 1H), 10.67 (s, 1H), 8.82 (bs, 1H), 8.66 (s, 1H), 8.33 (d, J=7.2 Hz, 1H), 8.25 (s, 1H), 8.10 (d, J=9.0 Hz, 1H), 8.08 (m, 2H), 7.99 (d, J=7.8 Hz, 1H), 7.65 (t, 1H), 7.60 (t, 1H), 7.46 (d, J=7.2 Hz, 1H), 6.22 (s, 1H), 3.74 (m, 4H), 3.18 (m, 4H), 2.45 (s, 3H), MS m/z: 591.34 (M+1).

Example 3

3-(2-(3-piperidin-4-ylureido)thiazolo[5,4-b]pyridin-5-yl)-N-(3-(trifluoromethyl)phenyl)benzamide

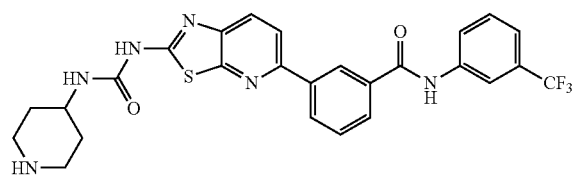 [SMILES: O=C(Nc1nc2ccc(-c3cccc(C(=O)Nc4cccc(C(F)(F)F)c4)c3)nc2s1)NC1CCNCC1]

To a solution of 3-(2-aminothiazolo[5,4-b]pyridin-5-yl)-N-(3-(trifluoromethyl)phenyl)benzamide (50 mg, 0.12 mmol) and triethylamine (25 µL, 0.18 mmol) in dichloromethane (1.0 mL) was added 4-nitrophenyl carbonochloridate (26 mg, 0.13 mmol) at 0° C. The reaction mixture was stirred at room temperature for 1 h. Tert-butyl 4-aminopiperidine-1-carboxylate (36 mg, 0.18 mmole) and triethylamine (25 µL, 0.18 mmol) were added to the reaction mixture. The reaction mixture was stirred for 4 h after which time the solvent was removed in vacuo. The reaction mixture was diluted with dichloromethane (5 mL) and washed with 1N aqueous HCl and brine. The organic layer was dried over MgSO$_4$ and concentrated in vacuo. To a solution of the crude mixture in dichloromethane (1 mL) was added trifluoroacetic acid (40 µL, 0.60 mmol). The reaction mixture was stirred for 4 h. The majority of the organic solvent was removed in vacuo and the crude product was diluted with DMSO (1 mL) and purified by preparative HPLC to give title compound in a TFA salt form.

$^1$H NMR 600 MHz (DMSO-d$_6$) δ 10.68 (s, 1H), 8.65 (s, 1H), 8.32 (d, J=8.4 Hz, 1H), 8.26 (s, 1H), 8.13 (m, 3H), 8.00 (d, J=7.2 Hz, 1H), 7.66 (t, 1H), 7.62 (t, 1H), 7.47 (d, J=8.4 Hz, 1H), 7.31 (d, J=6.0 Hz, 1H), 6.09 (d, J=7.2 Hz, 1H), 3.62 (m, 1H), 3.28 (m, 2H), 2.93 (m, 2H), 1.88 (m, 2H), 1.45 (m, 2H), MS m/z: 541.20 (M+1).

Example 4

N-(5-(3-(3-(trifluoromethyl)phenylcarbamoyl)phenyl)thiazolo[5,4-b]pyridin-2-yl) piperidine-4-carboxamide

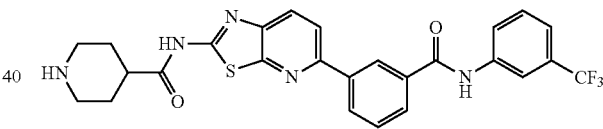

To a solution of 1-(tert-butoxycarbonyl)piperidine-4-carboxylic acid (15 mg, 0.07 mmol), 1-ethyl-3-(3-dimethylaminopropyl)carbodiimide hydrochloride (26 mg, 0.14 mmol), 4-dimethylaminopyridine (8 mg, 0.07 mmol) in DMF was added 3-(2-aminothiazolo[5,4-b]pyridin-5-yl)-N-(3-(trifluoromethyl)phenyl)benzamide (28 mg, 0.07 mmol). The reaction mixture was stirred at room temperature for 16 h. The reaction mixture was diluted with ethyl acetate (5 mL) and washed 1N aqueous HCl and brine. The organic layer was dried over MgSO$_4$ and the solvent removed in vacuo. To a solution of the crude mixture in dichloromethane (1 mL) was added trifluoroacetic acid (30 µL, 0.34 mmol). The reaction mixture was stirred for 4 h. The majority of the organic solvent was removed in vacuo and the crude product was diluted with DMSO (1 mL) and purified by preparative HPLC to give title compound in a TFA salt form.

$^1$H NMR 600 MHz (DMSO-d$_6$) δ 12.71 (s, 1H), 10.71 (s, 1H), 8.69 (s, 1H), 8.46 (m, 1H), 8.36 (d, J=8.4 Hz, 1H), 8.27 (s, 1H), 8.24 (d, J=8.4 Hz, 1H), 8.20 (d, J=9.0 Hz, 1H), 8.09 (d, J=7.8 Hz, 1H), 8.03 (d, J=7.2 Hz, 1H), 7.68 (t, 1H), 7.62 (t, 1H), 7.47 (d, J=7.8 Hz, 1H), 3.66 (m, 2H), 2.96 (m, 2H), 2.88 (m, 1H), 2.06 (m, 2H), 1.83 (m, 2H), MS m/z: 526.32 (M+1).

Example 5

N-(5-(3-(3-(4-((4-ethylpiperazin-1-yl)methyl)-3-(trifluoromethyl)phenyl)ureido)phenyl)thiazolo[5,4-b]pyridin-2-yl)cyclopropanecarboxamide

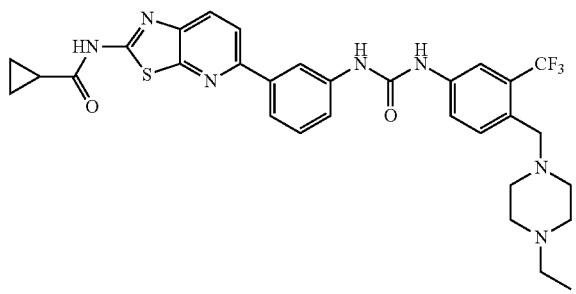 [SMILES: CCN1CCN(Cc2ccc(NC(=O)Nc3cccc(-c4ccc5nc(NC(=O)C6CC6)sc5n4)c3)cc2C(F)(F)F)CC1]

To a solution of 3-(2-(cyclopropanecarboxamido)thiazolo[5,4-b]pyridin-5-yl)benzoic acid (150 mg, 0.44 mmol) and triethylamine (90 µL, 0.66 mmol) in toluene (2 mL) was added diphenylphosphoryl azide (0.11 mL, 0.49 mmol). The resulting mixture was stirred at room temperature for 30 minutes and heated at 80° C. for 1 h. To a reaction mixture was added 4-((4-ethylpiperazin-1-yl)methyl)-3-(trifluoromethyl) aniline (121 mg, 0.42 mmol) and triethylamine (90 µL, 0.66 mmol). The reaction mixture was stirred at 80° C. for 2 h and most of organic solvent was removed in vacuo. The crude product was diluted with DMSO (3 mL) and purified by preparative HPLC to give the title compound as a TFA salt.

$^1$H NMR 600 MHz (CDCl$_3$) δ 8.51 (s, 1H), 7.83 (d, J=1.8 Hz, 1H), 7.48 (m, 2H), 7.19 (m, 3H), 7.12 (m, 2H), 6.85 (d, J=3.0 Hz, 1H), 6.49 (m, 1H), 6.19 (m, 2H), 3.84 (m, 1H), 3.78 (s, 3H), 3.46 (m, 2H), 3.19 (m, 1H), 2.90 (m, 2H), 1.99 (m, 2H), 1.69 (m, 2H), 1.19 (d, J=6.6 Hz, 6H), MS m/z: 624.36 (M+1).

Example 6

3-(2-(cyclopropanecarboxamido)thiazolo[5,4-b]pyridin-6-yl)-N-(4-((4-ethylpiperazin-1-yl)methyl)-3-(trifluoromethyl)phenyl)benzamide

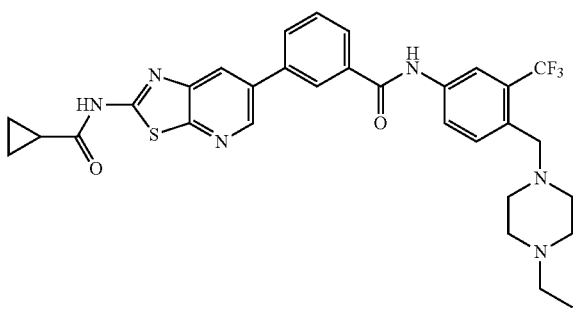 [SMILES: CCN1CCN(Cc2ccc(NC(=O)c3cccc(-c4cnc5sc(NC(=O)C6CC6)nc5c4)c3)cc2C(F)(F)F)CC1]

Part A

To a solution of 5-bromo-3-nitropyridin-2-amine (5.00 g, 23.97 mmol) in dioxane (115 mL) was added 3-(ethoxycarbonyl)phenylboronic acid (4.65 g, 23.97 mmol) and 1N Na$_2$CO$_3$ aqueous solution (92.2 mL, 92.2 mmol). The reaction mixture was degassed using Argon gas for 20 min followed by the addition of dichlorobis(triphenylphospine) palladium(II) (971 mg, 1.38 mmol) and 2-di-tert-butylphosphino-2',4',6'-triisopropylbiphenyl (881 mg, 2.07 mmol). The reaction flask was put into the preheated oil-bath at 90° C. The reaction mixture was further stirred at 90° C. for a period of 10 h after which it was filtered and partitioned between ethyl acetate and water. The organic layer was separated and the aqueous layer was extracted with ethyl acetate. The combined organic extracts were washed with brine, dried over MgSO$_4$, filtered and concentrated. The crude product was purified by flash column chromatography using a 90:10 v/v hexane:ethyl acetate as solvent to afford ethyl 3-(6-amino-5-nitropyridin-3-yl)benzoate (5.2 g, 78% yield) as a tan solid.

MS m/z: 288.23 (M+1).

Part B

A solution of tert-butylnitrite (3.23 mL, 27.17 mmol), anhydrous copper(II) chloride (2.9 g, 21.74 mmol) and anhydrous acetonitrile (90 mL) was warmed to 70° C. Ethyl 3-(6-amino-5-nitropyridin-3-yl)benzoate (5.2 g, 18.11 mmol) was then added portionwise over a period 10 minutes to the reaction solution. The reaction mixture was maintained at 70° C. for 2 hours and then allowed to cool to room temperature. The reaction mixture was then poured into 110 mL of 20% aqueous HCl solution, followed by extraction with ethyl acetate. The organic extracts were washed with brine, dried over MgSO$_4$, filtered and concentrated in vacuo. The crude product was purified by flash column chromatography using a 95:5 v/v hexane:ethyl acetate as solvent to afford ethyl 3-(6-chloro-5-nitropyridin-3-yl)benzoate (3.4 g, 61% yield) as a tan solid.

MS m/z: 307.16 (M+1).

Part C

To a solution of ethyl 3-(6-chloro-5-nitropyridin-3-yl)benzoate (3.0 g, 9.08 mmol) in ethyl acetate (50 mL) was added Tin(II) chloride dihydrate (11.06 g, 49.01 mmol). The reaction mixture was stirred for 10 hours at room temperature. The reaction mixture was cooled to 0° C. and then NH$_4$OH solution was added to the reaction mixture and it was allowed to reach around pH=5 (monitored with pH paper). The reaction mixture was neutralized with Na$_2$CO$_3$ and the resulting white solid was filtered and washed with ether (100 mL) three times. The organic layer was concentrated to give 2.3 g (84%, yield) of ethyl 3-(5-amino-6-chloropyridin-3-yl)benzoate as a tan solid.

MS m/z: 277.20 (M+1).

Part D

Ammonium thiocyanate (303 mg, 3.98 mmol) was dissolved in acetone (10 mL) and heated to 50° C. and which point a clear solution was obtained. Cyclopropanecarbonyl chloride (0.37 mL, 3.98 mmol) was added dropwise and the resulting white suspension was refluxed for 20 minutes. Ethyl 3-(5-amino-6-chloropyridin-3-yl)benzoate (1.0 g, 3.62 mmol) dissolved in dioxane (18 mL) and K$_2$CO$_3$ (2.0 g, 14.48 mmol) were added to the reaction mixture. The reaction mixture was refluxed for 8 hours at 120° C. After cooling to room temperature, the reaction solution was poured into ice water and the resulting tan solid was collected by filtration, washed with water and ether and dried. The crude product was used for the next step without further purification.

$^1$H NMR 600 MHz (DMSO-d$_6$) δ 8.68 (d, J=1.8 Hz, 1H), 8.49 (s, 1H), 8.26 (d, J=1.8 Hz, 1H), 8.23 (s, 1H), 8.03 (d, J=7.2 Hz, 1H), 7.97 (d, J=7.8 Hz, 1H), 7.64 (t, 1H), 4.32 (q, 2H), 1.99 (m, 1H), 1.33 (t, 3H), 0.93 (m, 4H), MS m/z: 368.22 (M+1).

Part E

Ethyl 3-(2-(cyclopropanecarboxamido)thiazolo[5,4-b]pyridin-6-yl)benzoate (900 mg, 2.45 mmol) was dissolved in a mixture of water (4.0 mL), THF (4.0 mL) and methanol (4.0 mL) and lithium hydroxide monohydrate (513 mg, 12.23 mmol) was added. The reaction mixture was stirred at room temperature for 16 h and was neutralized with 1N aqueous HCl until pH 6 (monitored with pH paper). The organic solvent was removed in vacuo and the resulting brown solid was collected by filtration and dried to give 720 mg (86% yield) of 3-(2-(cyclopropanecarboxamido)thiazolo[5,4-b]pyridin-5-yl)benzoic acid.

MS m/z: 340.20 (M+1).

Part F

To a solution 3-(2-(cyclopropanecarboxamido)thiazolo[5,4-b]pyridin-5-yl)benzoic acid (40 mg, 0.12 mmol) in DMF (1.0 mL) was added N,N-diisopropylethylamine (60 µL, 0.35 mmol), 2-(1H-7-azabenzotriazol-1-yl)-1,1,3,3-tetramethyl uronium hexafluorophosphate methanaminium (90 mg, 0.24 mmol) and 4-((4-ethylpiperazin-1-yl)methyl)-3-(trifluoromethyl)aniline (41 mg, 0.14 mmol). The reaction mixture was stirred at room temperature for 16 h. The crude product was diluted with DMSO (1 mL) and purified by preparative reverse-phase HPLC (acetonitrile/water gradient) to give title compound as a TFA salt form.

$^1$H NMR 600 MHz (DMSO-$d_6$) δ 12.87 (s, 1H), 10.65 (s, 1H), 9.74 (bs, 1H), 8.47 (d, J=1.8 Hz, 1H), 8.37 (s, 1H), 8.23 (s, 1H), 8.11 (d, J=8.4 Hz, 1H), 8.06 (d, J=7.8 Hz, 1H), 8.01 (d, J=7.8 Hz, 1H), 7.73 (d, J=8.4 Hz, 1H), 7.68 (t, 1H), 3.69 (s, 2H), 3.48 (m, 2H), 3.14 (q, 2H), 2.98 (m, 4H), 2.45 (m, 2H), 2.05 (m, 1H), 1.20 (m, 3H), 0.99 (m, 4H), MS m/z: 609.37 (M+1).

Example 7

4-(2-(cyclopropanecarboxamido)thiazolo[4,5-b]pyrazin-6-yl)-N-(4-((4-ethylpiperazin-1-yl)methyl)-3-(trifluoromethyl)phenyl)benzamide

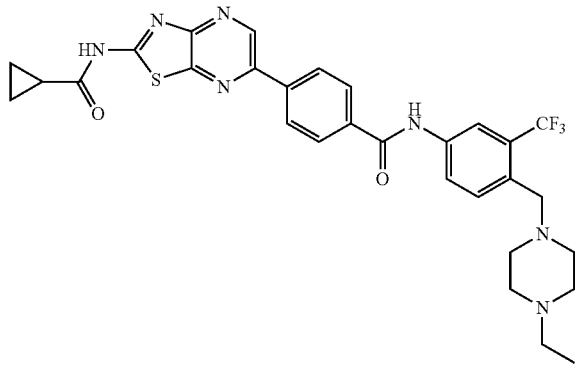 [SMILES: CCN1CCN(Cc2ccc(NC(=O)c3ccc(-c4cnc5nc(NC(=O)C6CC6)sc5n4)cc3)cc2C(F)(F)F)CC1]

Part A

A mixture of ammonium thiocyanate (668 mg, 8.77 mmol) and acetone (10 mL) was heated until a clear solution was obtained at 50° C. Cyclopropanecarbonyl chloride (0.80 mL, 8.77 mmol) was added dropwise and the resulting white suspension was refluxed for 20 minutes. 3,5-dibromopyrazin-2-amine (2.0 g, 7.97 mmol) dissolved in acetone (18 mL) and $K_2CO_3$ (4.4 g, 31.88 mmol) were added to the reaction mixture. The reaction mixture was refluxed for 4 hours. After cooling to room temperature, the reaction solution was poured into ice water and the resulting tan solid was collected by filtration, washed with water and ether and dried. The crude product (1.6 g, 67% yield) was used for the next step without further purification.

$^1$H NMR 600 MHz (DMSO-$d_6$) δ 13.28 (s, 1H), 8.71 (s, 1H), 2.02 (m, 1H), 1.02 (m, 4H), MS m/z: 298.98 (M+1).

Part B

To a solution of N-(6-bromothiazolo[4,5-b]pyrazin-2-yl)cyclopropanecarboxamide (1.00 g, 3.36 mmol) in dioxane (16 mL) was added 4-boronobenzoic acid (557 mg, 3.36 mmol) and 1N $Na_2CO_3$ aqueous solution (13.2 mL, 13.2 mmol). The reaction mixture was degassed using Argon gas for 20 min followed by the addition of dichlorobis(triphenylphospine) palladium(II) (141 mg, 0.20 mmol) and 2-di-tert-butylphosphino-2',4',6'-triisopropylbiphenyl (128 mg, 0.30 mmol). The reaction flask was put into the preheated oil-bath at 120° C. The reaction mixture was further stirred at 120° C. for a period of 10 h after which it was filtered. 2.0 N NaOH solution was added to the filtrate until pH 10 (monitored with pH paper) and then partitioned between ethyl acetate and water. A 6.0 N aqueous HCl solution was added to the water layer until pH 6 (monitored with pH paper). The resulting brown solid was collected by filtration and dried to give 740 mg (64% yield) of 4-(2-(cyclopropanecarboxamido)thiazolo[4,5-b]pyrazin-6-yl)benzoic acid.

MS m/z: 341.18 (M+1).

Part C

To a solution 4-(2-(cyclopropanecarboxamido)thiazolo[4,5-b]pyrazin-6-yl)benzoic acid (50 mg, 0.15 mmol) in DMF (1.0 mL) was added N,N-diisopropylethylamine (70 µL, 0.44 mmol), 2-(1H-7-azabenzotriazol-1-yl)-1,1,3,3-tetramethyl uronium hexafluorophosphate methanaminium (112 mg, 0.29 mmol) and 4-((4-ethylpiperazin-1-yl)methyl)-3-(trifluoromethyl)aniline (51 mg, 0.17 mmol). The reaction mixture was stirred at room temperature for 16 h. The crude product was diluted with DMSO (1 mL) and purified by preparative reverse-phase HPLC (acetonitrile/water gradient) to give the title compound as a TFA salt.

$^1$H NMR 600 MHz (DMSO-$d_6$) δ 13.21 (s, 1H), 10.65 (s, 1H), 9.56 (bs, 1H), 9.29 (s, 1H), 8.36 (d, J=7.2, 1H), 8.24 (s, 1H), 8.13 (m, 3H), 7.72 (d, J=7.8 Hz, 1H), 3.69 (s, 2H), 3.46 (m, 2H), 3.13 (m, 2H), 2.98 (m, 4H), 2.40 (m, 2H), 2.06 (m, 1H), 1.19 (m, 3H), 1.02 (m, 4H), MS m/z: 610.25 (M+1).

Example 8

3-(2-(cyclopropanecarboxamido)thiazolo[4,5-b]pyrazin-6-yl)-N-(4-((4-ethylpiperazin-1-yl)methyl)-3-(trifluoromethyl)phenyl)benzamide

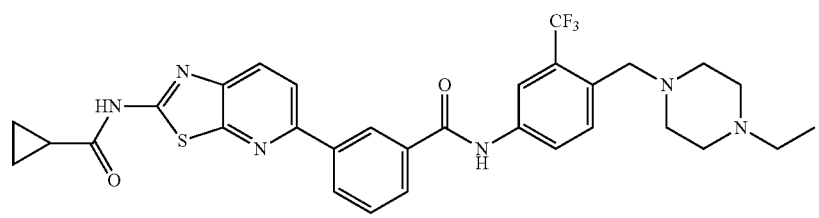 [SMILES: CCN1CCN(Cc2ccc(NC(=O)c3cccc(-c4ccc5nc(NC(=O)C6CC6)sc5n4)c3)cc2C(F)(F)F)CC1]

To a solution 3-(2-(cyclopropanecarboxamido)thiazolo[5,4-b]pyridin-5-yl)benzoic acid (40 mg, 0.12 mmol) in DMF (1.0 mL) was added N,N-diisopropylethylamine (60 μL, 0.35 mmol), 2-(1H-7-azabenzotriazol-1-yl)-1,1,3,3-tetramethyl uronium hexafluorophosphate methanaminium (90 mg, 0.24 mmol) and 4-((4-ethylpiperazin-1-yl)methyl)-3-(trifluoromethyl)aniline (41 mg, 0.14 mmol). The reaction mixture was stirred at room temperature for 16 h. The crude product was diluted with DMSO (1 mL) and purified by preparative reverse-phase HPLC (acetonitrile/water gradient) to give title compound as a TFA salt form.

$^1$H NMR 600 MHz (DMSO-$d_6$) δ 12.87 (s, 1H), 10.65 (s, 1H), 9.74 (bs, 1H), 8.47 (d, J=1.8 Hz, 1H), 8.37 (s, 1H), 8.23 (s, 1H), 8.11 (d, J=8.4 Hz, 1H), 8.06 (d, J=7.8 Hz, 1H), 8.01 (d, J=7.8 Hz, 1H), 7.73 (d, J=8.4 Hz, 1H), 7.68 (t, 1H), 3.69 (s, 2H), 3.48 (m, 2H), 3.14 (q, 2H), 2.98 (m, 4H), 2.45 (m, 2H), 2.05 (m, 1H), 1.20 (m, 3H), 0.99 (m, 4H), MS m/z: 609.37 (M+1).

Example 9

3-(2-(cyclopropanecarboxamido)thiazolo[5,4-b]pyridin-5-yl)-N-(3-(4-methyl-1H-imidazol-1-yl)-5-(trifluoromethyl)phenyl)benzamide

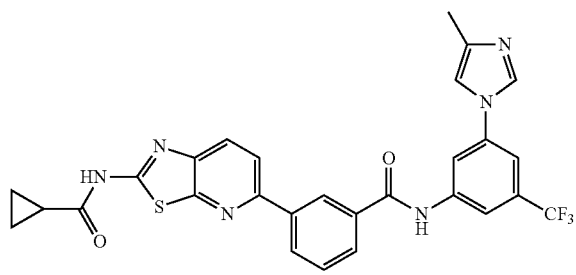 [SMILES: Cc1cn(-c2cc(NC(=O)c3cccc(-c4ccc5nc(NC(=O)C6CC6)sc5n4)c3)cc(C(F)(F)F)c2)cn1]

To a solution 3-(2-(cyclopropanecarboxamido)thiazolo[5,4-b]pyridin-5-yl)benzoic acid (40 mg, 0.12 mmol) in DMF (1.0 mL) was added N,N-diisopropylethylamine (60 μL, 0.35 mmol), 2-(1H-7-azabenzotriazol-1-yl)-1,1,3,3-tetramethyl uronium hexafluorophosphate methanaminium (90 mg, 0.24 mmol) and 3-(4-methyl-1H-imidazol-1-yl)-5-(trifluoromethyl)benzenamine (34 mg, 0.14 mmol). The reaction mixture was stirred at room temperature for 16 h. The crude product was diluted with DMSO (1 mL) and purified by preparative reverse-phase HPLC (acetonitrile/water gradient) to give title compound as a TFA salt form.

$^1$H NMR 600 MHz (DMSO-$d_6$) δ 12.83 (s, 1H), 10.84 (s, 1H), 8.71 (s, 1H), 8.37 (d, J=7.2 Hz, 1H), 8.31 (s, 1H), 8.22 (m, 2H), 8.18 (d, J=8.4 Hz, 1H), 8.04 (d, J=7.8 Hz, 1H), 7.74 (s, 1H), 7.69 (t, 1H), 7.49 (s, 1H), 3.29 (s, 3H), 2.17 (s, 3H), 2.03 (m, 1H), 0.99 (m, 4H), MS m/z: 563.18 (M+1).

Chemical Compounds and Biologic Reagents

All compounds were initially dissolved in DMSO to make 10 mM stock solutions, and then were serially diluted to obtain final concentrations for in vitro experiments.

Cell Lines and Cell Culture

Ba/F3.p210 cells were obtained by transfecting the IL-3-dependent marine hematopoietic Ba/F3 cell line with a pGD vector containing p210BCR-ABL (B2A2) cDNA (Daley and Baltimore, 1988; Sattler et al., 1996; Okuda et al., 1996). Murine hematopoietic 32D cells were transduced with retrovirus to express p210 Bcr-ABL (32D.p210 cells) (Matulonis et al., 1993); the 32D-T315I cell line was transfected by electroporation with the imatinib resistant BCR-ABL construct (pCI-neo Mammalian Expression Vector; Promega (#E1841) harboring the point mutation T315I (Weisberg et al., 2005). Ba/F3 cells were stably transfected by electroporation with imatinib-resistant BCR-ABL constructs (pCI-neo Mammalian Expression Vector; Promega (#E1841) harboring the point mutations T315I, F317L, F486S, and M351T; transfectants were selected for neomycin resistance and IL-3-independent growth (Weisberg et al., 2005). Ba/F3 cells were stably transfected by electroporation with BCR-ABL point mutants identified in a random mutagenesis screen for BCR-ABL point mutants conferring resistance to nilotinib: Q252H, E292K, Y253C, Y253H, E255K, and V289L (Ray et al., 2007). Ba/F3 cells were made to express Tel-PDGFRβ as described by Golub et al., 1994, and Carroll et al., 1996. Constructs of D842V-PDGFRα and V561D-PDGFRα cDNA cloned into pcDNA3.1 were stably transfected into Ba/F3 cells by electroporation, and cells were selected for neomycin resistance and IL3-independent growth as described by Weisberg et al., 2006.

All cell lines were cultured with 5% $CO_2$ at 37° C. in RPMI (Mediatech, Inc., Herndon, Va.) with 10% fetal calf serum (FCS) and supplemented with 1% L-glutamine. Parental Ba/F3 cells were similarly cultured with 15% WEHI-conditioned medium as a source of IL-3. Transfected cell lines were cultured in media supplemented with 1 mg/ml G418.

Antibodies and Immunoblotting and Immunoprecipitation

Anti-p-Tyr (clone 4G10, Upstate Biotechnology, NY) was used at 1:1000 for immunoblotting. The ABL antibody (clone 24-21, Calbiochem, San Diego, Calif.) was used at 1:1000 for immunoblotting. The KIT antibody (C-19, Santa Cruz Biotechnology, CA) was used at 1:1000 for immunoblotting. The phospho-KIT antibody (Tyr719, Cell Signaling, Danvers, Mass.) was used at 1:1000 for immunoblotting. PDGFRA antibody (C-20, Santa Cruz Biotechnology, CA) was used at 1:200 for immunoblotting. The monoclonal anti-β-actin antibody (clone AC-15) (Sigma-Aldrich, St. Louis, Mo.) was used at a 1:2000 dilution. Cells were lysed in lysis buffer (0.02 M Tris [pH 8.0], 0.15 M NaCl, 10% glycerol, 1% NP-40 (wt/vol), 0.1 M NaF, 1 mM phenylmethylsulfonyl fluoride, 1 mM sodium orthovanadate, 40 μg/ml leupeptin, and 20 μg/ml aprotinin). Protein lysates were incubated for 25 min on ice, with vortexing at 5 min intervals, and then centrifuged for 15 min at 12,000× g. Supernatants were saved, and the Bio-Rad Protein Assay was used to determine protein yields (Bio-Rad Laboratories, Hercules, Calif.). Equivalent amounts of protein were subsequently loaded directly onto a gel for immunoblotting experiments. For immunoprecipitation, cell lysates were incubated with FLT3/Flk-2 (C-20) antibody and protein A Sepharose overnight with rocking at 4° C. As a control, cell lysates were also incubated with protein A Sepharose beads alone. Following incubation, immune complexes were washed 2× with lysis buffer, 2× with 1× PBS, and were dissolved in Laemmeli's sample buffer by boiling for 5 min. For immunoblotting and immunoprecipitation, whole cell lysates and immune complexes, respectively, were resolved on a sodium dodecyl sulfate (SDS)-7.5% polyacrylamide gel. Following this, protein was electrophoretically transferred to a Protran nitrocellulose transfer and immobilization membrane (Schleicher and Schuell, Dassel, Germany). The membrane was then blocked overnight at 4° C. with 5% nonfat dry milk in 1×TBS (10 mM Tris-HCl [pH 8.0], 150 mM NaCl) and then probed for 2 hr at 25° C. with pTYR, antibody or overnight at 4 C with FLT3/Flk-2 (C-20) antibody in 1×TBST buffer (10 mM Tris-HCl [pH 8.0], 150 mM NaCl, 0.05% Tween20). Following 3 washes with 1×TBST, membranes were incubated for 1 hr at 25° C. with anti-mouse immunoglobulin (horseradish peroxidase-linked whole antibody from sheep) or anti-rabbit immunoglobulin (horseradish peroxidase linked whole antibody from donkey) (Amersham Life Science, Inc., Arlington Heights, Ill.). The membrane was washed 5× in 1×TBST buffer, with 5 min intervals between buffer changes, and bound antibodies were detected with enhanced luminol and oxidizing reagent as specified by the manufacturer (NEN Life Science Products, Boston, Mass.). Bound antibodies were removed with stripping buffer (2% SDS, 0.0625 mol/L Tris [pH 6.8], and 0.7% 2-mercaptoethanol) 50° C. for 30 min. The filter was then probed with additional antibodies.

Cell Cycle Analysis

Cell cycle analysis was performed using approximately 500,000 cells, which were centrifuged at 1500 rpm for 5 min, washed in PBS, and the pellet re-suspended in 500 µl of propidium iodide solution (50 µg/ml propidium iodide, 0.1% NP-40, 0.1% sodium citrate). The mixture was stored in the dark at 4° C. for a minimum of 15 min, and then analyzed by flow cytometry. Apoptosis of drug-treated cells was measured using the Annexin-V-Fluos Staining Kit (Boehringer Mannheim, Indianapolis).

Apoptosis Assay

Cells cultured in the presence or absence of drug were washed 1× with phosphate-buffered saline (PBS) and centrifuged for 5 min at 1500 rpm. Washed cell pellets were re-suspended in 100 µl of 20% Annexin-V-fluorescein labeling reagent and 20% propidium iodide (PI) in HEPES buffer. Cells were incubated for 15 min at room temperature, followed by dilution with 0.8 ml of HEPES buffer. Samples were then analyzed by flow cytometry. As controls, cells were incubated for 15 min with PI alone, Annexin-V-fluorescein labeling reagent alone, or HEPES buffer, and then diluted with HEPES buffer and analyzed by flow cytometry.

Drug Combination Studies

For drug combination studies, compounds were added simultaneously at fixed ratios to cells, and cell viability was determined by trypan blue exclusion and expressed as the function of growth affected (FA) drug-treated versus control cells. Synergy was assessed by Calcusyn software (Biosoft, Ferguson, Mo. and Cambridge, UK), using the Chou-Talalay method (Chou and Talalay, 1984). The combination index= $[D]_1[D_x]_1+[D]_2/[D_x]_2$, where $[D]_1$ and $[D]_2$ are the concentrations required by each drug in combination to achieve the same effect as concentrations $[D_x]_1$ and $[D_x]_2$ of each drug alone. Values less than one indicate synergy, whereas values greater than one indicate antagonism.

Bioluminescent Imaging

Cells were transduced with a retrovirus encoding firefly luciferase (MSCV-Luc), and selected with puromycin at 2 µg/ml to generate 32D.p210-luc+ cells, as described by Weisberg et al., 2005. Ba/F3-KIT-T670I cells were transduced with MSCV-luc-neo vector following the same protocol as described by Weisberg et al., 2005.

Kinase Screen

KINOMEscan™ (Ambit Biosciences, San Diego, Calif.), a high-throughput method for screening small molecular agents against a large panel of human kinases, was utilized for compound 2. The technology is a competition binding assay that profiled the selectivity of compound 2 against 350 kinases, each fused to a proprietary tag. The quantity of each kinase bound to an immobilized, active site-directed ligand was measured in the presence and absence of compound 2.

FIG. 1 depicts: A) The chemical structure of compound 2 (Table A) with substructure names indicated; B) Kinase selectivity of compound 2 based on screening 400 kinases. Kinases where significant binding affinity was detected at 10 µM were retested in dose-response format to determine a dissociation constant. The size of the red circle is proportion to $K_d$. Numerical $K_d$'s are listed in Table IV; and C) Crystal structure of compound 2 with Src kinase domain showing the ATP-binding site. Compound 2 (blue sticks) and Src (green ribbon) are shown as are hydrogen-bonding interactions (orange hatched lines) with hinge residues (Y340, M341), αC-helix (E310), DFG-motif (D404) and V383. The compound binds in the "DFG-out" conformation as evident by the position of F405. Ample space is available adjacent to the gatekeeper residue T338 providing a rationale for the tolerance for a larger amino acid at this position.

TABLE I

Table I. Relative IC50 ranges for compound 2 in BCR-Abl-, kit-, and PDGFR-expressing cell lines. All assays performed were 2.5-3 days in duration, except for D842V-PDGFRα and V561D-PDGFRα, and Ba/F3-Y572C, Ba/F3-N841I, and Ba/F3-D835Y, which were 2 day experiments.

| Cell Line | 2 (µM) |
|---|---|
| BCR-Abl | |
| Ba/F3 -p210 | 0.05 < 0.1 |
| Ba/F3 -T3151 | 0.05 < 0.1 |
| Ba/F3-Y253H | 0.5 < 1 |
| Ba/F3-E255K | 0.5 < 1 |
| Ba/F3-Q252H | 0.05 < 0.1 |
| Ba/F3-V289L | 0.5 < 1 |
| Ba/F3-E292K | 0.5 < 1 |
| Ba/F3-Y253C | <0.1 |
| Ba/F3-M351T | 0.5 < 1 |
| Ba/F3-F317L | 0.5 < 1 |
| Ba-F3-F486S | 0.5 < 1 |
| Kit | |
| Ba/F3-insAY | >1 |
| Ba/F3-insAY + V654A | >1 |
| Ba/F3-insAY + T670I | ≥1 |
| Ba/F3-V6559D | 0.25-0.5 |
| Ba/F3-delWK | 0.0125-0.025 |
| Ba/F3-delWK + V654A | 0.025-0.05 |
| Ba/F3-delWK + T670I | 0.025-0.05 |
| Ba/F3-delWK + Y823D | 0.5-1 |
| Ba/F3 -T670I | 0.25 |
| PDGFR | |
| Ba/F3-TEL/PDGFRβ | <0.1 |
| Ba/F3- PDGFRβ-T681M | — |
| Ba/F3- PDGFRβ-T681I | >1 |
| Ba/F3- PDGFRα-T674M | — |
| Ba/F3- PDGFRα-T674I | — |
| Ba/F3- PDGFRα-D842V | 1 |
| Ba/F3- PDGFRα-V561D | >1 |

TABLE II

Table II. Effect of compound 2 on cell cycle progression of BCR-Abl, BCR-Abl-T315I-, kit-T670I-, PDGFRα-T674M-, and PDGFRα-T674I-expressing cells following 24 hours of treatment.

| Cell Line | Phase | 2 (0 µM) | 2 (0.01 µM) | 2 (0.1 µM) | 2 (1.0 µM) |
|---|---|---|---|---|---|
| 32D-BCR-Abl | % G0G1 | 37.11 | 42.62 | 76.52 | 77.44 |
| | % G2M | 6.88 | 9.56 | 3.78 | 9.07 |
| | % S | 56 | 47.82 | 19.71 | 13.49 |
| 32D-BCR-Abl-T3151 | % G0G1 | 25.95 | 36.96 | 46.35 | 73.13 |
| | % G2M | 14.59 | 22.64 | 10.54 | 9.29 |
| | % S | 59.46 | 40.40 | 43.11 | 17.59 |

TABLE II-continued

Table II. Effect of compound 2 on cell cycle progression of BCR-Abl, BCR-Abl-T315I-, kit-T670I-, PDGFRα-T674M-, and PDGFRα-T674I-expressing cells following 24 hours of treatment.

| Cell Line | Phase | 2 (0 μM) | 2 (0.01 μM) | 2 (0.1 μM) | 2 (1.0 μM) |
|---|---|---|---|---|---|
| Ba/F3-kit-T670I | % G0G1 | 36.62 | 35.2 | 29.01 | 52.57 |
|  | % G2M | 13.09 | 14.62 | 16.54 | 10.05 |
|  | % S | 50.30 | 50.19 | 54.45 | 37.38 |
| Ba/F3-PDGFRα-T674M | % G0G1 | 36.2 | 40.81 | 72.37 | 79.92 |
|  | % G2M | 10.36 | 7.41 | 3.62 | 2.46 |
|  | % S | 53.44 | 51.78 | 24.01 | 17.61 |
| Ba/F3-PDGFRα-T674I | % G0G1 | 49.92 | 57.30 | 64.90 | 77.55 |
|  | % G2M | 6.46 | 5.98 | 5.82 | 7.16 |
|  | % S | 43.61 | 36.72 | 29.28 | 15.29 |

TABLE III

Table III. Induction of apoptosis by compound 2 in BCR-Abl, BCR-Abl-T315I-, kit-T670I-, PDGFRα-T674M-, and PDGFRα-T674I-expressing cells following approximately 3 days of treatment.

| Cell Line | Phase | 2 (0 μM) | 2 (0.01 μM) | 2 (0.1 μM) | 2 (1.0 μM) |
|---|---|---|---|---|---|
| 32D-BCR-Abl | Viable | 96.5 | 94 | 47.1 | 4.6 |
|  | Apoptotic | 3.3 | 5.8 | 52.3 | 95.3 |
|  | Necrotic | 0.2 | 0.2 | 0.6 | 0.1 |
| 32D-BCR-Abl-T315I | Viable | 96.6 | 90.88 | 89.9 | 27.2 |
|  | Apoptotic | 3.4 | 9.0 | 9.8 | 72.7 |
|  | Necrotic | 0 | 0.1 | 0.3 | 0 |
| Ba/F3-kit-T670I | Viable | 96.8 | 97.7 | 96.9 | 91.6 |
|  | Apoptotic | 3.2 | 2.3 | 3.1 | 8.4 |
|  | Necrotic | 0 | 0 | 0 | 0 |
| Ba/F3-PDGFRα-T674M | Viable | 92.2 | 91 | 34.7 | 13.2 |
|  | Apoptotic | 7.8 | 9 | 65.2 | 86.80 |
|  | Necrotic | 0 | 0 | 0 | 0.1 |
| Ba/F3-PDGFRα-T674I | Viable | 87.3 | 61.9 | 15.2 | 5.8 |
|  | Apoptotic | 12.8 | 38.1 | 84.7 | 94.1 |
|  | Necrotic | 0 | 0.1 | 0.2 | 0 |

TABLE IV

Table IV. Kinase selectivity of compound 2 (Table A).

| Kinase | $K_d$ (nM) |
|---|---|
| ABL1 | 3.3 |
| ABL1(T315I) | 1.2 |
| BRAF | 36 |
| CDK11 | 32 |
| CDK2 | 840 |
| CDK3 | 250 |
| CDK5 | 150 |
| CDK7 | 13 |
| DDR1 | 3.4 |
| FLT1 | 74 |
| FLT3 | 2.3 |
| FLT4 | 31 |
| HIPK1 | 34 |
| KIT | 2.9 |
| LOK | 9.5 |
| p38-gamma | 100 |
| PDGFRA | 7.7 |
| PDGFRB | 1.8 |
| RET | 5.6 |
| TIE2 | 57 |
| VEGFR2 | 58 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

The entire contents of all patents, published patent applications and other references cited herein are hereby expressly incorporated herein in their entireties by reference.

The invention claimed is:

1. A compound of the Formula I:

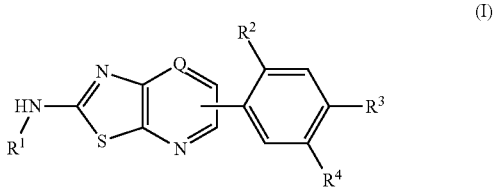

(I)

or a pharmaceutically acceptable salt, enantiomer, stereoisomer, rotamer, tautomer, diastereomer, or racemate thereof;

wherein

Q is CH or N;

$R^1$ is H, C(O)—$C_{3-6}$-cycloalkyl, aryl, heteroaryl, C(O)N(H)-heteroaryl, C(O)-heteroaryl, C(O)-heterocycle, C(O)-aryl, $CO_2$—$C_{1-6}$-alkyl, $C_{3-6}$-cycloalkyl, or C(O)—$C_{1-6}$-alkyl-heterocycle, wherein the aryl or heteroaryl groups can be substituted or unsubstituted;

$R^2$ is H, $C_{1-6}$-alkyl, $C_{1-6}$-alkoxy, or halogen;

$R^3$ is H, C(O)—N(H)-aryl, C(O)—N(H)—$C_{1-6}$-alkyl-heterocycle, C(O)—N(H)—$C_{1-6}$-alkyl-heteroaryl, wherein the aryl, heteroaryl or heterocyclic groups can be substituted or unsubstituted; and $R^4$ is C(O)N(H)—$C_{1-6}$-alkoxy or $NH_2$.

2. The compound of claim 1, wherein the aryl, heteroaryl and heterocyclic groups of $R^1$ and $R^3$ can optionally be independently substituted one or more times with OH, $C_{1-6}$-alkyl, $C_{1-6}$-alkoxy, $C_{1-6}$-alkyl-heterocycle, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-aryl, $C_{1-6}$-alkyl-heteroaryl, $CF_3$, or halogen;

wherein the substituent aryl, heteroaryl and heterocyclic groups can be further independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen.

3. The compound of claim 1, wherein the aryl, heteroaryl and heterocyclic groups of $R^1$ and $R^3$ can optionally be independently substituted one or more times with $C_{1-6}$-alkyl, $C_{1-6}$-alkoxy, $SO_2$-heterocycle, $C_{1-6}$-alkyl-heterocycle, heterocycle, $CF_3$, or heteroaryl;

wherein the substituent heterocyclic and heteroaryl groups can be optionally further independently substituted one or more times with OH, $C_{1-6}$-alkyl, $C_{1-6}$-alkoxy, $C_{1-6}$-alkyl-OH, or C(O)—$C_{1-6}$-alkyl.

4. The compound of claim 1, wherein $R^1$ is H, C(O)—$C_{3-6}$-cycloalkyl, pyrimidine, C(O)-piperidine, $C_{3-6}$-cycloalkyl, pyridine, phenyl, C(O)-phenyl, C(O)—$C_{1-6}$-alkyl-piperazine, or C(O)-oxazolidinone;

wherein the pyrimidine, piperidine, pyridine, and phenyl groups of $R^1$ can be optionally independently substituted one or more times with OH, $C_{1-6}$-alkyl, $C_{1-6}$-alkoxy, $C(O)$—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen; and wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or $C(O)$—$C_{1-6}$-alkyl.

5. The compound of claim 1, wherein $R^3$ is H, $C(O)$—$N(H)$-phenyl, $C(O)$—$N(H)$—$(CH_2)_2$-morpholino, $C(O)$—$N(H)$—$C_{1-6}$-alkyl-morpholino, or $C(O)$—$N(H)$—$C_{1-6}$-alkyl-imidazole;

wherein the morpholino, imidazole, and phenyl groups of $R^3$ can optionally be independently substituted one or more times with OH, $C_{1-6}$-alkyl, $C_{1-6}$-alkoxy, $C(O)$—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen; and wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or $C(O)$—$C_{1-6}$-alkyl.

6. The compound of claim 1, wherein $R^1$ is $C(O)$—$C_{3-6}$-cycloalkyl, pyrimidine, $C(O)$-piperidine, H, $C_{3-6}$-cycloalkyl, pyridine, Ph-$SO_2$-piperazine, $C(O)$-PhCH$_2$-piperazine-$C_{1-6}$-alkyl, $C(O)$—$C_{1-6}$-alkyl-piperazine, Ph-piperazine-$C_{1-6}$-alkyl, $C(O)$-oxazolidinone-$C_{1-6}$-alkyl-morpholino, wherein the pyrimidine group is optionally independently substituted one or more times with $C_{1-6}$-alkyl or piperazine, wherein the piperazine of the pyrimidine group is optionally substituted with $C_{1-6}$-alkyl-OH; and wherein the $C(O)$—$C_{1-6}$-alkyl-piperazine is optionally substituted with $C(O)C_{1-6}$-alkyl.

7. The compound of claim 1, wherein $R^3$ is H, $C(O)$—$N(H)$-Ph, $C(O)$—$N(H)$—$C_{1-6}$-alkyl-morpholino, or $C(O)$—$N(H)$—$C_{1-6}$-alkyl-imidazole, wherein Ph is optionally substituted one or more times with $CF_3$, $C_{1-6}$-alkyl-piperazine-$C_{1-6}$-alkyl, or imidazole-$C_{1-6}$-alkyl.

8. The compound of claim 1, wherein $R^1$ is $C(O)$-cyclopropyl, pyrimidine, $C(O)$-piperidine, H, cyclopropyl, pyridine, Ph-$SO_2$-piperazine, $C(O)$-PhCH$_2$-piperazine-CH$_2$CH$_3$, $C(O)$—$(CH_2)_2$-piperazine, Ph-piperazine-CH$_3$, or $C(O)$-oxazolidinone-$(CH_2)_3$-morpholino, wherein the pyrimidine is substituted with CH$_3$ and piperazine, wherein the piperazine of the pyrimidine is optionally substituted with $(CH_2)_2$OH, and wherein the piperazine of the $C(O)$—$(CH_2)_2$-piperazine group is optionally substituted with $C(O)CH_3$;

$R^2$ is H, CH$_3$, F or Cl;

$R^3$ is H, $C(O)$—$N(H)$-Ph, $C(O)$—$N(H)$—$(CH_2)_2$-morpholino, $C(O)$—$N(H)$—$(CH_2)_3$-morpholino, or $C(O)$—$N(H)$—$(CH_2)_3$-imidazole, wherein Ph is substituted with $CF_3$ and CH$_2$-piperazine-CH$_2$CH$_3$, or $CF_3$ and imidazole-CH$_3$; and $R^4$ is $C(O)N(H)OCH_3$ or $NH_2$.

9. The compound of claim 1, wherein Formula I is represented by the Formula II:

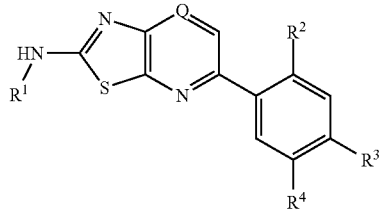

or a pharmaceutically acceptable salt, enantiomer, stereoisomer, rotamer, tautomer, diastereomer, or racemate thereof, wherein Q is CH;

$R^1$ is $C(O)$—$C_{3-6}$-cycloalkyl, $C(O)N(H)$-heteroaryl, $C(O)$-heteroaryl, $C(O)$-aryl, $CO_2$—$C_{1-6}$-alkyl, $C_{3-6}$-cycloalkyl, or $C(O)$—$C_{1-6}$-alkyl-heteroaryl;

$R^2$ and $R^3$ are H; and $R^4$ is $C(O)N(H)$—$C_{1-6}$-alkoxy or $NH_2$;

wherein each of the aryl and heteroaryl groups is substituted or unsubstituted.

10. The compound of claim 9, wherein $R^1$ is $C(O)$—$C_{3-6}$-cycloalkyl;

Q is $C(H)$; and $R^2$ and $R^3$ are H.

11. The compound of claim 1, wherein the compound is of Formula:

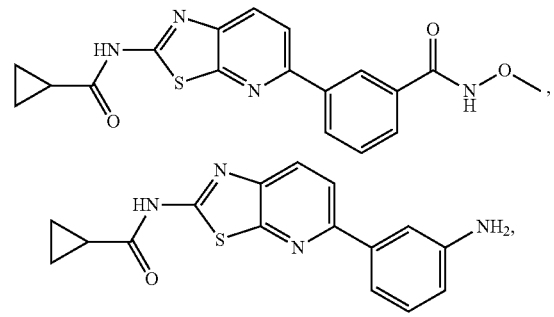

or a pharmaceutically acceptable salt, enantiomer, stereoisomer, rotamer, tautomer, diastereomer, or racemate thereof.

12. A method of treating cancer, comprising administering to a subject in need thereof a compound of claim 1, wherein the cancer is selected from the group consisting of multiple myeloma, chronic myelogenous leukemia, pancreatic cancer, non-small cell lung cancer, lung cancer, breast cancer, colon cancer, ovarian cancer, prostate cancer, malignant melanoma, non-melanoma skin cancers, gastrointestinal stromal tumors, hematologic tumors, hematologic malignancies, childhood leukemia, childhood lymphomas, Hodgkin's disease, lymphomas of lymphocytic origin, lymphomas of cutaneous origin, acute leukemia, chronic leukemia, acute lymphoblastic leukemia, acute myelocytic leukemia, chronic myelocytic leukemia, plasma cell neoplasm, lymphoid neoplasm and cancers associated with AIDS.

13. The method of claim 12, wherein the cancer is pancreatic cancer or non-small cell lung cancer.

14. The method of claim 12, wherein the cancer is gastrointestinal stromal tumor or chronic myelogenous leukemia.

15. The method of claim 12, wherein the cancer is resistant to treatment with Gleevec (Imatinib mesylate) or Imatinib.

16. The method of claim 15, wherein treatment-resistance is due to one or more point-mutations in an Abl kinase, a BCR-Abl kinase domain, a c-kit kinase, an Src kinase or a PDGFR kinase.

17. The method of claim 12 further comprising administering to the subject in need thereof a pharmaceutically effective amount of an additional anti-cancer agent.

18. The method of claim 17, wherein the additional anti-cancer agent is imatinib or nilotinib.

19. The method of claim 12, wherein the cancer is selected from plasma cell neoplasm, chronic myelogenous leukemia, childhood leukemia, childhood lymphomas, Hodgkin's disease, lymphomas of lymphocytic origin, lymphomas of cutaneous origin, acute leukemia, and chronic leukemia.

20. The method of claim 12, wherein the cancer is multiple myeloma.

21. The method of claim 12, wherein the cancer is selected from acute lymphoblastic leukemia, acute myelocytic leukemia, and chronic myelocytic leukemia.

22. The method of claim 12, wherein the cancer is lymphoid neoplasm.

23. A method of inhibiting the activity of a kinase, wherein the kinase is selected from Abl, Abl (T315I), BCR-Abl, BRAF, CDK11, CDK5, CDK2, CDK3, CDK7, DDR1, FLT1, FLT3, FLT4, HIPK1, kit, LOK, p38-gamma, PDGFRA, PDGFRB, Src, RET, TIE2, and VEGFR2, comprising contacting a kinase with a compound of claim 1.

24. A method of inhibiting the activity of Abl kinase, BCR-Abl kinase, c-kit kinase, PDGFRA or PDGFRB kinase, or Src kinase comprising contacting a kinase with a compound of claim 1.

25. A method of treating a disease in a subject, wherein the disease etiology or progression is at least partially mediated by the activity of Abl kinase, BCR-Abl kinase, c-kit kinase, Src kinase, or PDGFR kinase, comprising administering to the subject a compound of claim 1.

26. A compound of Formula III:

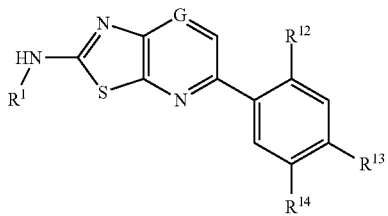

(III)

or a pharmaceutically acceptable salt, enantiomer, stereoisomer, rotamer, tautomer, diastereomer, or racemate thereof;

wherein

G is N or $CR^{10}$;

$R^1$ is H, C(O)—$C_{3-6}$-cycloalkyl, pyrimidine, C(O)N(H)-piperidine, C(O)-piperidine, $C_{3-6}$-cycloalkyl, pyridine, phenyl, C(O)-phenyl, C(O)—$C_{1-6}$-alkyl-piperazine, or C(O)-oxazolidinone, wherein the pyrimidine, piperidine, pyridine, and phenyl groups of $R^1$ can be optionally independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen; and wherein the substituent aryl, heteroaryl and heterocyclic groups can optionally be further independently substituted one or more times with OH, $C_{1-6}$-alkyl, $C_{1-6}$-alkoxy, $C_{1-6}$-alkyl-OH, or C(O)—$C_{1-6}$-alkyl;

$R^{10}$ is H or $C_{1-3}$ alkyl;

$R^{12}$ is H, $C_{1-6}$-alkyl, $C_{1-6}$-alkoxy, or halogen;

$R^{13}$ is H, C(O)—N($R^{28}$)-aryl, C(O)—N($R^{29}$)—$C_{1-6}$-alkyl-heterocycle, C(O)—N($R^{30}$)—$C_{1-6}$-alkyl-heteroaryl, wherein the aryl, heteroaryl or heterocyclic groups are optionally substituted with one or more of OH, $C_{1-6}$-alkyl, $C_{1-6}$-alkoxy, $C_{1-6}$-alkyl-heterocycle, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-aryl, $C_{1-6}$-alkyl-heteroaryl, $CF_3$, or halogen;

wherein the substituent aryl, heteroaryl and heterocyclic groups can be further independently substituted one or more times with OH, $C_{1-6}$-alkyl, $C_{1-6}$-alkoxy, C(O)—$C_{1-6}$-alkyl, $CO_2$—$C_{1-6}$-alkyl, aryl, heteroaryl, heterocycle, $SO_2$-heterocycle, $SO_2$-aryl, $SO_2$-heteroaryl, $C_{1-6}$-alkyl-heterocycle, $C_{1-6}$-alkyl-aryl, $C_{1-6}$-alkyl-heteroaryl, $CF_3$, or halogen; and $R^{14}$ is C(O)$NR^{18}$—$C_{1-6}$-alkoxy or $NR^{23}R^{24}$;

and $R^{18}$, $R^{23}$, $R^{24}$, $R^{28}$, $R^{29}$, and $R^{30}$ are $C_{1-6}$alkyl, halogen, or H.

27. The compound of claim 26, wherein $R^{12}$ is H, $CH_3$, F or Cl;

$R^{13}$ is H, C(O)—N(H)-Ph, C(O)—N(H)—$(CH_2)_2$-morpholino, C(O)—N(H)—$(CH_2)_3$-morpholino, or C(O)—N(H)—$(CH_2)_3$-imidazole, wherein Ph is substituted with $CF_3$ and $CH_2$-piperazine-$CH_2CH_3$, or $CF_3$ and imidazole-$CH_3$; and $R^{14}$ is C(O)N(H)$OCH_3$ or $NH_2$.

* * * * *